US011390590B2

(12) United States Patent
Tapper et al.

(10) Patent No.: US 11,390,590 B2
(45) Date of Patent: *Jul. 19, 2022

(54) METHODS AND PROCESSES FOR THE PREPARATION OF KDM1A INHIBITORS

(71) Applicant: Imago Biosciences, Inc., San Carlos, CA (US)

(72) Inventors: Amy E. Tapper, Boston, MA (US); Cassandra Celatka, Hull, MA (US); Arthur Glenn Romero, Chesterfield, MO (US); John M. McCall, Boca Grande, FL (US); Toni Chancellor, San Carlos, CA (US); Jian-Xie Chen, Schenectady, NY (US); Xuemei Chen, Voorheesville, NY (US); He Zhao, Madison, CT (US); Betina Biolatto, Manalapan, NJ (US); Elisabeth C. A. Brot, Albany, NY (US); Zhihua Li, Beijing (CN); Xiaoming Liao, Beijing (CN)

(73) Assignee: Imago Biosciences, Inc., San Carlos, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/326,495

(22) PCT Filed: Aug. 16, 2017

(86) PCT No.: PCT/US2017/047208
§ 371 (c)(1),
(2) Date: Feb. 19, 2019

(87) PCT Pub. No.: WO2018/035259
PCT Pub. Date: Feb. 22, 2018

(65) Prior Publication Data
US 2021/0139437 A1    May 13, 2021

Related U.S. Application Data

(60) Provisional application No. 62/375,728, filed on Aug. 16, 2016.

(51) Int. Cl.
*C07D 249/06* (2006.01)
*B01J 21/18* (2006.01)
*B01J 23/44* (2006.01)

(52) U.S. Cl.
CPC ........... *C07D 249/06* (2013.01); *B01J 21/18* (2013.01); *B01J 23/44* (2013.01); *C07B 2200/13* (2013.01)

(58) Field of Classification Search
CPC .................................................. C07D 249/06
USPC ...................................................... 544/366
See application file for complete search history.

(56) References Cited

U.S. PATENT DOCUMENTS

| 9,790,195 B2 | 10/2017 | McCall |
| 9,981,922 B2 | 5/2018 | Rienhoff, Jr. |
| 10,370,346 B2 | 8/2019 | Rienhoff, Jr. |
| 10,519,118 B2 | 12/2019 | Rienhoff, Jr. |
| 10,882,835 B2 | 1/2021 | McCall |
| 2009/0162909 A1 | 6/2009 | Campopiano |
| 2009/0191605 A1 | 7/2009 | Liang |
| 2010/0173369 A1 | 7/2010 | Savile |
| 2012/0108500 A1 | 5/2012 | Sakane |
| 2013/0090386 A1 | 4/2013 | Ortega |
| 2015/0225401 A1 | 8/2015 | Wu |
| 2015/0232436 A1 | 8/2015 | Baker |
| 2016/0130215 A1 | 5/2016 | Tomita |
| 2016/0237043 A1 | 8/2016 | Rienhoff, Jr. |
| 2017/0334873 A1 | 11/2017 | McCall |
| 2018/0312474 A1 | 11/2018 | Rienhoff, Jr. |
| 2019/0070172 A1 | 3/2019 | Rienhoff, Jr. |
| 2020/0095214 A1 | 3/2020 | McCall |
| 2020/0283397 A1 | 9/2020 | Rienhoff, Jr. |
| 2021/0115023 A1 | 4/2021 | Tapper |
| 2021/0147373 A1 | 5/2021 | McCall |
| 2021/0196711 A1 | 7/2021 | Rienhoff, Jr. |

FOREIGN PATENT DOCUMENTS

| EP | 2177502 A1 | 4/2010 |
| EP | 2927212 | 10/2015 |
| WO | 2006037028 | 4/2006 |
| WO | 2008103277 | 8/2008 |
| WO | 2009001132 | 12/2008 |
| WO | 2010043721 A1 | 4/2010 |
| WO | 2010143582 A1 | 12/2010 |
| WO | 2011035941 A1 | 3/2011 |
| WO | 2011042217 A1 | 4/2011 |
| WO | 2011131576 A1 | 10/2011 |
| WO | 2011131697 A1 | 10/2011 |
| WO | 2012013727 A1 | 2/2012 |
| WO | 2012013728 A1 | 2/2012 |

(Continued)

OTHER PUBLICATIONS

International Application No. PCT/US2019/032043; International Search Report and Written Opinion of the International Searching Authority, dated Aug. 23, 2019; 10 pages.

(Continued)

*Primary Examiner* — Taofiq A Solola
(74) *Attorney, Agent, or Firm* — Dennis A. Bennett; Lauren L. Stevens; Cynthia Hathaway

(57) ABSTRACT

Provided in this disclosure are methods for the synthesis of substituted 2-arylcyclopropylamines and 2-heteroarylcyclopropylamines and related compounds. Also provided are methods for reduction of thioesters to aldehydes, and methods for reductive animation of cyclopropylamines.

28 Claims, No Drawings

(56) References Cited

FOREIGN PATENT DOCUMENTS

| WO | 2012034116 A2 | 3/2012 |
|---|---|---|
| WO | 2012045883 A1 | 4/2012 |
| WO | 2012047852 | 4/2012 |
| WO | 2012071469 A2 | 5/2012 |
| WO | 2012107498 | 8/2012 |
| WO | 2012107499 A1 | 8/2012 |
| WO | 2012135113 A2 | 10/2012 |
| WO | 2013057320 A1 | 4/2013 |
| WO | 2013057322 A1 | 4/2013 |
| WO | 2014084298 | 6/2014 |
| WO | 2014086790 | 6/2014 |
| WO | 2014164867 | 10/2014 |
| WO | 2014205511 | 12/2014 |
| WO | 2015021128 A1 | 2/2015 |
| WO | 2015162064 | 10/2015 |
| WO | 2015200843 | 12/2015 |
| WO | 2016130952 | 8/2016 |
| WO | 2017079753 A1 | 5/2017 |
| WO | 2017116558 | 7/2017 |
| WO | 2017195216 | 11/2017 |
| WO | 2018035249 | 2/2018 |
| WO | 2018035259 | 2/2018 |
| WO | 2019217972 | 11/2019 |

OTHER PUBLICATIONS

U.S. Appl. No. 15/952,073; Applicant-Initiated Interview Summary, dated Aug. 6, 2019; 2 pages.
U.S. Appl. No. 15/952,073; Notice of Allowance, dated Aug. 6, 2019; 9 pages.
U.S. Appl. No. 15/773,911; Non-Final Office Action, dated Jan. 22, 2020; 38 pages.
U.S. Appl. No. 16/672,083; Application as filed, Nov. 1, 2019; 294 pages.
International Application No. PCT/US2019/032043; International Preliminary Report on Patentability, dated Oct. 26, 2020; 7 pages.
U.S. Appl. No. 15/773,911; Final Office Action, dated Oct. 9, 2020; 26 pages.
U.S. Appl. No. 16/445,768; Notice of Allowance, dated Sep. 2, 2020; 18 pages.
Alvarez-Larrán, A. et al., "Red Cell Mass Measurement in Patients with Clinically Suspected Diagnosis of Polycythemia Vera or Essential Thrombocythemia", Haematologica, 97(11):1704-7, (2012).
Banker, G. et al., Modern Pharmaceutics, Marcel Dekker, New York, 3rd ed., pp. 451 & 596, (1996).
Benelkebir, H. et al., "Enantioselective Synthesis of Tranylcypromine Analogues as Lysine Demethylase (LSD1) Inhibitors", Bioorg Med Chem., 19(12):3709-16, (2011).
Binda, C. et al., "Biochemical, Structural, and Biological Evaluation of Tranylcypromine Derivatives as Inhibitors of Histone Demethylases LSD1 and LSD2", J Am Chem Soc., 132(19):6827-33, (2010).
Byrn, S. et al., Solid-State Chemistry of Drugs, 2nd Ed., Ch. 11 Hydrates and Solvates, 233-47, (1999).
Contente, M. et al., "Preparation of Enantiomerically Enriched Aromatic β-Hydroxynitriles and Halohydrins by Ketone Reduction with Recombinant Ketoreductase KRED1-Pglu", Tetrahedron, 72(27-28):3974-9, (2016).
Gooden, D. et al., "Facile Synthesis of Substituted Trans-2-Arylcyclopropylamine Inhibitors of the Human Histone Demethylase LSD1 and Monoamine Oxidases A and B", Bioorg Med Chem Lett., 18(10):3047-51, (2008).
International Application No. PCT/US2014/023659; International Preliminary Report on Patentability, dated Sep. 15, 2015; 06 pages.
International Application No. PCT/US2014/023659; International Search Report and Written Opinion of the International Search Authority, dated Jul. 29, 2014; 09 pages.
International Application No. PCT/US2014/049906; International Preliminary Report on Patentability, dated Feb. 9, 2016; 07 pages.
International Application No. PCT/US2014/049906; International Search Report and Written Opinion of the International Search Authority, dated Oct. 27, 2016; 08 pages.
International Application No. PCT/US2016/017809; International Preliminary Report on Patentability, dated Aug. 15, 2017; 6 pages.
International Application No. PCT/US2016/017809; International Search Report and Written Opinion of the International Searching Authority, dated May 5, 2016; 8 pages.
International Application No. PCT/US2016/060847; International Preliminary Report on Patentability, dated May 8, 2018; 10 pages.
International Application No. PCT/US2016/060847; International Search Report and Written Opinion of the International Searching Authority, dated Jan. 24, 2017; 14 pages.
International Application No. PCT/US2017/047192; International Preliminary Report on Patentability, dated Feb. 19, 2019; 6 pages.
International Application No. PCT/US2017/047192; International Search Report and Written Opinion of the International Searching Authority, dated Jan. 9, 2018; 9 pages.
International Application No. PCT/US2017/047208; International Search Report and Written Opinion of the International Searching Authority, dated Oct. 30, 2017; 6 pages.
Kaluzna, I. et al., "Ketoreductases: Stereoselective Catalysts for the Facile Synthesis of Chiral Alcohols", Tetrahedron: Asymmetry, 16(22):3682-9, (2005).
Kleppe, M. et al., "Lysine-Specific Histone Demethylase, LSD1, (KDM1A) as a Novel Therapeutic Target in Myeloproliferative Neoplasms", Blood, 126(23):601; 7 pages.
Kreipe, H. et al., "Clonal Granulocytes and Bone Marrow Cells in the Cellular Phase of Agnogenic Myeloid Metaplasia", Blood, 78(7):1814-17, (1991).
Leoni, F. et al., "The Histone Deacetylase Inhibitor ITF2357 Reduces Production of Pro-Inflammatory Cytokines in Vitro and Systemic Inflammation in Vivo", Mol Med., 11(1-12):1-15, (2005).
Lerchner, A. et al., "Macrocyclic BACE-1 Inhibitors Acutely Reduce Abeta in Brain After Po Application", Bioorg Med Chem Lett., 20(2):603-7, (2010).
Lizcano, F. et al., "Epigenetic Control and Cancer: The Potential of Histone Demethylases as Therapeutic Targets", Pharmaceuticals (Basel), 5(9):963-90, (2012).
Mesa, R. et al., "The Myelofibrosis Symptom Assessment Form (MFSAF): An Evidence-Based Brief Inventory to Measure Quality of Life and Symptomatic Response to Treatment in Myelofibrosis", Leuk Res., 33(9):1199-203, (2009).
Morissette, S. et al., "High-Throughput Crystallization: Polymorphs, Salts, Co-Crystals and Solvates of Pharmaceutical Solids", Adv Drug Deliv Rev., 56(3):275-300, (2004).
Myeloproliferative Disorders: University of Maryland Medical Center. (2016). Web: <http://umm.edu/health/medical/altmed/condition/myeloproliferative-disorders>.
Ogasawara, D. et al., "Lysine-Specific Demethylase 1-Selective Inactivators: Protein-Targeted Drug Delivery Mechanism", Angew Chem Int Ed Engl., 52(33):8620-4, (2013).
Ogasawara, D. et al., "Synthesis and Biological Activity of Optically Active NCL-1, a Lysine-Specific Demethylase 1 Selective Inhibitor", Bioorg Med Chem., 19(12):3702-8, (2011).
Quintás-Cardama, A. et al., "Therapy with the Histone Deacetylase Inhibitor Pracinostat for Patients with Myelofibrosis", Leuk Res., 36(9):1124-7, (2012).
Rouhi, A., "The Right Stuff", C&EN:Science and Technology, 81(8):32-5, (2003).
Sareddy, G. et al., "KDM1 is a Novel Therapeutic Target for the Treatment of Gliomas", Oncotarget., 4(1):18-28, (2013).
Schnittger, S. et al., "FLT3 Length Mutations as Marker for Follow-Up studies in Acute Myeloid Leukaemia", Acta Haematol., 112(1-2):68-78, (2004).
Tefferi, A.. et al., "Splenectomy in Myelofibrosis with Myeloid Metaplasia: A Single-Institution Experience with 223 Patients", Blood, 95(7):2226-33, (2000).
The Cleveland Clinic. Myelofibrosis: Prevention. Web: https//my.clevelandclinic.org/health/diseases/15672-myelofibrosis/prevention; 4 pages, (2015).
U.S. Appl. No. 14/910,423; Applicant-lntiated Interview Summary, dated Jun. 12, 2017; 2 pages.

(56) References Cited

OTHER PUBLICATIONS

U.S. Appl. No. 14/910,423; Applicant-Intiated Interview Summary, dated May 1, 2019; 3 pages.
U.S. Appl. No. 14/910,423; Final Office Action, dated Apr. 18, 2017; 7 pages.
U.S. Appl. No. 14/910,423; Non-Final Office Action, dated Sep. 16, 2016; 13 pages.
U.S. Appl. No. 14/910,423; Notice of Allowance, dated Jun. 12, 2017; 4 pages.
U.S. Appl. No. 14/910,423; Notice of Allowance, dated May 2, 2017; 7 pages.
U.S. Appl. No. 15/043,121; Examiner-Intiated Interview Summary, dated Jan. 12, 2018; 1 page.
U.S. Appl. No. 15/043,121; Examiner-Intiated Interview Summary, dated Sep. 18, 2017; 1 page.
U.S. Appl. No. 15/043,121; Non-Final Office Action, dated May 19, 2017; 12 pages.
U.S. Appl. No. 15/043,121; Notice of Allowance, dated Jan. 12, 2018; 7 pages.
U.S. Appl. No. 15/043,121; Notice of Allowance, dated Sep. 18, 2017; 9 pages.
U.S. Appl. No. 15/667,166; Corrected Notice of Allowance, dated May 8, 2019; 8 pages.
U.S. Appl. No. 15/667,166; Examiner-Initiated Interview Summary, dated May 8, 2019; 1 page.
U.S. Appl. No. 15/667,166; Non-Final Office Action, dated Aug. 23, 2018; 9 pages.
U.S. Appl. No. 15/667,166; Notice of Allowance, dated Mar. 19, 2019; 16 pages.
U.S. Appl. No. 15/952,073; Final Office Action, dated Apr. 11, 2019; 13 pages.
U.S. Appl. No. 15/952,073; Non-Final Office Action, dated Sep. 6, 2018; 31 pages.
U.S. Appl. No. 16/326,498; Application as filed dated Feb. 19, 2019; 61 pages.
U.S. Appl. No. 16/445,768; Application as filed, dated Jun. 19, 2019; 128 pages.
Wang, J. et al., "Novel Histone Demethylase LSD1 Inhibitors Selectively Target Cancer Cells with Pluripotent Stem Cell Properties", Cancer Res., 71(23):7238-49, (2011).
Wolff, M., Burger's Medicinal Chemistry and Drug Discovery, Principles and Practice, John Wiley & Sons, 5(1):975-7, (1995).
Zeppa, P. et al., "Fine-Needle Aspiration Biopsy and Flow Cytometry Immunophenotyping of Lymphoid and Myeloproliferative Disorders of the Spleen", Cancer, 99(2):118-27, (2003).
Miyamura, S. et al., "C-H activation enables a rapid structure-activity relationship study of arylcyclopropyl amines for potent and selective LSDI inhibitors", Org Biomol Chem., 14(36):8576-85, (2016).
U.S. Appl. No. 16/672,083; Notice of Allowance, dated Jun. 23, 2021; 11 pages.
U.S. Appl. No. 17/481,649; Application as filed, dated Sep. 22, 2021; 294 pages.

METHODS AND PROCESSES FOR THE PREPARATION OF KDM1A INHIBITORS

This application claims the benefit of U.S. Provisional Application No. 62/375,728, filed Aug. 16, 2016, the entirety of which is hereby incorporated by reference as if written herein in its entirety.

Inhibiting the enzyme KDM1A (also known as lysine-specific demethylase 1, LSD1, Flavin-containing Amine Oxidase Domain-Containing Protein, AOF2, BRAF35-HDAC Complex Protein BHC110, FAD-Binding Protein BRAF35-HDAC Complex), may alter gene expression in cells sufficient to restore their proper physiologic function or that of the tissue, organ or the patient as a whole. This may be achieved either by enhancing transcription of a gene or genes that are pathologically silenced, e.g., as is the case in some cancer cells and heritable diseases, or decreasing transcription of a gene or genes participating in the pathological state. As such, inhibiting KDM1A would be useful for the treatment of diseases such as cancer and heritable diseases such as Wilson disease, cardiomyopathies, and hemoglobinopathies.

Novel potent inhibitors of KDM1A have been described, for example, in WO 2014/164,867, WO 2015/021128, and PCT/US2016/17809. The compound N-[2S)-1-(4-(methyl) piperazin-1-yl)-5-[[(1R,2S)-2-(4-fluorophenyl)-cyclopropyl]amino]-1-oxopentan-2-yl]-4-(1H-1,2,3-triazol-1-yl) benzamide and related compounds have been described in PCT/US2016/17809, the contents of which are hereby incorporated by reference, as inhibitors of KDM1A with promising potential. There thus exists a need for new and improved methods for the synthesis of N-[2S)-1-(4-(methyl) piperazin-1-yl)-5-[[(1R,2S)-2-(4-fluorophenyl)-cyclopropyl]amino]-1-oxopentan-2-yl]-4-(1H-1,2,3-triazol-1-yl) benzamide and related compounds which are amenable to large-scale synthesis.

In one embodiment the invention provides a process for preparing compounds of Formula IV:

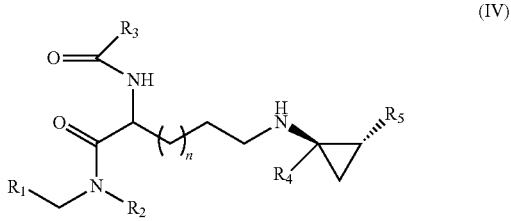

(IV)

or a salt, polymorph, or solvate thereof, wherein:
  n is 1 or 2;
  $R^1$ and $R^2$ together with the nitrogen to which they attach, form a nitrogen-containing heterocycloalkyl or heteroaryl ring, which may be optionally substituted with between 0 and 3 $R^6$ groups;
  $R^3$ is phenyl substituted with halogen, cyano, or heteroaryl;
  $R^4$ is hydrogen;
  $R^5$ is chosen from aryl and heteroaryl, any of which may be optionally substituted with between 0 and 3 $R^6$ groups;
  each $R^6$ is hydrogen, hydroxyl, alkyl, cycloalkyl, heterocycloalkyl, cyano, amino, alkylamino, dialkylamino, $CONHR^7$, and $CONR^7R^8$; and
  $R^7$ and $R^8$ are independently chosen from hydrogen, and lower alkyl; or $R^7$ and $R^8$ may be taken together to form a nitrogen-containing heterocycloalkyl or heteroaryl ring, which may be optionally substituted with lower alkyl;

comprising reacting a compound of Formula II:

Formula II or a salt thereof; wherein:
  $R^5$ is chosen from aryl and heteroaryl, any of which may be optionally substituted with between 0 and 3 $R^6$ groups;
  wherein $R^6$ is defined as above;
with a compound of Formula III:

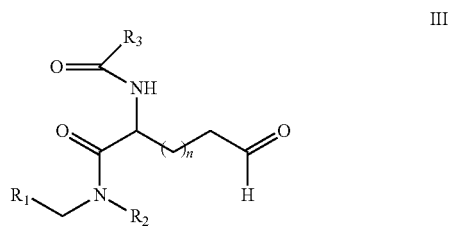

III or a salt thereof; wherein:
  $R^1$ and $R^2$ together with the nitrogen to which they attach, form a nitrogen-containing heterocycloalkyl or heteroaryl ring, which may be optionally substituted with between 0 and 3 $R^6$ groups; and
  $R^3$ is phenyl substituted with halogen, cyano, or heteroaryl;
  wherein $R^6$ is as defined above;
under reductive amination reaction conditions.

In some embodiments, the compound of Formula III exists in equilibrium with compounds of Formulas III(a-d), depicted below:

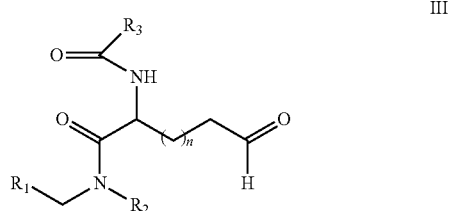

III

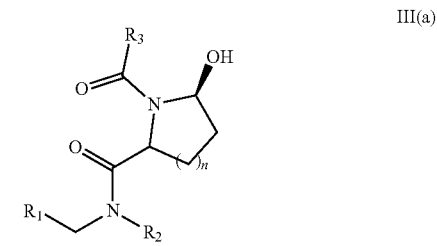

III(a)

III(b)
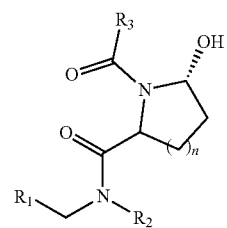

III(c)
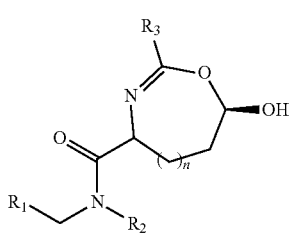

III(d)
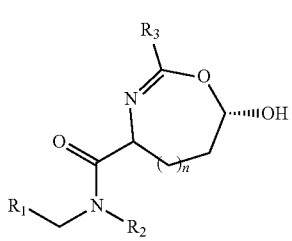

The person of skill in the art will appreciate that the formation of cyclic structures such as Formulas III(a-d) is very common for functionalized aliphatic aldehydes, and that equilibrium between the aldehyde structure and Formulas III(a-d) is rapid. The relative proportion of Formulas III and III(a-d) is highly dependent on factors such as molecular structure, solvent composition, pH, and ionic strength. Due to the relatively high reactivity of the aldehyde of Formula III, combined with the fast equilibrium with the alternate Formulas III(a-d), the possible existence of Formulas III(a-d) does not interfere with the reactivity of the compound of Formula III, as disclosed herein.

In some embodiments, the compound of Formula IV is Compound 7:

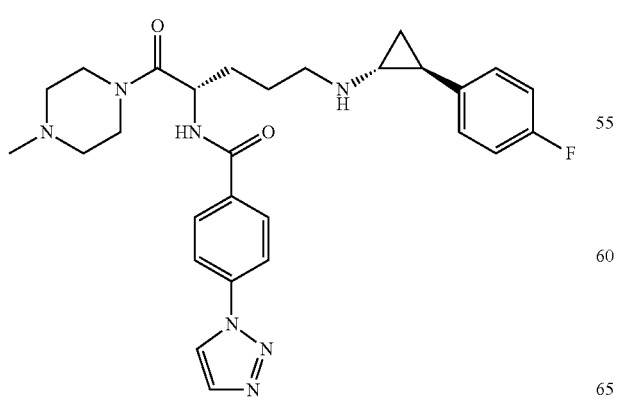

N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide In some embodiments, the compound of Formula II is Compound 9:

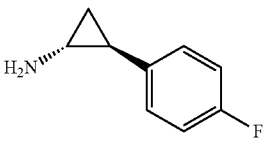

In some embodiments, the compound of Formula III is Compound 6:

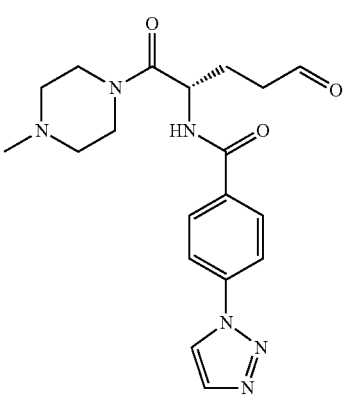

In some embodiments, the reductive amination conditions comprise reacting the compound of Formula II with the compound of Formula III in the presence of a borohydride reducing agent. In some embodiments, the borohydride reducing agent is $NaBH_4$. In some embodiments, the reductive amination is carried out in a co-solvent mixture comprising an alcohol. In some embodiments, the co-solvent mixture comprises methanol and tetrahydrofuran.

Also provided is a process for preparing a compound of Formula III comprising reducing a thioester of Formula I:

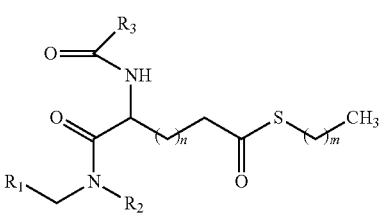

wherein:
n is 1 or 2;
m is 0-12;
$R^1$ and $R^2$ together with the nitrogen to which they attach, form a nitrogen-containing heterocycloalkyl or heteroaryl ring, which may be optionally substituted with between 0 and 3 $R^6$ groups; and $R^3$ is phenyl substituted with halogen, cyano, or heteroaryl;
wherein $R^6$ is as defined above;
to provide an aldehyde of Formula III.

In some embodiments, the compound of Formula I is Compound 5.

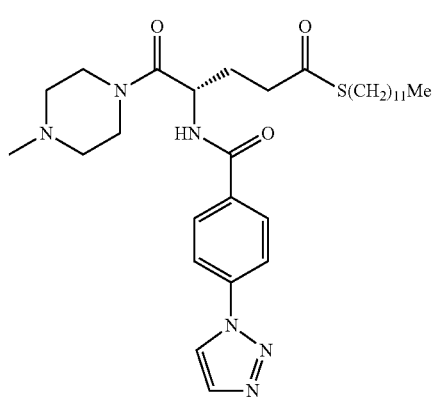

In some embodiments, the reduction of the thioester compound of Formula I utilizes a silane reducing agent. In some embodiments, the silane reducing agent is triethylsilane. In some embodiments, the reduction further comprises palladium on carbon.

Also provided are methods for preparing a compound of Formula III from an acid salt of thioester of Formula I, designated I*HX, comprising: 1) a free base step, comprising reaction of the salt I*HX with a base, to form the corresponding free base I, and 2) a reduction step, comprising a method for reducing a thioester of Formula I to provide a compound of Formula III, as disclosed herein.

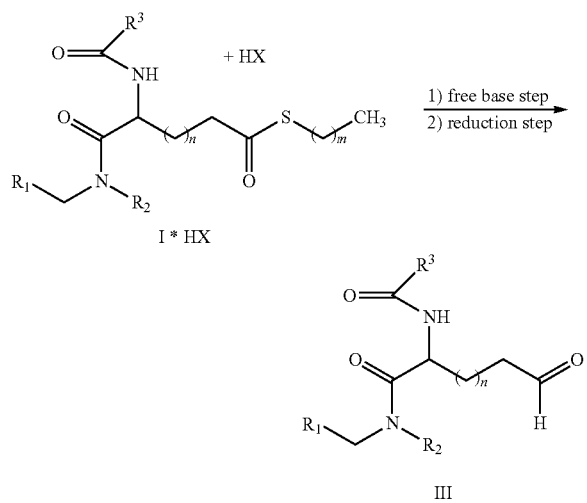

wherein:
m is 0-12;
$R^1$ and $R^2$ together with the nitrogen to which they attach, form a nitrogen-containing heterocycloalkyl or heteroaryl ring, which may be optionally substituted with between 0 and 3 $R^6$ groups;
$R^3$ is phenyl substituted with halogen, cyano, or heteroaryl; and
wherein $R^6$ is as defined above.

In some embodiments, the reduction step further utilizes a Pd-based catalyst. In some embodiments, the Pd-based catalyst is a Pd(0) catalyst. In some embodiments, the Pd(0) catalyst is palladium on carbon. In some embodiments, the palladium on carbon is an eggshell catalyst. In some embodiments, the Pd-based catalyst is a Pd(II) catalyst.

In some embodiments, the compound of Formula I*HX is Compound 5*HCl.

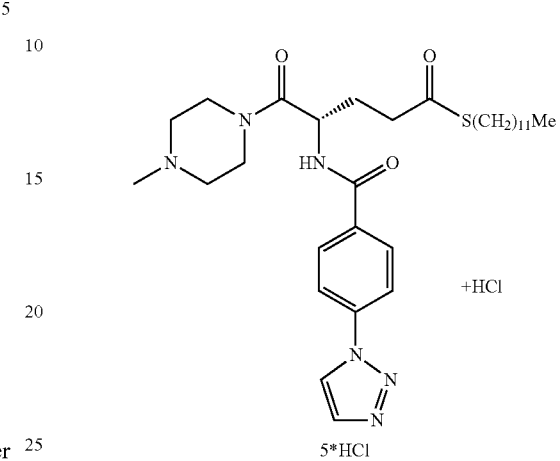

Also provided are methods for preparing thioesters of Formula I, comprising reacting a carboxylic acid compound of Formula V with a thiol compound of Formula VI:

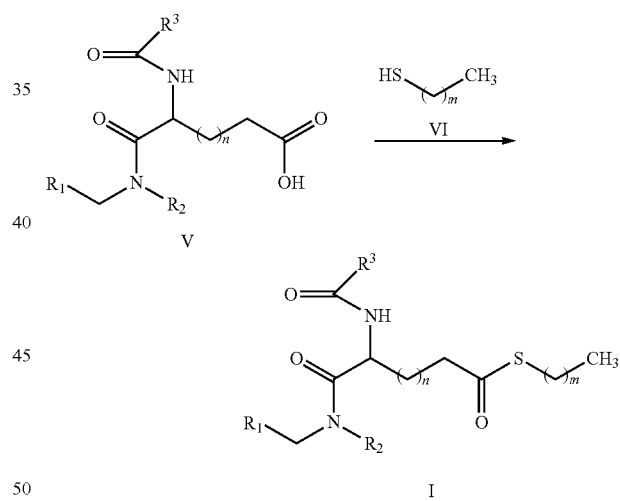

wherein:
n is 1 or 2;
m is 0-12;
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;
with an appropriate coupling agent.

In some embodiments, the coupling agent for the reaction of the compound is 1-ethyl-3-(3-dimethylaminopropyl)carbodiimide hydrochloride (EDC), or a salt thereof. In some embodiments, the reaction between the compound of Formula V and the compound of Formula VI further comprises 4-dimethylaminopyridine (DMAP). In some embodiments, DMAP is present in a catalytic amount.

In some embodiments, m in Formula VI is 11.

Also provided are methods for preparing acid salts of thioesters of Formula I, comprising 1) a thioester formation step, comprising a method for synthesis of a thioester of Formula I, as disclosed herein, and 2) a salt formation step, comprising reaction with acid HX, to form the corresponding salt of Formula I, designated I*HX:

wherein:
n is 1 or 2;
m is 0-12;
$R^1$ and $R^2$ together with the nitrogen to which they attach, form a nitrogen-containing heterocycloalkyl or heteroaryl ring, which may be optionally substituted with between 0 and 3 $R^6$ groups;
$R^3$ is phenyl substituted with halogen, cyano, or heteroaryl; and
wherein $R^6$ is as defined above.

Also provided are methods for preparing a compound of Formula V wherein n is 1 (compounds of Formula XII) from glutamic acid, comprising the steps:
a. reacting a protected glutamate ester VII with an appropriate heterocycle VIII to provide a compound of Formula IX:

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

b. removing the protecting group from the glutamate amino group of the compound of Formula IX to provide a compound of Formula X:

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

c. reacting the compound of Formula X with an appropriate substituted benzoic acid to provide a compound of Formula XI:

wherein:
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;
and d. converting the ester group of the compound of Formula XI to a carboxylic acid to provide a compound of Formula XII:

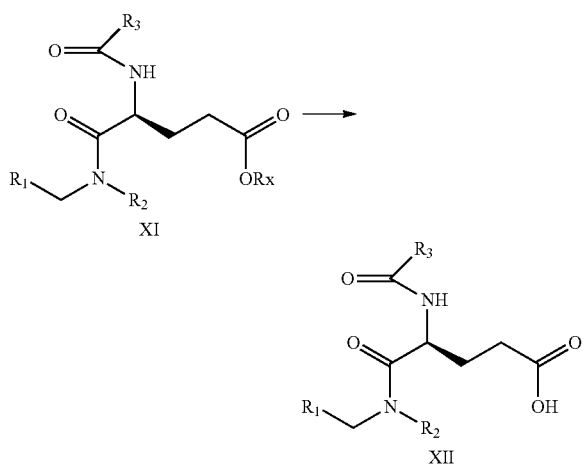

wherein:
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above.

Also provided are methods for preparing a compound of Formula IV wherein n is 1 (compounds of Formula XVI) from glutamic acid, comprising the steps:

a. reacting a protected glutamate ester VII with an appropriate heterocycle VIII to provide a compound of Formula IX:

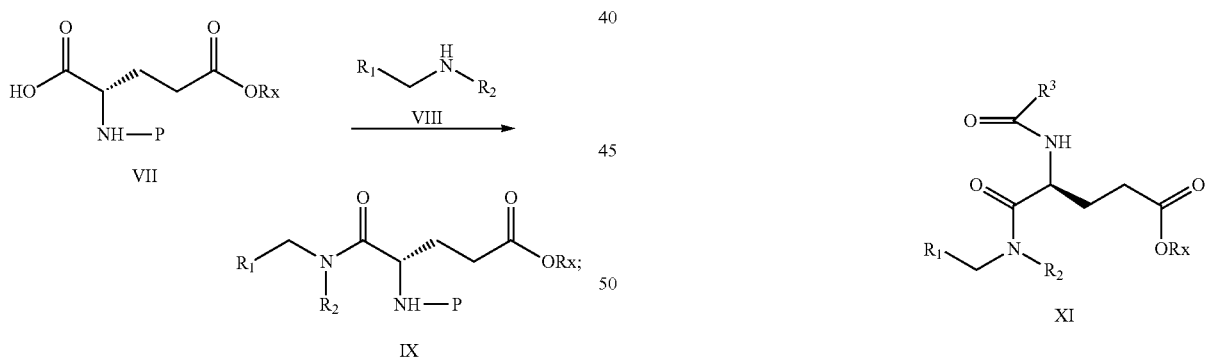

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

b. removing the protecting group from the glutamate amino group of the compound of Formula IX to provide a compound of Formula X:

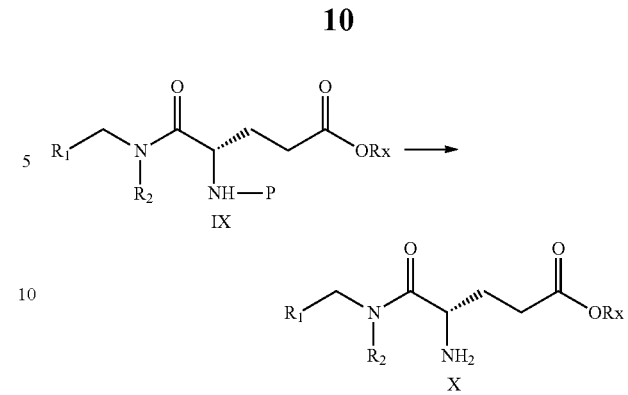

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

c. reacting the compound of Formula X with an appropriate substituted benzoic acid to provide a compound of Formula XI:

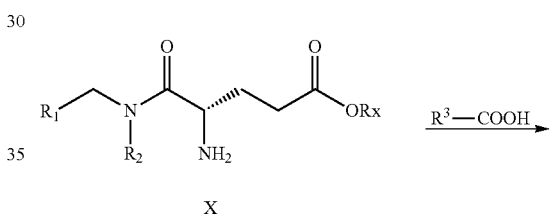

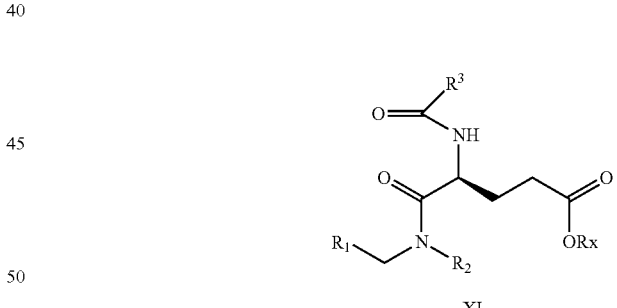

wherein:
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;

d. converting the ester group of the compound of Formula XI to a carboxylic acid to provide a compound of Formula XII:

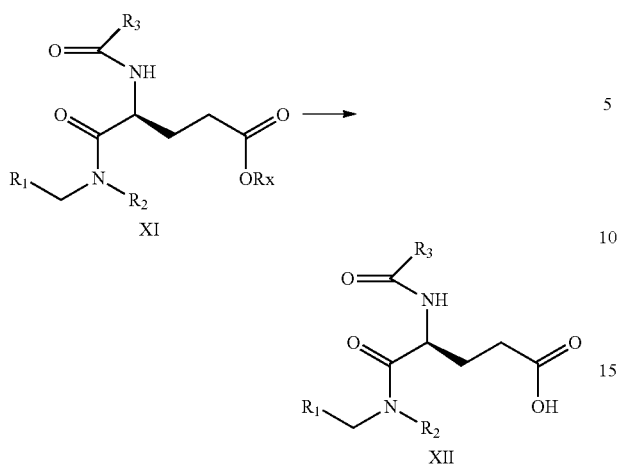

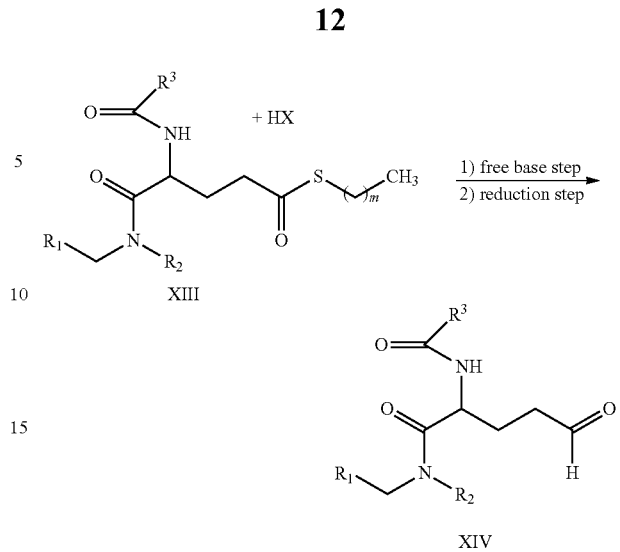

wherein:
Rx is an alkyl group; and
R¹ and R² together with the nitrogen to which they attach, form a nitrogen-containing heterocycloalkyl or heteroaryl ring, which may be optionally substituted with between 0 and 3 R⁶ groups; and
R³ is phenyl substituted with halogen, cyano, or heteroaryl;
wherein R⁶ is as defined above;

e. converting the compound of Formula XII to the compound of Formula XIII, comprising 1) a thioester formation step, and 2) a salt formation step:

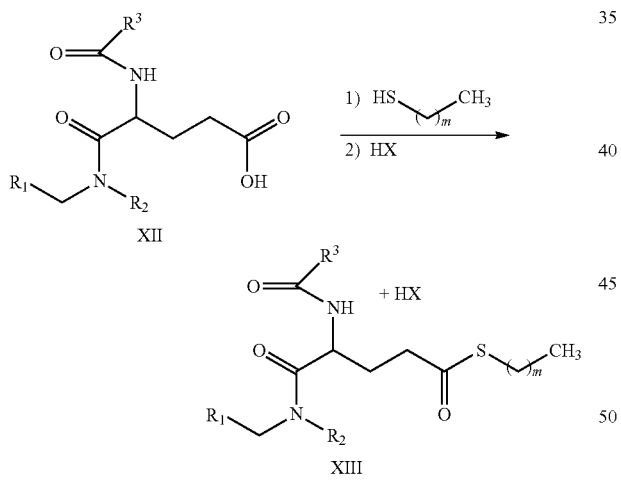

wherein:
m is 0-12;
R¹ and R² together with the nitrogen to which they attach, form a nitrogen-containing heterocycloalkyl or heteroaryl ring, which may be optionally substituted with between 0 and 3 R⁶ groups;
R³ is phenyl substituted with halogen, cyano, or heteroaryl; and
wherein R⁶ is as defined above;

f. converting the compound of Formula XIII to the compound of formula XIV, comprising: 1) a free base step, comprising reaction of the salt XIII with a base, and 2) a reduction step:

wherein:
m is 0-12;
R¹ and R² together with the nitrogen to which they attach, form a nitrogen-containing heterocycloalkyl or heteroaryl ring, which may be optionally substituted with between 0 and 3 R⁶ groups;
R³ is phenyl substituted with halogen, cyano, or heteroaryl; and
wherein R⁶ is as defined above;

g. converting the compound of Formula XIV to the compound of Formula XV, by reaction with a compound of Formula II under reductive amination conditions:

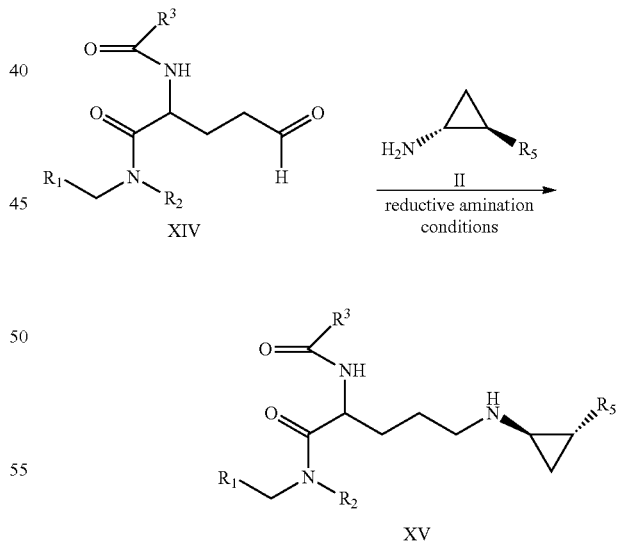

wherein:
R¹ and R² together with the nitrogen to which they attach, form a nitrogen-containing heterocycloalkyl or heteroaryl ring, which may be optionally substituted with between 0 and 3 R⁶ groups; and
R³ is phenyl substituted with halogen, cyano, or heteroaryl;

$R^5$ is chosen from aryl and heteroaryl, any of which may be optionally substituted with between 0 and 3 $R^6$ groups;

wherein $R^6$ is defined as above;

and h. converting the compound of Formula XV to the compound of Formula XVI, by reaction with an acid compound HX:

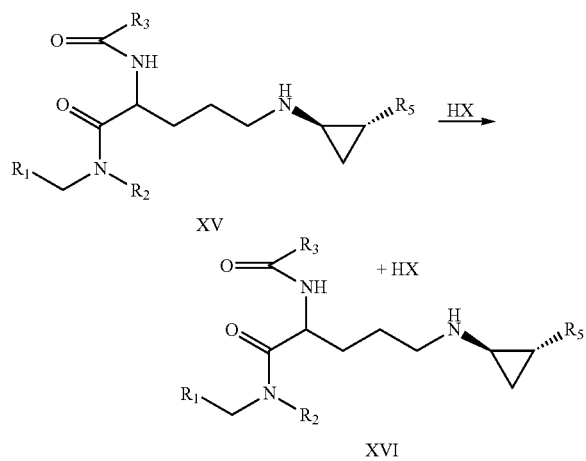

wherein:

$R^1$ and $R^2$ together with the nitrogen to which they attach, form a nitrogen-containing heterocycloalkyl or heteroaryl ring, which may be optionally substituted with between 0 and 3 $R^6$ groups; and $R^3$ is phenyl substituted with halogen, cyano, or heteroaryl;

$R^5$ is chosen from aryl and heteroaryl, any of which may be optionally substituted with between 0 and 3 $R^6$ groups;

wherein $R^6$ is as defined above.

DETAILED DESCRIPTION OF THE INVENTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% from the specified amount.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(═O)—NR$_2$ group with R as defined herein. The term "N-amido" as used herein, alone or in combination, refers to a RC(═O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, hydroxyalkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "amino acid", as used herein, alone or in combination, refers to a —NHCHRC(O)O— group, which may be attached to the parent molecular moiety to give either an N-terminus or C-terminus amino acid, wherein R is independently chosen from hydrogen, alkyl, aryl, heteroaryl, heterocycloalkyl, aminoalkyl, amido, amidoalkyl, carboxyl, carboxylalkyl, guanidinealkyl, hydroxyl, thiol, and thioalkyl, any of which themselves may be optionally substituted. The term C-terminus, as used herein, alone or in combination, refers to the parent molecular moiety being bound to the amino acid at the amino group, to give an amide as described herein, with the carboxyl group unbound, resulting in a terminal carboxyl group, or the corresponding carboxylate anion. The term N-terminus, as used herein, alone or in combination, refers to the parent molecular moiety being bound to the amino acid at the carboxyl group, to give an ester as described herein, with the amino group unbound resulting in a terminal secondary amine, or the corresponding ammonium cation. In other words, C-terminus refers to —NHCHRC(O)OH or to —NHCHRC(O)O— and N-terminus refers to H$_2$NCHRC(O)O— or to H$_3$N$^+$CHRC(O)O—.

The term "aryl", as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C$_6$H$_4$═ derived from benzene. Examples include benzothiophene and benzimidazole.

The term "biphenyl" as used herein refers to two phenyl groups connected at one carbon site on each ring.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halohydrin," as used herein, alone or in combination, refers to a compound or functional group in which one carbon atom has a halogen substituent, and another carbon atom has a hydroxyl substituent, typically on adjacent carbons.

The term "guanidine", as used herein, alone or in combination, refers to —NHC(=NH)NH$_2$, or the corresponding guanidinium cation.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogen atoms are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furanyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuranyl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl, azepinyl, diazepinyl, benzazepinyl, and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylalkyl" as used herein alone or as part of another group refers to alkyl groups as defined above having a heteroaryl substituent.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, imidazolidinyl, isoindolinyl, morpholinyl, oxazolidinyl, isoxazolidinyl, piperidinyl, piperazinyl, methylpiperazinyl, N-methylpiperazinyl, pyrrolidinyl, pyrazolidinyl, tetrahydrofuranyl, tetrahydropyridinyl, thiomorpholinyl, thiazolidinyl, diazepanyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "hydroxamic acid", as used herein, alone or in combination, refers to —C(=O)NHOH, wherein the parent molecular moiety is attached to the hydroxamic acid group by means of the carbon atom.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate," as used herein, alone or in combination, refers to a —P(=O)(OR)$_2$ group, wherein R is chosen from alkyl and aryl. The term "phosphonic acid", as used herein, alone or in combination, refers to a —P(=O)(OH)$_2$ group.

The term "phosphoramide", as used herein, alone or in combination, refers to a —P(=O)(NR)$_3$ group, with R as defined herein.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. Similarly, when a designation such as "n" which may be chosen from a group or range of integers is designated to be 0, then the group which it designates is either absent, if in a terminal position, or condenses to form a bond, if it falls between two other groups.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated according to the Cahn-Ingold-Prelog priority rules by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reaction of the appropriate compound, in the form of the free base, with the appropriate acid.

The compounds disclosed herein can exist as polymorphs and other distinct solid forms such as solvates, hydrates, and the like. A compound may be a polymorph, solvate, or hydrate of a salt or of the free base or acid.

The present disclosure provides methods for synthesizing N-[2S]-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide and related compounds.

In one embodiment the invention provides a process for preparing compounds of Formula IV:

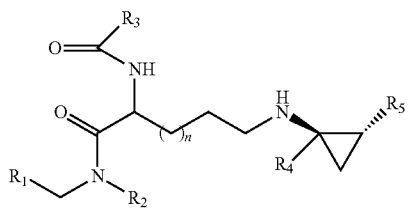

or a salt, polymorph, or solvate thereof, wherein:
n is 1 or 2;
$R^1$ and $R^2$ together with the nitrogen to which they attach, form a nitrogen-containing heterocycloalkyl or heteroaryl ring, which may be optionally substituted with between 0 and 3 $R^6$ groups;
$R^3$ is phenyl substituted with halogen, cyano, or heteroaryl;
$R^4$ is hydrogen;
$R^5$ is chosen from aryl and heteroaryl, any of which may be optionally substituted with between 0 and 3 $R^6$ groups;
each $R^6$ is hydrogen, hydroxyl, alkyl, cycloalkyl, heterocycloalkyl, cyano, amino, alkylamino, dialkylamino, CONHR$^7$, and CONR$^7$R$^8$; and
$R^7$ and $R^8$ are independently chosen from hydrogen, and lower alkyl; or
$R^7$ and $R^8$ may be taken together to form a nitrogen-containing heterocycloalkyl or heteroaryl ring, which may be optionally substituted with lower alkyl;
comprising reacting a compound of Formula II:

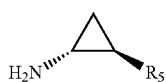

Formula II or a salt thereof, wherein:
$R^5$ is chosen from aryl and heteroaryl, any of which may be optionally substituted with between 0 and 3 $R^6$ groups;
wherein $R^6$ is defined as above;
with a compound of Formula III:

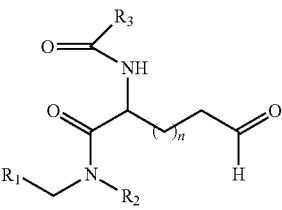

III or a salt thereof, wherein:
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;
under reductive amination reaction conditions.

In certain embodiments, n is 1.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

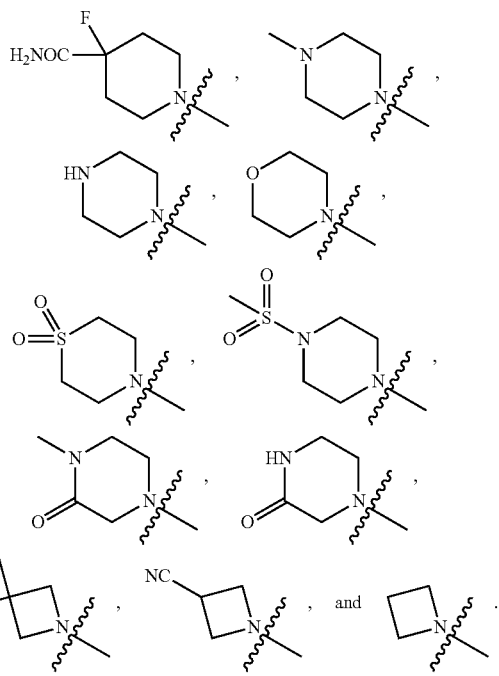

In certain embodiments, the nitrogen-containing heterocycloalkyl is:

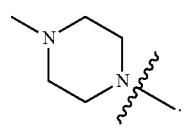

In certain embodiments, the nitrogen-containing heterocycloalkyl is optionally substituted with between 0 and 3 $R^6$ groups chosen from alkyl and oxo.

In certain embodiments, $R^5$ is phenyl, which may be optionally substituted with between 0 and 3 $R^6$ groups.

In certain embodiments, $R^5$ is:

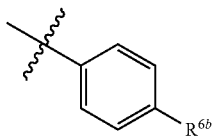

wherein $R^{6b}$ is chosen from halogen and alkoxy.

In certain embodiments, $R^{6b}$ is chosen from fluoro and methoxy.

In certain embodiments, $R^{6b}$ is fluoro.

In certain embodiments, $R^3$ is phenyl substituted with heteroaryl.

In certain embodiments, $R^3$ is phenyl substituted with heteroaryl selected from the group consisting of:

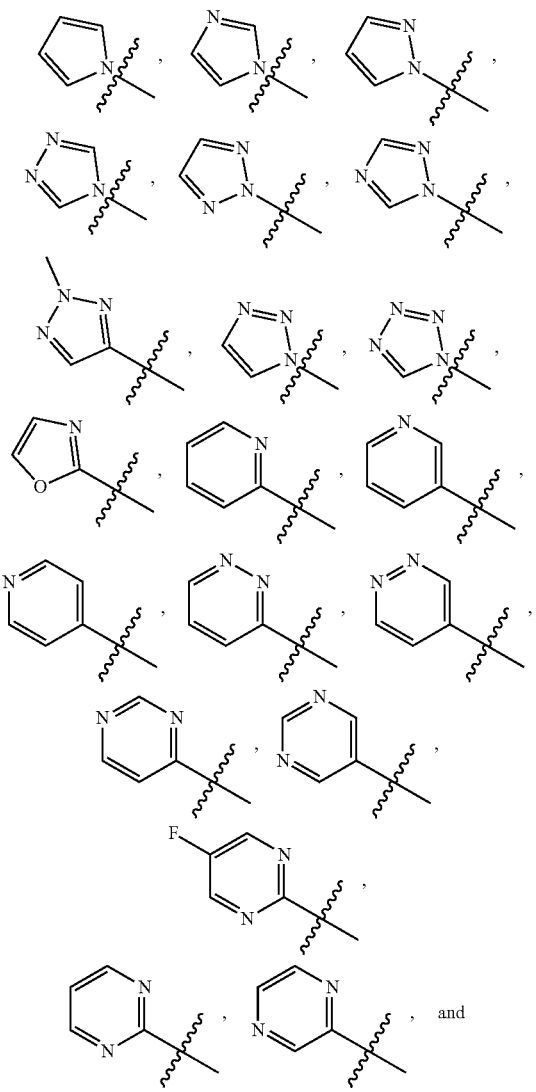

In certain embodiments, $R^3$ is phenyl substituted with

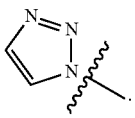

In certain embodiments, the compound of Formula IV is Compound 7:

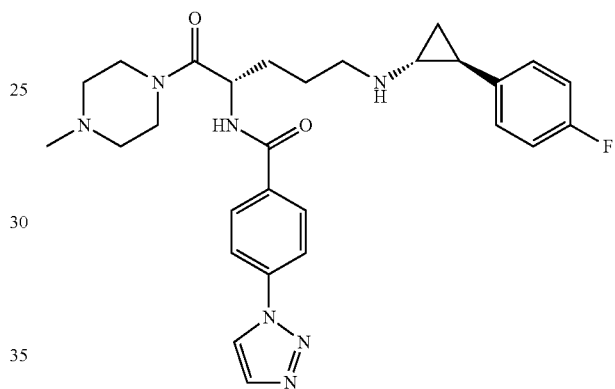

In certain embodiments, the compound of Formula II is Compound 9:

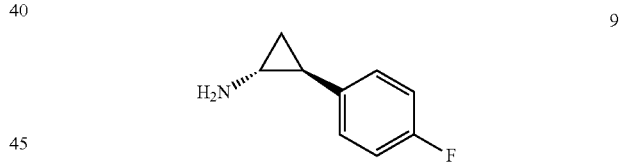

In certain embodiments, the compound of Formula III is Compound 6:

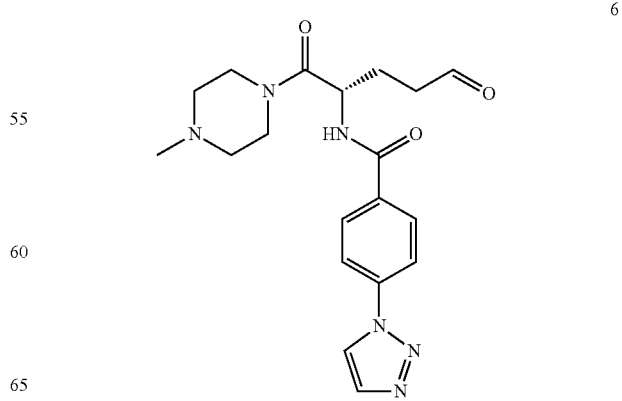

The reductive amination conditions that may be used in the present invention are known to those of skill in the art of organic synthesis. Examples of such reaction conditions may be found, by way of non-limiting example, in: M. Taibakhsh, R. Hosseinzadeh, H. Alinezhad, S. Ghahari, A. Heydari, S. Khaksar, *Synthesis,* 2011, 490-496; A. F. Abdel-Magid, K. G. Carson, B. D. Harris, C. A. Maryanoff, R. D. Shah, *J. Org. Chem.,* 1996, 61, 3849-3862; and O. S. Nayal, V. Bhatt, S. Sharma, N. Kumar, *J. Org. Chem.,* 2015, 80, 5912-5918. In certain embodiments, the reductive amination conditions comprise reacting the compound of Formula II with the compound of Formula III in the presence of a borohydride reducing agent. In certain embodiments, the borohydride reducing agent is $NaBH_4$. In certain embodiments, the borohydride reducing agent is $NaBH(OAc)_3$.

In certain embodiments, the reductive amination is performed in a solvent selected from a lower carbinol, 2,2,2-trifluoroethanol, dichloromethane, tetrahydrofuran, and acetonitrile.

In certain embodiments, the reductive amination is performed in a solvent comprising a lower carbinol.

In certain embodiments the lower carbinol is methanol.

In certain embodiments the lower carbinol is part of a co-solvent mixture.

In certain embodiments the co-solvent mixture comprises methanol and tetrahydrofuran. In some embodiments, the co-solvent mixture consists of a 2:1 (v:v) mixture of methanol and tetrahydrofuran.

In certain embodiments $NaBH_4$ is added to a mixture of Compound 6 and Compound 9 in a mixture of methanol and tetrahydrofuran which has been cooled to $-5\pm5°$ C.

In certain embodiments $NaBH_4$ is added to a mixture of Compound 6 and Compound 9 in a mixture of methanol and tetrahydrofuran which has been cooled to $-10\pm5°$ C.

In some embodiments, at most 1.1 equivalents of Compound 9, relative to Compound 6, is used.

In some embodiments, at most 1.0 equivalents of Compound 9, relative to Compound 6, is used.

In certain embodiments the $NaBH_4$ is added in portions while maintaining the reaction mixture temperature at less than 22° C.

In certain embodiments the $NaBH_4$ is added in at least 5 portions spaced at least 15 minutes apart.

In certain embodiments the reaction mixture is stirred at $20\pm5°$ C. following completion of the addition of $NaBH_4$ in portions.

In certain embodiments the reaction mixture is stirred at $20\pm5°$ C. for at least 1 hour.

In certain embodiments the reaction mixture is stirred at $20\pm5°$ C. for at least 3 hours.

In certain embodiments the reductive amination further comprises the steps of:
1) stirring the reaction mixture until Compound 7 is present at least 75 area % by HPLC analysis;
2) quenching the reaction mixture by the addition of saturated $NH_4Cl$; and
3) concentrating the resulting mixture.

In certain embodiments, the reductive amination further comprises the steps of:
1) partitioning the product after between an aqueous phase and an IPAc phase;
2) adjusting the pH of the aqueous phase to 9-10 by the addition of NaOH;
3) separating the IPAc phase;
4) extracting the aqueous phase with IPAc; and
5) obtaining Compound 7 from the combined IPAc phases.

In certain embodiments, the HPLC method used to determine the area % of Compound 7 in the reductive amination reaction mixture is Test Method TM.04762, as disclosed herein.

Also provided is a process for preparing a compound of Formula III comprising reducing a thioester of Formula I:

I wherein:
n is 1 or 2;
m is 0-12;
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;
to provide an aldehyde of Formula III.

In certain embodiments, n is 1.

In certain embodiments, m is 11.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

In certain embodiments, the nitrogen-containing heterocycloalkyl is:

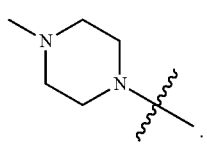 [SMILES: *N1CCN(C)CC1]

In certain embodiments, the nitrogen-containing heterocycloalkyl is optionally substituted with between 0 and 3 $R^6$ groups chosen from alkyl and oxo.

In certain embodiments, $R^3$ is phenyl substituted with heteroaryl.

In certain embodiments, $R^3$ is phenyl substituted with heteroaryl selected from the group consisting of:

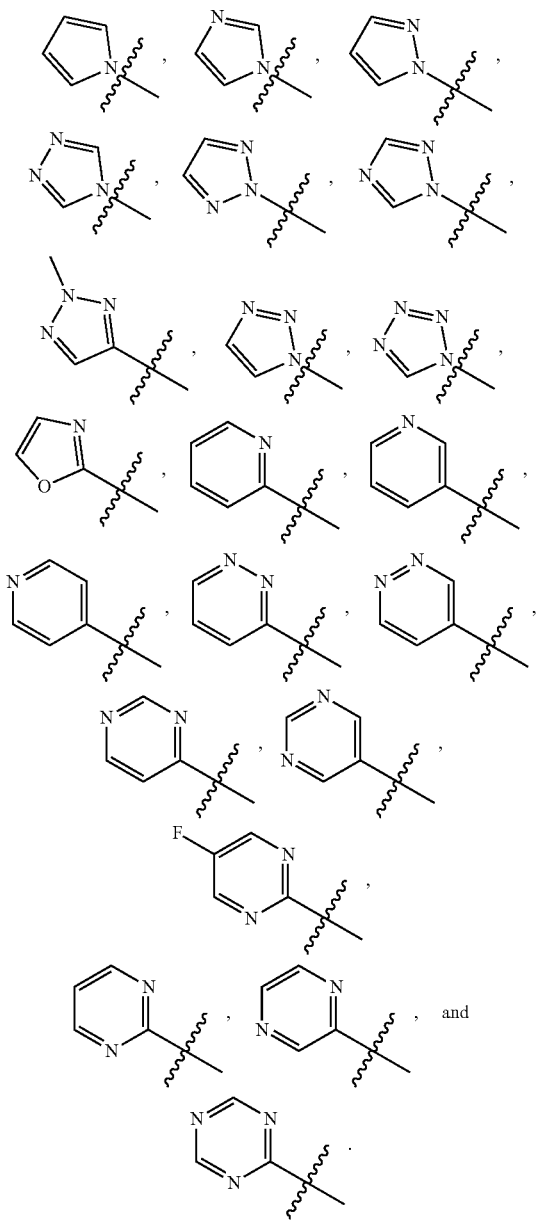

In certain embodiments, $R^3$ is phenyl substituted with

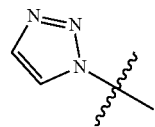

In some embodiments, the compound of Formula I is Compound 5.

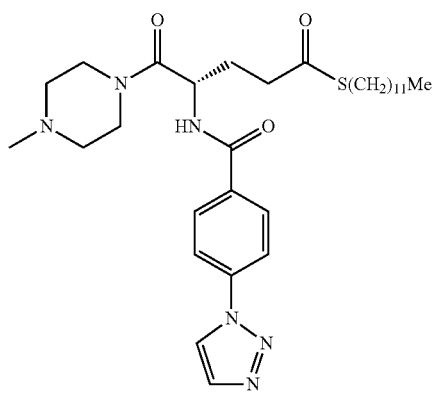

5

The reduction conditions that may be used in the present invention to reduce thioesters of Formula I to aldehydes of Formula III are known to those of skill in the art of organic synthesis. Examples of such reaction conditions may be found, by way of non-limiting example, in: T. Fukuyma, H. Tokuyama, *Aldrichimica Acta* 2004, 37, 87.

In some embodiments, the reduction of the thioester compound of Formula I utilizes a silane reducing agent. In some embodiments, the silane reducing agent is triethylsilane. In some embodiments, 4.0 equivalents of triethylsilane, relative to thioester of Formula I, is used.

In some embodiments, the reduction further comprises palladium on carbon. In certain embodiments, the reduction may be carried out as described by Fukuyama et al.: H. Tokuyama, S. Yokoshima, S.-C. Lin, L. Li, T. Fukuyama, *Synthesis,* 2002, 1121-1123.

In some embodiments, the reduction further comprises a Pd(0) catalyst. In some embodiments, the Pd(0) catalyst is palladium on carbon. In some embodiments, the palladium on carbon is anhydrous. In some embodiments, about 2.5% (w/w) of palladium on carbon catalyst, relative to thioester of Formula I, is used. In some embodiments, about 5% (w/w) of palladium on carbon catalyst, relative to thioester of Formula I, is used. In some embodiments, about 7.5% (w/w) of palladium on carbon catalyst, relative to thioester of Formula I, is used. In some embodiments, about 10% (w/w) of palladium on carbon catalyst, relative to thioester of Formula I, is used.

In some embodiments, the palladium on carbon is an eggshell catalyst. In some embodiments, the palladium on carbon is an unreduced eggshell catalyst. In some embodiments, the palladium on carbon is a completely reduced eggshell catalyst. In some embodiments, about 5% (w/w) of eggshell catalyst, relative to thioester of Formula I, is used. In some embodiments, about 10% (w/w) of eggshell catalyst, relative to thioester of Formula I, is used.

In some embodiments, the reduction further comprises a Pd(II) catalyst. In some embodiments, the Pd(II) catalyst is Pd(OH)$_2$. In some embodiments, the Pd(II) catalyst is Pd(OAc)$_2$.

In certain embodiments, the reduction of the thioester compound of Formula I is carried out in a solvent selected from glacial acetic acid, tetrahydrofuran, dichloromethane, and acetone. In certain embodiments, the reduction of the thioester compound of Formula I is carried out in a co-solvent mixture of glacial acetic acid and tetrahydrofuran.

In some embodiments, the reduction step further utilizes glacial acetic acid. In some embodiments, at least 0.5 equivalents of glacial acetic acid, relative to I*HX, is used. In some embodiments, at least 1.0 equivalents of glacial acetic acid, relative to I*HX, is used. In some embodiments, at least 1.1 equivalents of glacial acetic acid, relative to I*HX, is used. In some embodiments, at least 1.2 equivalents of glacial acetic acid, relative to I*HX, is used.

In certain embodiments, the reduction of the thioester compound of Formula I comprises adding triethylsilane to a mixture of Compound 5 and palladium on carbon in tetrahydrofuran and glacial acetic acid.

In certain embodiments, the reduction of the thioester compound of Formula I comprises adding triethylsilane to a mixture of Compound 5 and palladium on carbon in tetrahydrofuran and glacial acetic acid, wherein said mixture has been cooled to 5±5° C.

In certain embodiments the triethylsilane is added over at least 30 minutes.

In certain embodiments, the reduction of the thioester compound of Formula I further comprises allowing the reaction mixture to warm to about 20° C. over about 1.5 hours following the addition of triethylsilane.

In certain embodiments, the reduction of the thioester compound of Formula I further comprises stirring the reaction mixture at 15±5° C. for at least 3 hrs.

In certain embodiments, the reduction of the thioester compound of Formula I further comprises the steps of:
1) stirring the reaction mixture until Compound 5 is present at less than 5 area % by HPLC analysis;
2) filtering and concentrating the resulting mixture.

In certain embodiments, the HPLC method used to determine the area % of Compound 5 in the reaction mixture is Test Method TM.04760, as disclosed herein.

In some embodiments, III is obtained as a solid. In some embodiments, solid III is obtained from a solvent comprising one or more of EtOAc, MTBE, and heptane. In some embodiments, solid III is obtained from a solvent consisting of EtOAc, MTBE, and heptane. In some embodiments, solid III is obtained by adding a solution of III in EtOAc to a mixture of MTBE and heptane. In some embodiments, solid III is obtained by adding a solution of III in EtOAc to a 1:1 (v:v) mixture of MTBE and heptane.

Also provided are methods for preparing a compound of Formula III from an acid salt of thioester of Formula I, designated I*HX, comprising: 1) a free base step, comprising reaction of the salt I*HX with a base, to form the corresponding free base I, and 2) a reduction step, comprising a method for reducing a thioester of Formula I to provide a compound of Formula III, as disclosed herein.

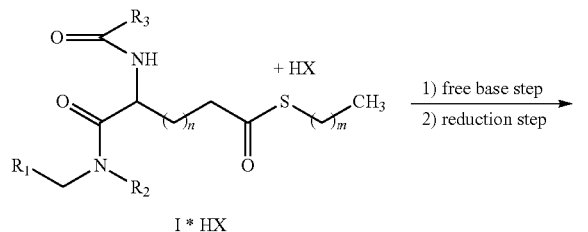

I * HX 1) free base step
2) reduction step

-continued

III

In some embodiments, the free base step is performed in a solvent mixture comprising MTBE and H$_2$O. In some embodiments, Na$_2$CO$_3$ is used in the free base step. In some embodiments, free base I is obtained as a solid. In some embodiments, free base I is obtained as a solid by addition of n-heptane to a solution of free base I in MTBE and H$_2$O. In some embodiments, solid free base I is washed with n-heptane.

In some embodiments, the compound of Formula I*HX is Compound 5*HCl.

5 * HCl

+ HCl

Also provided are methods for preparing thioesters of Formula I, comprising reacting a carboxylic acid compound of Formula V with a thiol compound of Formula VI:

V

VI

I wherein:
n is 1 or 2;
m is 0-12;

R¹ and R² together with the nitrogen to which they attach, form a nitrogen-containing heterocycloalkyl or heteroaryl ring, which may be optionally substituted with between 0 and 3 R⁶ groups; and R³ is phenyl substituted with halogen, cyano, or heteroaryl;

wherein R⁶ is as defined above;

with an appropriate coupling agent.

In certain embodiments, R¹ and R² are taken together to form a nitrogen-containing heterocycloalkyl, which may be optionally substituted with between 0 and 3 R⁶ groups.

In certain embodiments the nitrogen-containing heterocycloalkyl is chosen from:

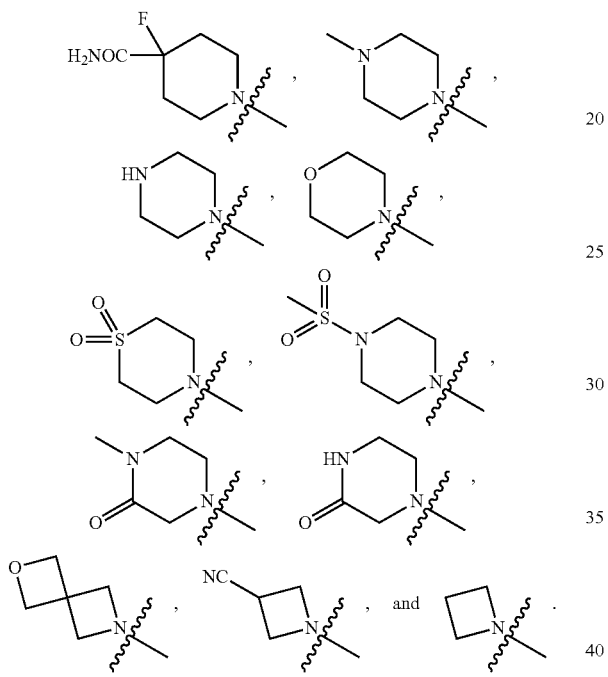

In certain embodiments, the nitrogen-containing heterocycloalkyl is:

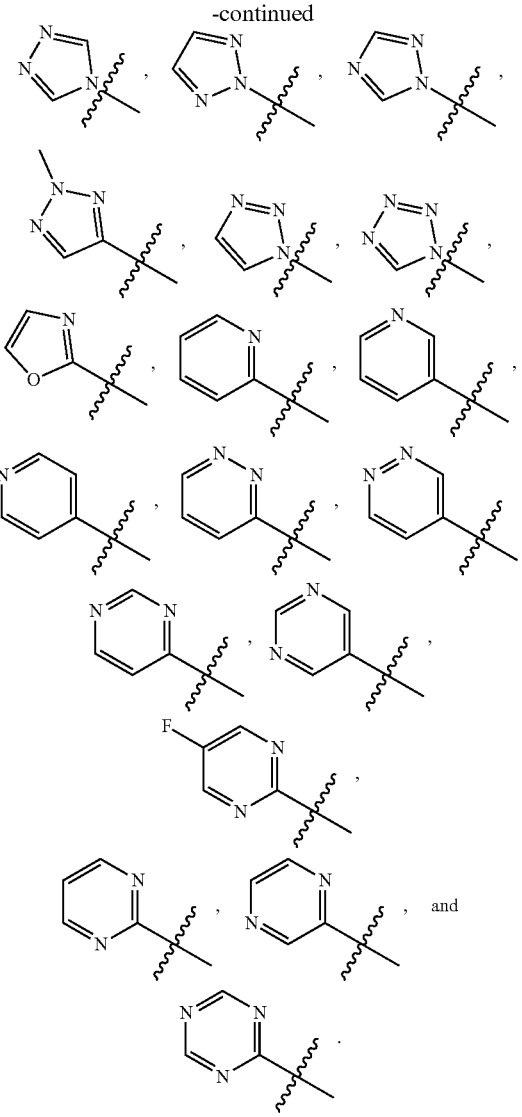

In certain embodiments, R³ is phenyl substituted with

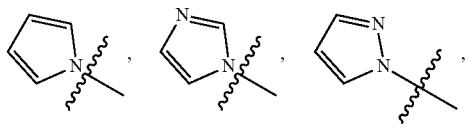

In certain embodiments, n is 1.

In certain embodiments, m is 11.

Coupling agents for condensing carboxylate groups with amines, alcohols and thiols to provide amides, esters and thioesters are well known to those skilled in the art of organic synthesis. Examples may be found in: Montalbetti and Falque, *Tetrahedron* 2005, 61, 10827-10852; T. M. Vishwanatha, M. Samarasimhareddy, V. V. Sureshbabu, *Synlett*, 2012, 23, 89-92; B. Neises, W. Steglich, *Angew. Chem. Int. Ed.*, 1978, 17, 522-524, and elsewhere.

In certain embodiments, the coupling agent for the reaction of the compound is 1-ethyl-3-(3-dimethylaminopropyl) carbodiimide (EDCI), or a salt thereof. In some embodiments, the coupling agent is the hydrochloride salt of EDCI.

In certain embodiments, the nitrogen-containing heterocycloalkyl is optionally substituted with between 0 and 3 R⁶ groups chosen from alkyl and oxo.

In certain embodiments, R³ is phenyl substituted with heteroaryl.

In certain embodiments, R³ is phenyl substituted with heteroaryl selected from the group consisting of:

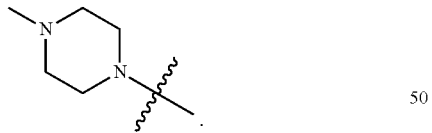

In some embodiments, at most 1.5 equivalents of EDCI, relative to V, is used. In some embodiments, at most 1.2 equivalents of EDCI, relative to V, is used. In some embodiments, at most 1.1 equivalents of EDCI, relative to V, is used.

In some embodiments, the reaction between the compound of Formula V and the compound of Formula VI further comprises 4-dimethylaminopyridine (DMAP). In some embodiments, DMAP is present in a catalytic amount. In some embodiments, at most 0.2 equivalents of DMAP, relative to V, is used. In some embodiments, at most 0.1 equivalents of DMAP, relative to V, is used. In some embodiments, at most 0.05 equivalents of DMAP, relative to V, is used.

In some embodiments, the reaction between the compound of Formula V and the compound of Formula VI is carried out in a halogenated aliphatic solvent. In some embodiments, the reaction is carried out in DCM.

Also provided are methods for preparing acid salts of thioesters of Formula I, comprising 1) a thioester formation step, comprising a method for synthesis of a thioester of Formula I, as disclosed herein, and 2) a salt formation step, comprising reaction with acid HX, to form the corresponding salt of Formula I, designated I*HX:

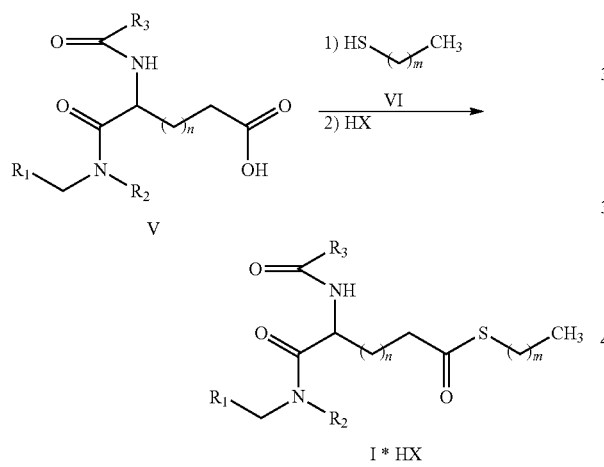

In certain embodiments, the thioester formation step is followed directly by the salt formation step. In certain embodiments, the thioester of Formula I formed in the thioester formation step is carried directly to the salt formation step without isolation of the thioester of Formula I.

In some embodiments, the thioester formation step is performed in solution. In some embodiments, the thioester formation step is performed in DCM solution. In some embodiments, the solution is reduced in volume before the salt formation step.

In some embodiments, the salt formation step is performed in a solvent comprising one or more of: ethanol and acetonitrile. In some embodiments, the salt formation step is performed in a solvent consisting of ethanol and acetonitrile.

In some embodiments, the nitrogen-containing heterocycloalkyl or heteroaryl ring comprises a basic nitrogen.

In some embodiments, the nitrogen-containing heterocycloalkyl or heteroaryl ring is piperidine, which may be optionally substituted with between 0 and 3 $R^6$ groups.

In some embodiments, m in Formula VI is 11.

In some embodiments, the acid HX is a mineral acid.

In some embodiments, the mineral acid is HCl. In some embodiments, the mineral acid is added to the reaction mixture as an ethanolic solution.

In some embodiments, I*HX is a solid.

In some embodiments, I*HX is obtained from the reaction mixture by filtration. In some embodiments, the solid I*HX is washed with acetonitrile.

Also provided are methods for preparing a compound of Formula V wherein n is 1 (compounds of Formula XII) from glutamic acid, comprising the steps:

a. reacting a protected glutamate ester VII with an appropriate heterocycle VIII to provide a compound of Formula IX:

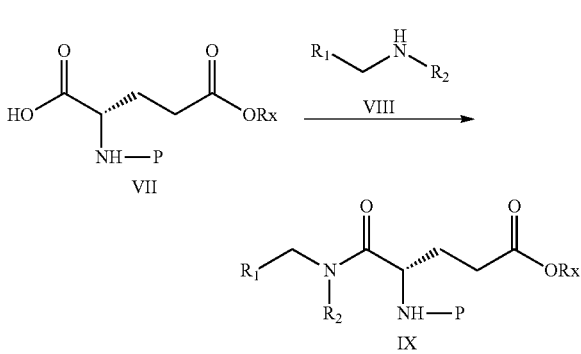

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

b. removing the protecting group from the glutamate amino group of the compound of Formula IX to provide a compound of Formula X:

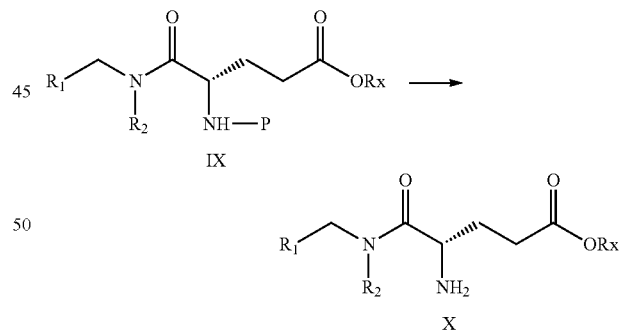

c. reacting the compound of Formula X with an appropriate substituted benzoic acid to provide a compound of Formula XI:

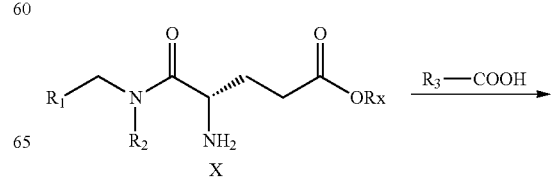

-continued

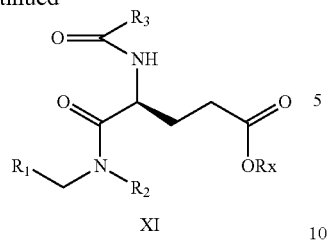

XI wherein:
R³ is phenyl substituted with halogen, cyano, or heteroaryl;
and
d. converting the ester group of the compound of Formula XI to a carboxylic acid to provide a compound of Formula XII:

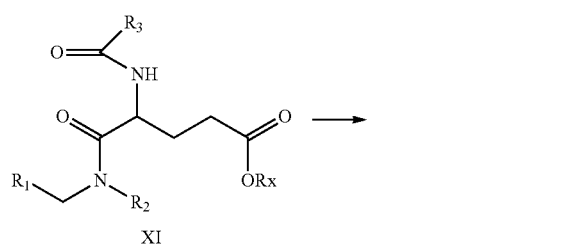

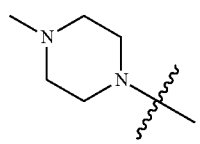

XII

In certain embodiments, Rx is methyl.

Monovalent nitrogen protecting groups suitable for use as P in the present invention are well known to those skilled in the art of organic synthesis, and are described for example in T. W. Green, P. G. M. Wuts, *Protective Groups in Organic Synthesis*, Wiley-Interscience, New York, 1999, pp. 503-507, 518-525, 531-537, 550-558, 564-566, 579-580, 583-584, 586-590, 604-607, 736-747, and elsewhere. In certain embodiments, P is tert-butoxycarbonyl (Boc).

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

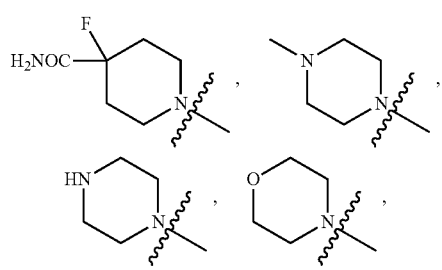

-continued

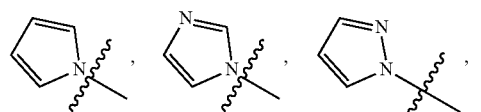

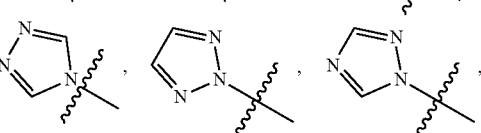

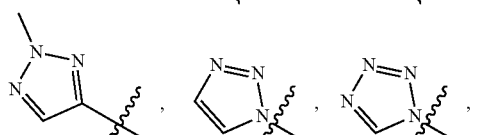

In certain embodiments, the nitrogen-containing heterocycloalkyl is:

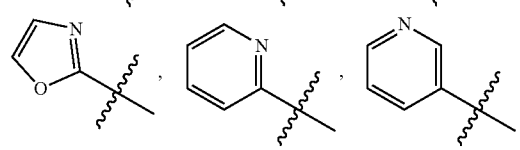

In certain embodiments, the nitrogen-containing heterocycloalkyl is optionally substituted with between 0 and 3 $R^6$ groups chosen from alkyl and oxo.

In certain embodiments, $R^3$ is phenyl substituted with heteroaryl.

In certain embodiments, $R^3$ is phenyl substituted with heteroaryl selected from the group consisting of:

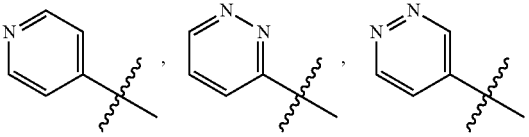

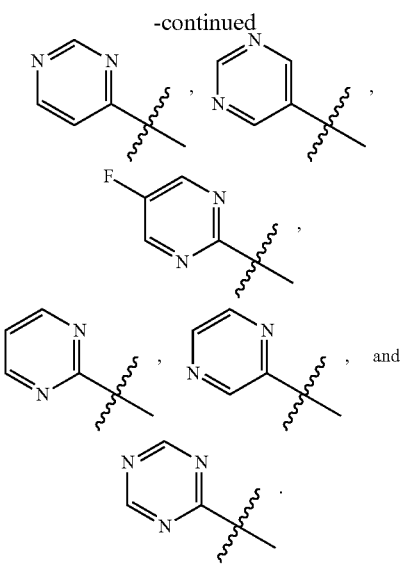

In certain embodiments, $R^3$ is phenyl substituted with

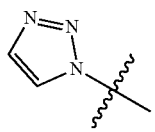

In certain embodiments, the reaction of a carboxylic acid of Formula VII with a heterocycle of Formula VIII is performed by first treating the compound of Formula VII with 4-methylmorpholine and pivaloyl chloride in a solvent.

In certain embodiments, 4-methylmorpholine and pivaloyl chloride are present in equimolar amounts relative to the compound of Formula VII.

In certain embodiments, the solvent is IPA. In certain embodiments, IPA is used in the amount of 10 volumes relative to the compound of Formula VII.

In certain embodiments, the mixture of the compound of Formula VII, pivaloyl chloride, and 4-methylmorpholine is stirred in IPA for 2 hrs at −5-5° C. before adding the heterocycle of Formula VIII. In certain embodiments, the mixture of the compound of Formula VII, pivaloyl chloride, 4-methylmorpholine, and heterocycle of Formula VIII in IPA is stirred at 0-5° C. for 1 hour before quenching with aqueous 5% NaHCO₃.

Removal of the nitrogen protecting group may be done using reaction condition appropriate for the particular protecting group. Such conditions are known to those of skill in the art of organic synthesis, and may be found for example in the cited pages from Green et al., cited previously herein.

In certain embodiments, the removal of the nitrogen protecting group from the compound of Formula IX is done under acidic conditions. In certain embodiments, the acidic conditions comprise adding 1.5 M HCl in ethyl acetate (EtOAc) to an EtOAc solution of the compound of Formula IX.

In certain embodiments, the EtOAc solution of the compound of Formula IX is cooled to 0-5° C. before adding 1.5 M HCl in ethyl acetate (EtOAc). In certain embodiments, the reaction mixture is stirred for at least 12 hours after adding the HCl solution. In certain embodiments, HCl gas is passed through the reaction mixture to complete the removal of the nitrogen protecting group.

In certain embodiments, the removal of the nitrogen protecting group from the compound of Formula IX is done in a solvent comprising one or more of: sulfolane and dioxane. In certain embodiments, the solvent comprises both sulfolane and dioxane. In certain embodiments, the compound of formula X is obtained as a solid. In certain embodiments, solid compound of formula X is obtained by adding a solution of the compound into a quantity of methyl tert-butyl ether (MTBE). In certain embodiments, the compound of formula X is washed with MTBE.

Coupling agents for condensing carboxylate groups with amines, alcohols and thiols to provide amides, esters and thioesters are well known to those skilled in the art of organic synthesis, as noted previously. Examples of suitable reagents and methods may be found, for example, in the literature references previously cited herein. Such coupling agents and conditions may be used to couple substituted benzoic acids with compounds of Formula X to provide compounds of Formula XI.

In certain embodiments, the reaction of the compound of Formula X with a substituted benzoic acid is performed using 1-ethyl-3-(3-dimethylaminopropyl)carbodiimide hydrochloride (EDC) together with hydroxybenzotriazole (HOBt).

In certain embodiments, the coupling reaction to furnish the compound of Formula XI is performed in THF as the solvent. In certain embodiments, 13 volumes of THF are used relative to the compound of Formula X.

In certain embodiments, the coupling reaction to furnish the compound of Formula XI is performed in DCM as the solvent. In certain embodiments, 25 volumes of DCM are used relative to the compound of Formula X.

In certain embodiments, 4-methylmorpholine is added to the solution of the compound of Formula X in THF before adding the substituted benzoic acid, EDC and HOBt.

In certain embodiments, 4-methylmorpholine is added to the solution of the compound of Formula X in THF and the resulting solution is cooled to below 10° C. before adding the substituted benzoic acid. In certain embodiments, the solution is stirred at below 10° C. for about 30 minutes. In certain embodiments, EDC and HOBt are added to the stirred solution at below 10° C. after adding 4-methylmorpholine and the substituted benzoic acid and stirring.

In certain embodiments, the mixture of EDC, HOBt, substituted benzoic acid, and compound of Formula X is stirred at 10-20° C. for at least 15 hrs.

In certain embodiments, the isolation of the compound of Formula XI comprises the steps of:
 a. diluting the reaction mixture with ethyl acetate;
 b. adding sufficient 6 M NaOH aqueous solution to adjust the pH to 9-10;
 c. adding 0.5 w/w of sodium chloride;
 d. separating the phases and extracting the aqueous layer with EtOAc; and
 e. drying and concentrating the combined organic layers.

In certain embodiments, the isolation of the compound of Formula X comprises the steps of:
 a. adding sufficient 10 wt % Na₂CO₃ aqueous solution to adjust the pH to 9-10;
 b. adding aqueous NaCl;
 c. adding IPAc;
 d. adding n-heptane;
 e. removing the solid that is formed; and
 f. washing the solid with n-heptane.

Hydrolysis of the Rx ester moiety of the compound of Formula XI to provide the carboxylate of Formula XII may be done by standard methods for the hydrolysis of esters as are well known to those of skill in organic synthesis.

In certain embodiments, hydrolysis of the compound of Formula XI to provide the compound of Formula XII is done under base conditions.

In certain embodiments, the hydrolysis of the compound of Formula XI is done in a solvent comprising a lower carbinol. In some embodiments the lower carbinol is methanol. In some embodiments, the solvent for the hydrolysis comprises methanol and THF.

In certain embodiments the hydrolysis of the compound of Formula XI comprises adding 1 M NaOH aqueous solution to a solution of the compound of Formula XI in THF and methanol which has been cooled to −10° C.

In some embodiments, THF and methanol are each present in the amount of about 2.2 volumes relative to the compound of Formula XI.

In some embodiments, 1 M NaOH aqueous solution is added to the solution of the compound of Formula XI in THF and methanol while keeping the temperature below 10° C. In some embodiments the reaction mixture is stirred for about 6 hrs below 10° C. after adding the 1 M NaOH.

In certain embodiments, the isolation of the compound of Formula XII comprises the steps of:
  a. diluting the reaction mixture with heptanes;
  b. separating the phases and treating the aqueous phase with AMBERLITE® IR120 to adjust the pH to 6.3;
  c. stirring the aqueous phase for 30 minutes;
  d. filtering the aqueous phase and washing the filter cake with THF; and
  e. concentrating the filtrate to obtain the compound of Formula XII.

In certain embodiments, hydrolysis of the compound of Formula XI to provide the compound of Formula XII is done in substantially anhydrous conditions.

In certain embodiments, hydrolysis of the compound of Formula XI to provide the compound of Formula XII is done with Me₃SiOK.

In certain embodiments, hydrolysis of the compound of Formula XI to provide the compound of Formula XII is done in tetrahydrofuran.

In certain embodiments, the compound of Formula XII is obtained as a solid. In certain embodiments, the compound of Formula XII is obtained from a solvent comprising one or more of: MeOH and CH₃CN. In certain embodiments, the compound of Formula XII is obtained from a solvent consisting of MeOH and CH₃CN. In certain embodiments, the compound of Formula XII is obtained from a solvent consisting of a 1:2 (v:v) mixture of MeOH and CH₃CN.

Also provided is a process for preparing the bis-tosylate salt (Compound 8) of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 7), comprising:

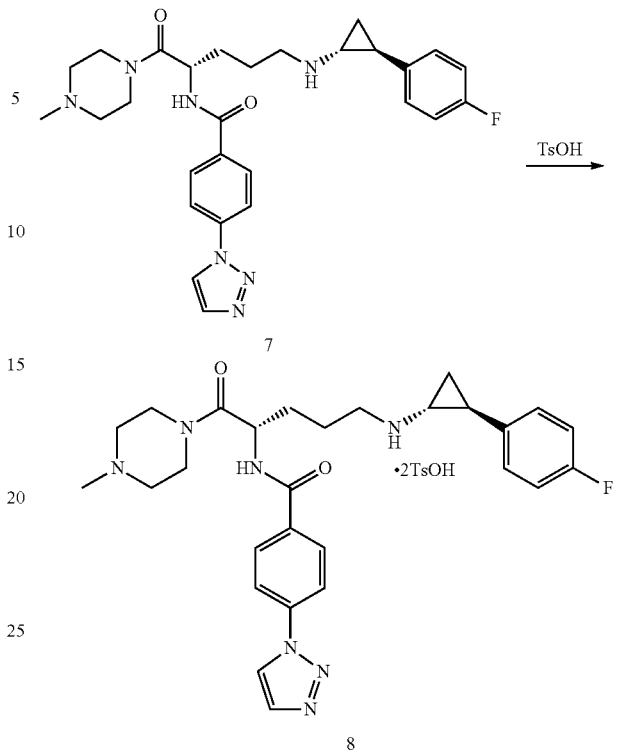

adding a solution of p-toluenesulfonic acid hydrate in THF to a stirred solution of Compound 7 in THF and IPA.

In certain embodiments the reaction mixture temperature is 25±5° C.

In certain embodiments 2.5 equivalents of p-toluenesulfonic acid hydrate relative to Compound 7 are added to the solution of Compound 7 in THF and IPA.

In certain embodiments the total volume of THF and IPA combined is about 12 volumes.

In certain embodiments the mixture of Compound 7 and p-toluenesulfonic acid hydrate in THF and IPA is stirred for at least 15 hours.

In certain embodiments the process for preparing the bis-tosylate salt (Compound 8) of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 7) further comprises the steps of:
  a. filtering the reaction mixture; and
  b. washing the filter cake with IPA; and
  c. drying the filter cake at 35±5° C. under vacuum for at least 15 hours.

In certain embodiments about 4 volumes of IPA are used to wash the filter cake.

In certain embodiments the process for preparing the bis-tosylate salt (Compound 8) of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 2) further comprises recrystallizing the filter cake from methanol.

In certain embodiments between about 10 and about 20 volumes of methanol relative to the filter cake are used for the recrystallization.

In certain embodiments the process for preparing the bis-tosylate salt (Compound 8) of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 2) further comprises the step of recrystallizing the filter cake from a mixture of methanol and ethyl acetate.

In certain embodiments about 5 volumes of methanol and about 5 volumes of ethyl acetate relative to the filter cake are used for the recrystallization.

In certain embodiments the mixture of the filter cake in methanol and acetate is heated to 50±5° C. and stirred for at least 3 hrs.

Certain embodiments further comprise cooling the mixture to 25±5° C. and stirring for at least 3 hrs before filtering.

Also provided are methods for preparing a compound of Formula IV wherein n is 1 (compounds of Formula XVI) from glutamic acid, comprising the steps:

a. reacting a protected glutamate ester VII with an appropriate heterocycle VIII to provide a compound of Formula IX:

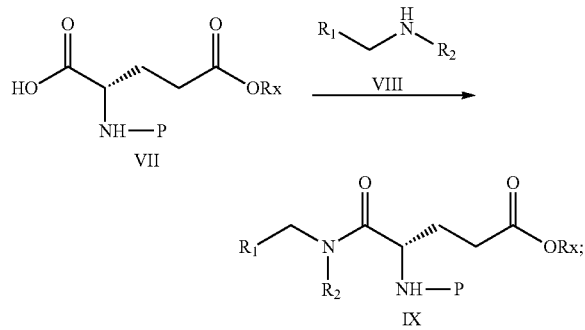

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;
wherein $R^6$ is as defined above;

b. removing the protecting group from the glutamate amino group of the compound of Formula IX to provide a compound of Formula X:

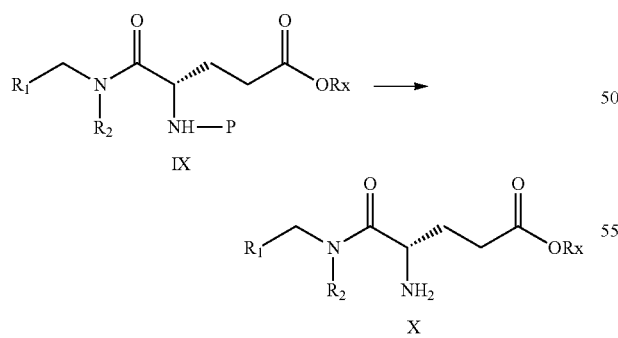

wherein:
P is a monovalent nitrogen protecting group;
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups;

wherein $R^6$ is as defined above;

c. reacting the compound of Formula X with an appropriate substituted benzoic acid to provide a compound of Formula XI:

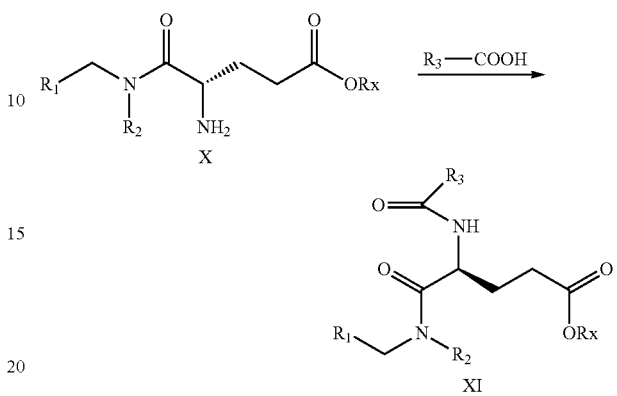

wherein:
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;

d. converting the ester group of the compound of Formula XI to a carboxylic acid to provide a compound of Formula XII:

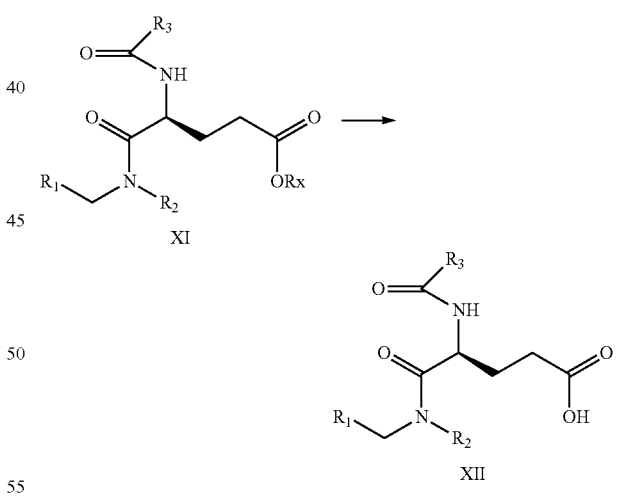

wherein:
Rx is an alkyl group; and
$R^1$ and $R^2$ together with the nitrogen to which they attach, form a nitrogen-containing heterocycloalkyl or heteroaryl ring, which may be optionally substituted with between 0 and 3 $R^6$ groups; and
$R^3$ is phenyl substituted with halogen, cyano, or heteroaryl;
wherein $R^6$ is as defined above;

e. converting the compound of Formula XII to the compound of Formula XIII, comprising 1) a thioester formation step, comprising reaction with the compound of Formula VI, and 2) a salt formation step, comprising reaction with HX:

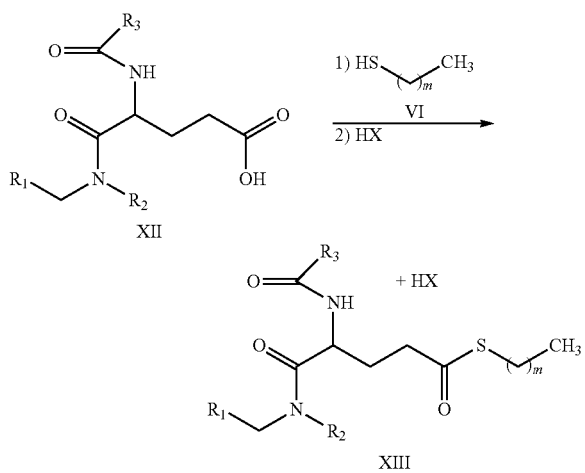

wherein:
m is 0-12;
R$^1$ and R$^2$ together with the nitrogen to which they attach, form a nitrogen-containing heterocycloalkyl or heteroaryl ring, which may be optionally substituted with between 0 and 3 R$^6$ groups;
R$^3$ is phenyl substituted with halogen, cyano, or heteroaryl; and
wherein R$^6$ is as defined above;

f. converting the compound of Formula XIII to the compound of formula XIV, comprising: 1) a free base step, comprising reaction of the salt XIII with a base, and 2) a reduction step:

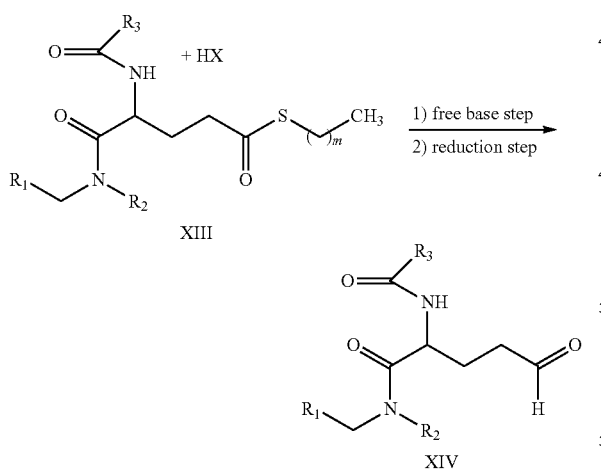

wherein:
m is 0-12;
R$^1$ and R$^2$ together with the nitrogen to which they attach, form a nitrogen-containing heterocycloalkyl or heteroaryl ring, which may be optionally substituted with between 0 and 3 R$^6$ groups;
R$^3$ is phenyl substituted with halogen, cyano, or heteroaryl; and
wherein R$^6$ is as defined above;

g. converting the compound of Formula XIV to the compound of Formula XV, by reaction with a compound of Formula II under reductive amination conditions:

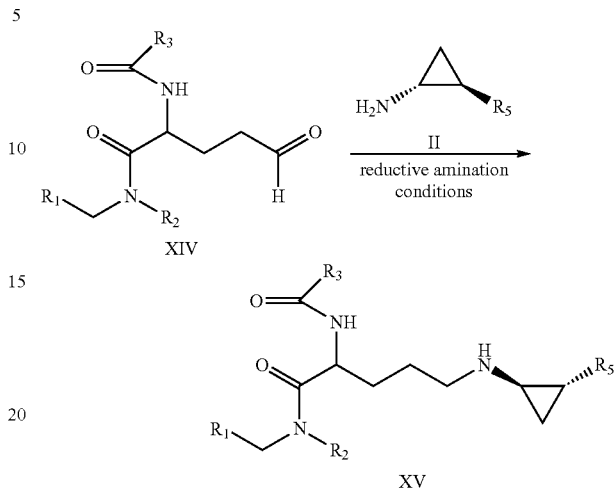

wherein:
R$^1$ and R$^2$ together with the nitrogen to which they attach, form a nitrogen-containing heterocycloalkyl or heteroaryl ring, which may be optionally substituted with between 0 and 3 R$^6$ groups; and
R$^3$ is phenyl substituted with halogen, cyano, or heteroaryl;
R$^5$ is chosen from aryl and heteroaryl, any of which may be optionally substituted
with between 0 and 3 R$^6$ groups;
wherein R$^6$ is defined as above;
and
h. converting the compound of Formula XV to the compound of Formula XVI, by reaction with an acid compound HX:

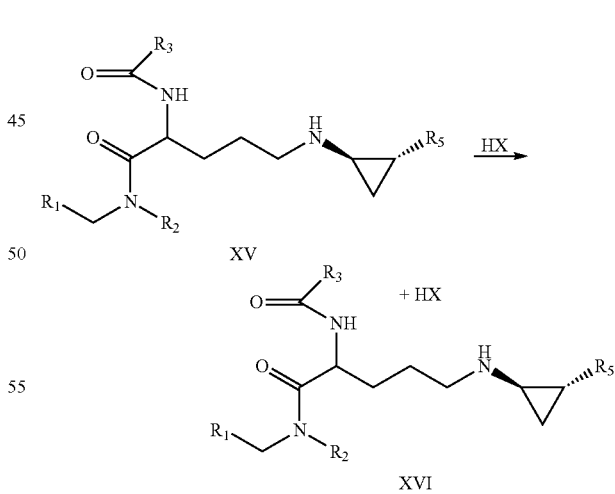

wherein:
R$^1$ and R$^2$ together with the nitrogen to which they attach, form a nitrogen-containing heterocycloalkyl or heteroaryl ring, which may be optionally substituted with between 0 and 3 R$^6$ groups; and
R$^3$ is phenyl substituted with halogen, cyano, or heteroaryl;

$R^5$ is chosen from aryl and heteroaryl, any of which may be optionally substituted with between 0 and 3 $R^6$ groups;
wherein $R^6$ is as defined above.

In certain embodiments, Rx is methyl.

In certain embodiments, the monovalent nitrogen protecting group is a carbamate protecting group.

In certain embodiments, the carbamate protecting group is chosen from Boc, CBz, and Fmoc.

In certain embodiments, the carbamate protecting group is Boc.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

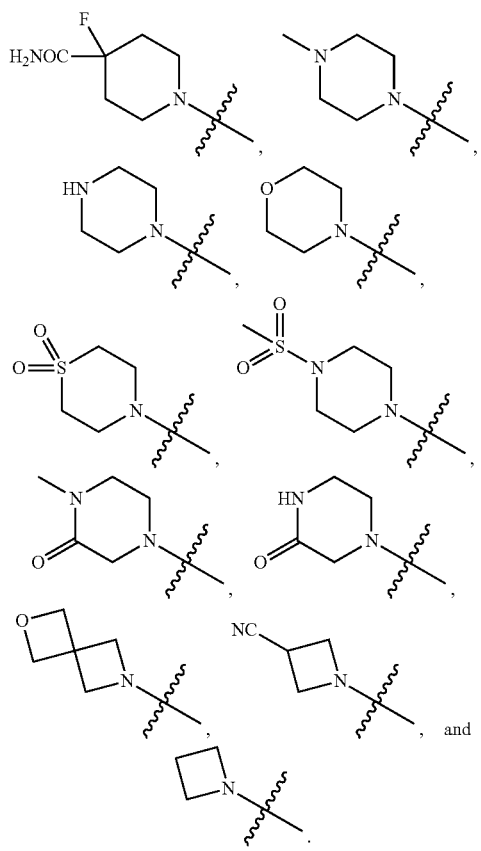

In certain embodiments, the nitrogen-containing heterocycloalkyl is:

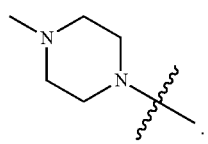 [SMILES: *N1CCN(C)CC1]

In certain embodiments, the nitrogen-containing heterocycloalkyl is optionally substituted with between 0 and 3 $R^6$ groups chosen from alkyl and oxo.

In certain embodiments, $R^3$ is phenyl substituted with heteroaryl.

In certain embodiments, $R^3$ is phenyl substituted with heteroaryl selected from the group consisting of:

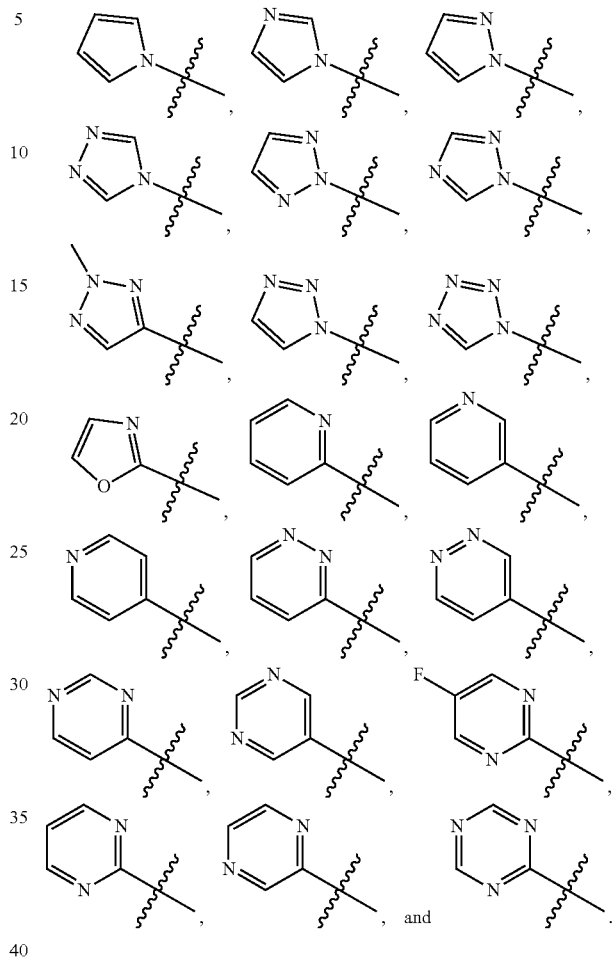

In certain embodiments, $R^3$ is phenyl substituted with

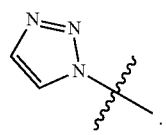

In certain embodiments, the reaction of a carboxylic acid of Formula VII with a heterocycle of Formula VIII is performed by first treating the compound of Formula VII with 4-methylmorpholine and pivaloyl chloride in a solvent.

In certain embodiments, 4-methylmorpholine and pivaloyl chloride are present in equimolar amounts relative to the compound of Formula VII.

In certain embodiments, the solvent is IPA. In certain embodiments, IPA is used in the amount of 10 volumes relative to the compound of Formula VII.

Removal of the nitrogen protecting group may be done using reaction condition appropriate for the particular protecting group. Such conditions are known to those of skill in the art of organic synthesis, and may be found for example in the cited pages from Green et al., cited previously herein.

In certain embodiments, the removal of the nitrogen protecting group from the compound of Formula IX is done under acidic conditions. In certain embodiments, the acidic conditions comprise adding 1.5 M HCl in ethyl acetate (EtOAc) to an EtOAc solution of the compound of Formula IX.

In certain embodiments, the removal of the nitrogen protecting group from the compound of Formula IX is done in a solvent comprising one or more of: sulfolane and dioxane. In certain embodiments, the solvent comprises both sulfolane and dioxane. In certain embodiments, the compound of formula X is obtained as a solid. In certain embodiments, solid compound of formula X is obtained by adding a solution of the compound into a quantity of methyl tert-butyl ether (MTBE). In certain embodiments, the compound of formula X is washed with MTBE.

In certain embodiments, the reaction of the compound of Formula X with a substituted benzoic acid is performed using 1-ethyl-3-(3-dimethylaminopropyl)carbodiimide hydrochloride (EDC) together with hydroxybenzotriazole (HOBt).

In certain embodiments, the coupling reaction to furnish the compound of Formula XI is performed in THF as the solvent. In certain embodiments, 13 volumes of THF are used relative to the compound of Formula X.

In certain embodiments, the coupling reaction to furnish the compound of Formula XI is performed in DCM as the solvent. In certain embodiments, 25 volumes of DCM are used relative to the compound of Formula X.

In certain embodiments, 4-methylmorpholine is added to the solution of the compound of Formula X in THF before adding the substituted benzoic acid, EDC and HOBt.

In certain embodiments, 4-methylmorpholine is added to the solution of the compound of Formula X in THF and the resulting solution is cooled to below 10° C. before adding the substituted benzoic acid. In certain embodiments, the solution is stirred at below 10° C. for about 30 minutes. In certain embodiments, EDC and HOBt are added to the stirred solution at below 10° C. after adding 4-methylmorpholine and the substituted benzoic acid and stirring.

In certain embodiments, the mixture of EDC, HOBt, substituted benzoic acid, and compound of Formula X is stirred at 10-20° C. for at least 15 hrs.

In certain embodiments, the isolation of the compound of Formula XI comprises the steps of:
a. adding sufficient 10 wt % $Na_2CO_3$ aqueous solution to adjust the pH to 9-10;
b. adding aqueous NaCl;
c. adding IPAc;
d. adding n-heptane;
e. removing the solid that is formed; and
f. washing the solid with n-heptane.

Hydrolysis of the Rx ester moiety of the compound of Formula XI to provide the carboxylate of Formula XII may be done by standard methods for the hydrolysis of esters as are well known to those of skill in organic synthesis.

In certain embodiments, hydrolysis of the compound of Formula XI to provide the compound of Formula XII is done under base conditions.

In certain embodiments, hydrolysis of the compound of Formula XI to provide the compound of Formula XII is done in substantially anhydrous conditions.

In certain embodiments, hydrolysis of the compound of Formula XI to provide the compound of Formula XII is done with $Me_3SiOK$.

In certain embodiments, hydrolysis of the compound of Formula XI to provide the compound of Formula XII is done in tetrahydrofuran.

In certain embodiments, the compound of Formula XII is obtained as a solid. In certain embodiments, the compound of Formula XII is obtained from a solvent comprising one or more of: MeOH and $CH_3CN$. In certain embodiments, the compound of Formula XII is obtained from a solvent consisting of MeOH and $CH_3CN$. In certain embodiments, the compound of Formula XII is obtained from a solvent consisting of a 1:2 (v:v) mixture of MeOH and $CH_3CN$.

In certain embodiments, the coupling agent for the reaction of the compound of Formula XII is 1-ethyl-3-(3-dimethylaminopropyl)carbodiimide (EDCI), or a salt thereof. In some embodiments, the coupling agent is the hydrochloride salt of EDCI. In some embodiments, at most 1.5 equivalents of EDCI, relative to XII, is used. In some embodiments, at most 1.2 equivalents of EDCI, relative to XII, is used. In some embodiments, at most 1.1 equivalents of EDCI, relative to XII, is used.

In some embodiments, the reaction between the compound of Formula XII and the compound of Formula VI further comprises 4-dimethylaminopyridine (DMAP). In some embodiments, DMAP is present in a catalytic amount. In some embodiments, at most 0.2 equivalents of DMAP, relative to V, is used. In some embodiments, at most 0.1 equivalents of DMAP, relative to V, is used. In some embodiments, at most 0.05 equivalents of DMAP, relative to V, is used.

In some embodiments, the reaction between the compound of Formula XII and the compound of Formula VI is carried out in a halogenated aliphatic solvent. In some embodiments, the reaction is carried out in DCM.

In some embodiments, the free base step is performed in a solvent mixture comprising MTBE and $H_2O$. In some embodiments, $Na_2CO_3$ is used in the free base step. In some embodiments, free base XIII is obtained as a solid. In some embodiments, free base XIII is obtained as a solid by addition of n-heptane to a solution of free base I in MTBE and $H_2O$. In some embodiments, solid free base XIII is washed with n-heptane.

In some embodiments, the reduction of the thioester compound of Formula XIII utilizes a silane reducing agent. In some embodiments, the silane reducing agent is triethylsilane. In some embodiments, 4.0 equivalents of triethylsilane, relative to thioester of Formula I, is used.

In some embodiments, the reduction further comprises palladium on carbon. In certain embodiments, the reduction may be carried out as described by Fukuyama et al.: H. Tokuyama, S. Yokoshima, S.-C. Lin, L. Li, T. Fukuyama, *Synthesis*, 2002, 1121-1123.

In some embodiments, the reduction further comprises a Pd(0) catalyst. In some embodiments, the Pd(0) catalyst is palladium on carbon. In some embodiments, the palladium on carbon is anhydrous. In some embodiments, about 2.5% (w/w) of palladium on carbon catalyst, relative to thioester of Formula XIII, is used. In some embodiments, about 5% (w/w) of palladium on carbon catalyst, relative to thioester of Formula XIII, is used. In some embodiments, about 7.5% (w/w) of palladium on carbon catalyst, relative to thioester of Formula XIII, is used. In some embodiments, about 10% (w/w) of palladium on carbon catalyst, relative to thioester of Formula XIII, is used.

In some embodiments, the palladium on carbon is an eggshell catalyst. In some embodiments, the palladium on carbon is an unreduced eggshell catalyst. In some embodiments, the palladium on carbon is a completely reduced eggshell catalyst. In some embodiments, about 5% (w/w) of eggshell catalyst, relative to thioester of Formula I, is used.

In some embodiments, about 10% (w/w) of eggshell catalyst, relative to thioester of Formula I, is used.

In some embodiments, the reduction further comprises a Pd(II) catalyst. In some embodiments, the Pd(II) catalyst is Pd(OH)$_2$. In some embodiments, the Pd(II) catalyst is Pd(OAc)$_2$.

In certain embodiments, the reduction of the thioester compound of Formula XIII is carried out in a solvent selected from glacial acetic acid, tetrahydrofuran, dichloromethane, and acetone. In certain embodiments, the reduction of the thioester compound of Formula XIII is carried out in a co-solvent mixture of glacial acetic acid and tetrahydrofuran.

In some embodiments, the reduction step further utilizes glacial acetic acid. In some embodiments, at least 0.5 equivalents of glacial acetic acid, relative to XIII, is used. In some embodiments, at least 1.0 equivalents of glacial acetic acid, relative to XIII, is used. In some embodiments, at least 1.1 equivalents of glacial acetic acid, relative to XIII, is used. In some embodiments, at least 1.2 equivalents of glacial acetic acid, relative to XIII, is used.

In certain embodiments, the reduction of the thioester compound of Formula XIII comprises adding triethylsilane to a mixture of the thioester compound of Formula XIII and palladium on carbon in tetrahydrofuran and glacial acetic acid.

In certain embodiments, the reduction of the thioester compound of Formula XIII comprises adding triethylsilane to a mixture of the thioester compound of Formula XIII and palladium on carbon in tetrahydrofuran and glacial acetic acid, wherein said mixture has been cooled to 5±5° C.

In certain embodiments the triethylsilane is added over at least 30 minutes.

In certain embodiments, the reduction of the thioester compound of Formula XIII further comprises allowing the reaction mixture to warm to about 20° C. over about 1.5 hours following the addition of triethylsilane.

In certain embodiments, the reduction of the thioester compound of Formula XIII further comprises stirring the reaction mixture at 15±5° C. for at least 3 hrs.

In certain embodiments, the reduction of the thioester compound of Formula XIII further comprises the steps of:
1) stirring the reaction mixture until the thioester compound of Formula XIII is present at less than 5 area % by HPLC analysis;
2) filtering and concentrating the resulting mixture.

In some embodiments, the compound of formula XIV is obtained as a solid. In some embodiments, the solid compound of formula XIV is obtained from a solvent comprising one or more of EtOAc, MTBE, and heptane. In some embodiments, the solid compound of formula XIV is obtained from a solvent consisting of EtOAc, MTBE, and heptane. In some embodiments, the solid compound of formula XIV is obtained by adding a solution of the compound of formula XIV in EtOAc to a mixture of MTBE and heptane. In some embodiments, the solid compound of formula XIV is obtained by adding a solution of the compound of formula XIV in EtOAc to a 1:1 (v:v) mixture of MTBE and heptane.

In certain embodiments, the reductive amination is performed in a solvent selected from a lower carbinol, 2,2,2-trifluoroethanol, dichloromethane, tetrahydrofuran, and acetonitrile.

In certain embodiments, the reductive amination is performed in a solvent comprising a lower carbinol.

In certain embodiments the lower carbinol is methanol.

In certain embodiments the lower carbinol is part of a co-solvent mixture.

In certain embodiments the co-solvent mixture comprises methanol and tetrahydrofuran. In some embodiments, the co-solvent mixture consists of a 2:1 (v:v) mixture of methanol and tetrahydrofuran.

In certain embodiments NaBH$_4$ is added to a mixture of the compound of formula XIV and the compound of formula II in a mixture of methanol and tetrahydrofuran which has been cooled to −5±5° C.

In certain embodiments NaBH$_4$ is added to a mixture of the compound of formula XIV and the compound of formula II in a mixture of methanol and tetrahydrofuran which has been cooled to −10±5° C.

In some embodiments, at most 1.1 equivalents of the compound of formula II, relative to the compound of formula XIV, is used.

In some embodiments, at most 1.0 equivalents of the compound of formula II, relative to the compound of formula XIV, is used.

In certain embodiments the NaBH$_4$ is added in portions while maintaining the reaction mixture temperature at less than 22° C.

In certain embodiments the NaBH$_4$ is added in at least 5 portions spaced at least 15 minutes apart.

In certain embodiments the reaction mixture is stirred at 20±5° C. following completion of the addition of NaBH$_4$ in portions.

In certain embodiments the reaction mixture is stirred at 20±5° C. for at least 1 hour.

In certain embodiments the reaction mixture is stirred at 20±5° C. for at least 3 hours.

In certain embodiments the reductive amination further comprises the steps of:
1) stirring the reaction mixture until Compound 7 is present at least 75 area % by HPLC analysis;
2) quenching the reaction mixture by the addition of saturated NH$_4$Cl; and
3) concentrating the resulting mixture.

In certain embodiments, the reductive amination further comprises the steps of:
1) partitioning the product after between an aqueous phase and an IPAc phase;
2) adjusting the pH of the aqueous phase to 9-10 by the addition of NaOH;
3) separating the IPAc phase;
4) extracting the aqueous phase with IPAc; and
5) obtaining Compound 7 from the combined IPAc phases.

In certain embodiments, the acid compound HX is a mineral acid.

In certain embodiments, the acid compound HX is an arenesulfonic acid.

In certain embodiments, the arenesulfonic acid is p-toluenesulfonic acid.

In certain embodiments, the reaction of the compound of Formula XV is performed at 25±5° C.

In certain embodiments 2.5 equivalents of p-toluenesulfonic acid hydrate relative to the compound of Formula XV are added to the solution of the compound of formula XV in THF and IPA.

In certain embodiments the total volume of THF and IPA combined is about 12 volumes.

In certain embodiments the mixture of the compound of formula XV and p-toluenesulfonic acid hydrate in THF and IPA is stirred for at least 15 hours.

In certain embodiments the process for preparing the compound of Formula XVI further comprises the steps of:
a. filtering the reaction mixture; and
b. washing the filter cake with IPA; and
c. drying the filter cake at 35±5° C. under vacuum for at least 15 hours.

In certain embodiments about 4 volumes of IPA are used to wash the filter cake.

In certain embodiments the process for preparing the compound of Formula XVI further comprises recrystallizing the filter cake from methanol.

In certain embodiments between about 10 and about 20 volumes of methanol relative to the filter cake are used for the recrystallization.

In certain embodiments the process for preparing the compound of Formula XVI further comprises the step of recrystallizing the filter cake from a mixture of methanol and ethyl acetate.

In certain embodiments about 5 volumes of methanol and about 5 volumes of ethyl acetate relative to the filter cake are used for the recrystallization.

In certain embodiments the mixture of the filter cake in methanol and acetate is heated to 50±5° C. and stirred for at least 3 hrs.

Certain embodiments further comprise cooling the mixture to 25±5° C. and stirring for at least 3 hrs before filtering.

General Synthetic Methods for Preparing Compounds

The following invention is further illustrated by the following Examples.

In the Examples below and throughout the disclosure, the following abbreviations may be used: MeCN=acetonitrile; DCM=dichloromethane; DMAP=4-dimethylaminopyridine; EDCI=1-Ethyl-3-(3-dimethylaminopropyl)carbodiimide; EtOAc=ethyl acetate; EtOH=ethanol; $H_2O$=water; IPA=isopropanol; IPAc=iso-propyl acetate; MeOH=methanol; MTBE=methyl tert-butyl ether; NMM=N-methylmorpholine=4-methylmorpholine; STAB=sodium triacetoxyborohydride; THF=tetrahydrofuran; $^1$H-NMR=Proton Nuclear magnetic Resonance; HPLC=High Performance Liquid Chromatography; UPLC=Ultra Performance Liquid Chromatography. Other abbreviations may be used and will be familiar in context to those of skill in the art.

Example 1: Preparation of (1R,2S)-2-(4-fluorophenyl)cyclopropan-1-amine (9) as the Free Base

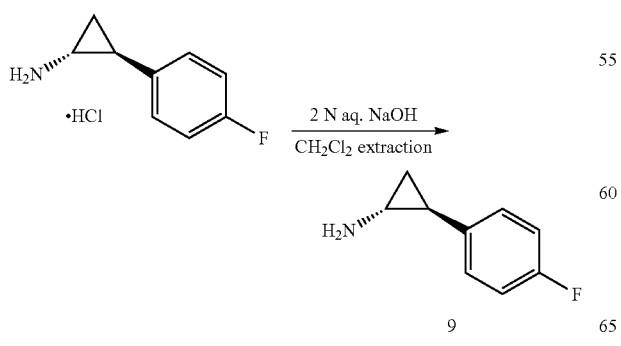

A 12-L, glass round bottom flask was equipped with a $N_2$ bleed. The flask was charged with DCM (2510 mL), (1R,2S)-2-(4-fluorophenyl)cyclopropan-1-amine hydrochloride (505.00 g) and 2 N NaOH solution (NaOH, 224.10 g and purified water, 2810 mL). The contents of the flask were allowed to stir 15 minutes and dissolution was confirmed. The layers were allowed to separate and the aqueous phase was extracted with DCM (1280 mL). The combined organic phase appeared as an opaque liquid, which was transferred to a rotary evaporator bulb and concentrated to a residue at <40° C. under vacuum. The bulb was dried at 25±5° C. under vacuum to afford Compound 9 (413 g, 101%) as an orange oil.

Example 2: Synthesis of N-[(2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (7) and its bis-tosylate Salt (8)

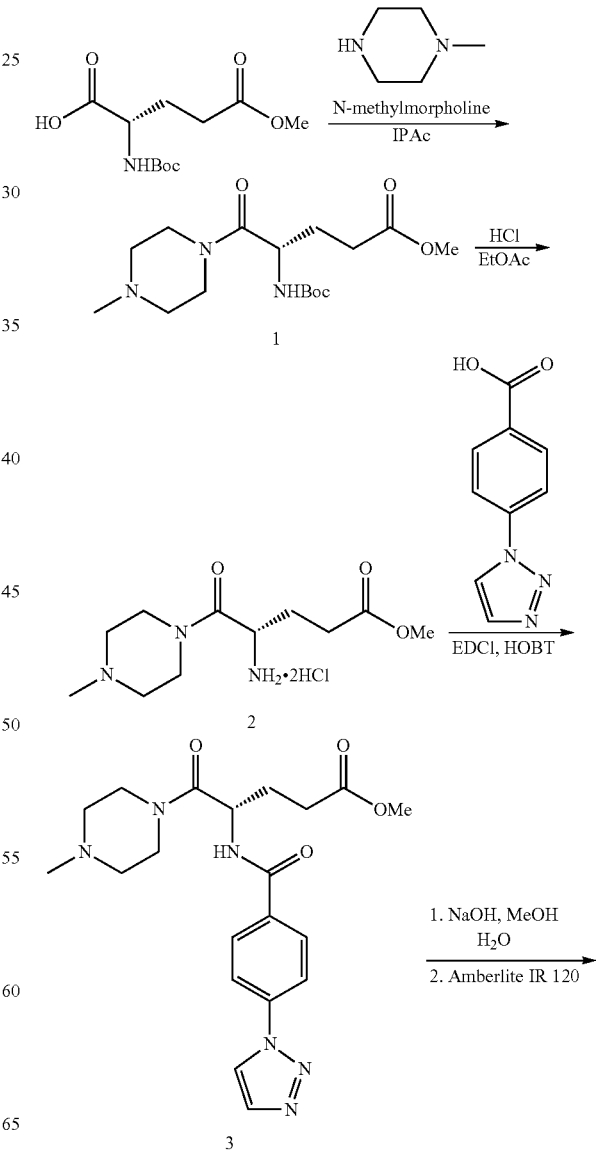

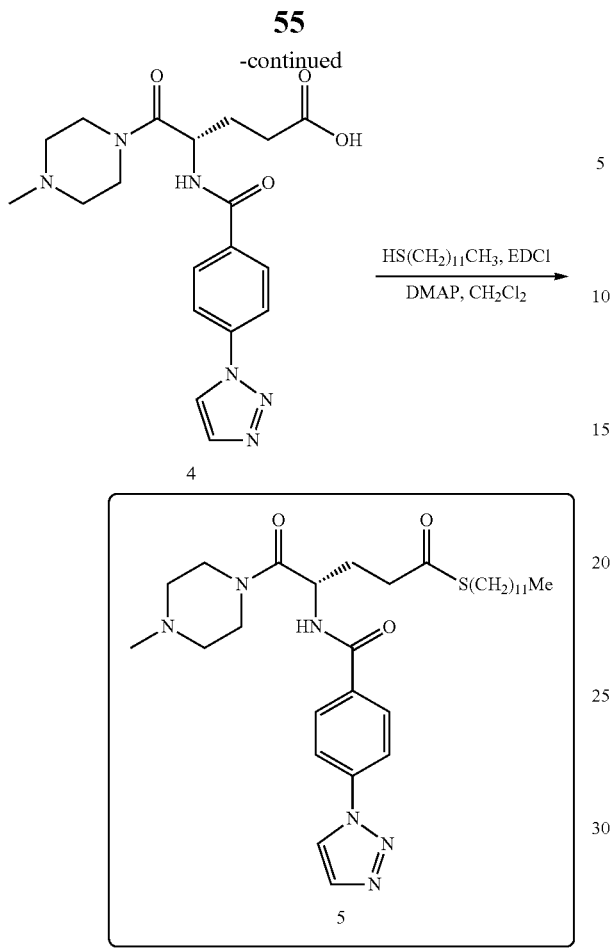

Step 1: Synthesis of methyl (4S)-4-[[(1,1-dimethyl-ethoxy)carbonyl]amino]-5-(4-methylpiperazin-1-yl)-5-oxopentanoate (1)

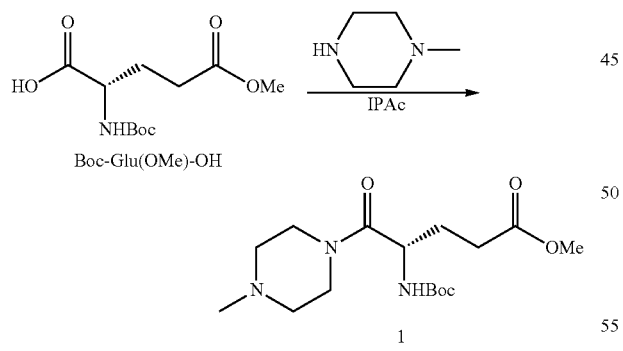

Boc-Glu(OMe)-OH (1900 g) in IPAc (10 volumes) was cooled with stirring, under a $N_2$ atmosphere, to −5-5° C. NMM (801.2 g; 1.1 eq.) and pivaloyl chloride (920.7 g; 1.05 eq.) were added while keeping the temperature at −5-5° C., and the resulting mixture was stirred at this temperature for 2 hrs. 4-Methylpiperazine (1.05 eq.) was added while keeping the temperature between −5-5° C., and the resulting mixture was stirred at −0-5° C. for 1 hr. The reaction was then quenched by the addition of 5% $NaHCO_3$ and the aqueous layer was extracted three times with 2 volumes each time of IPAc. The organic phases were combined, washed with brine, and dried over $Na_2SO_4$. Compound 1 was obtained as a yellow oil, 1.91 kg, 76% yield.

Step 2: Synthesis of methyl (4S)-4-amino-5-(4-methylpiperazin-1-yl)-5-oxopentanoate, HCl Salt (2)

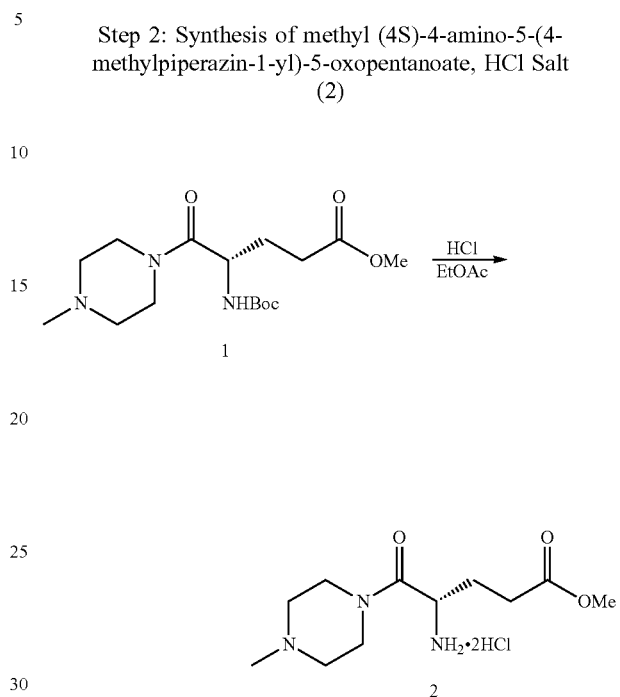

A solution of Compound 1 (1.91 kg) in EtOAc (EtOAc; 5 volumes) was cooled with stirring to 0-5° C. and treated with 1.05 eq. of 1.5M HCl in 20 L of EtOAc while keeping the temperature between 0-5° C. The resulting mixture was stirred at 0-5° C. for 12 hrs, and then HCl gas was passed through the mixture for 3 hrs. The resulting mixture was stirred for an additional 19 hours, then filtered through CELITE®, and the filter cake was washed with EtOAc (2×4 L), and the combined organic phases were concentrated in vacuo at 20-30° C. to afford Compound 2 (1.3 kg; 74% yield) as white solid.

Step 3: Synthesis of methyl (4S)-4-[4-(1H-1,2,3-triazol-1-yl)benzoylamino]-5-(4-methylpiperazin-1-yl)-yl)-5-oxopentanoate (3)

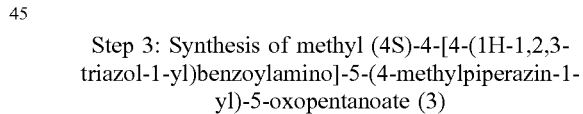

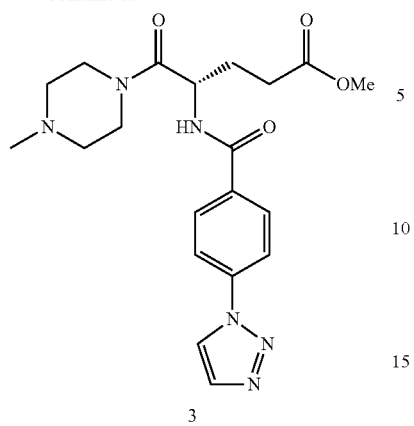

3

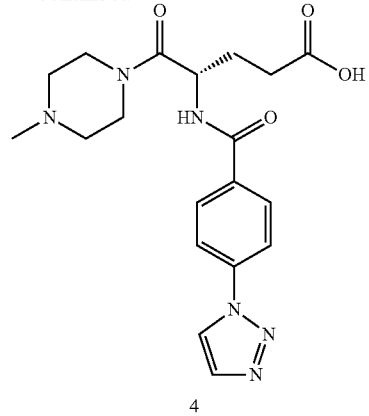

4

4-(1H-1,2,3-Triazol-1-yl)benzoic acid (101, 597.8 g; 1.0 eq.) was dissolved, with stirring and under a N₂ atmosphere, in THF (7.8 L; 13 vol.) and water (1.38 L; 2.3 vol.). NMM (1119.5 g; 3.5 eq.) was added and dissolved with stirring, and the reaction was cooled to below 10° C. Compound 2 (1200 g; 1.2 eq.) was added while keeping the temperature of the reaction mixture at or below 10° C., and the resulting mixture was stirred below 10° C. for 30 minutes. HOBt (470.0 g; 1.1 eq.) and EDCI (666.8 g; 1.1 eq. were added to the reaction mixture while maintaining the temperature below 10° C., and the resulting mixture was stirred at 10-20° C. for 24 hrs. EtOAc (7.8 L; 13 vol.) was then added, followed by 6M NaOH (2.16 L) to adjust the pH to between 9 and 10. Solid NaCl (300 g; 0.5 w/w) was then added to the reaction mixture. The layers were separated, and the aqueous layer was diluted with additional water and extracted with EtOAc (3.6 L, 5×6 vol.). The combined organic phases were washed with brine (3.72 L, 6.2 vol.), dried over Na₂SO₄, and concentrated in vacuo. The residue was washed with MTBE (2×10 vol.) and filtered. The filter cake was dried under vacuum at 35-40° C. to afford 820 g of Compound 3, 67.9% yield.

Step 4: Synthesis of (4S)-4-[4-(1H-1,2,3-triazol-1-yl)benzoylamino]-5-(4-methylpiperazin-1-yl)-5-oxopentanoic Acid (4)

Compound 3 (1214 g; 1.0 eq.) was added to a mixture of MeOH (2.64 L; 2.2 vol.) and THF (2.64 L; 2.2 vol.) under a N₂ atmosphere and with stirring. The resulting suspension was cooled to −10° C., and 3.13 L (1.07 eq.) of a 1M NaOH solution was added while keeping the temperature below 10° C. The resulting mixture was stirred for 6 hrs below 10° C., and then heptane (7.2 L; 6 vol.) was added. The resulting mixture was stirred for at least 30 minutes, and then allowed to settle for at least 30 minutes. The phases were separated and the aqueous phase was transferred to another reaction vessel. AMBERLITE® IR120 (1100 g; 0.95 w/w) beads were added to adjust the pH to 6.3. After stirring the mixture for 30 minutes, the reaction mixture was filtered and the filter cake was washed with THF (2.4 L; 2 vol.). The filtrate was concentrated in vacuo at 35±5° C. to 2-3 vol. The residue was charged with THF (2 L; 1.7 vol.) and concentrated in vacuo at 355° C. This process was repeated an additional 5 times. The crude oil was dissolved in MeOH (2.4 L×2) and then concentrated. The crude material was again dissolved in MeOH (2.4 L) and MTBE (12 L; 10 vol.) at 25±5° C. and stirred overnight. The mixture was then filtered and washed with 2.4 L of MTBE, and the filter cake was dried under vacuum at 45° C. The obtained solid was slurried with DCM (DCM; 3.6 L; 3 vol.) and stirred for 5 hrs at 25±5° C., then filtered and the filter cake washed with MTBE (2.4 L; 2 vol.). The filter cake was dried under vacuum at 35-45° C. to afford 950 g (81%) of Compound 4 as a white solid.

Step 5: Synthesis of dodecyl (4S)-4-[4-(1H-1,2,3-triazol-1-yl)benzoylamino]-5-(4-methyl-piperazin-1-yl)-5-oxopentanethioate (5)

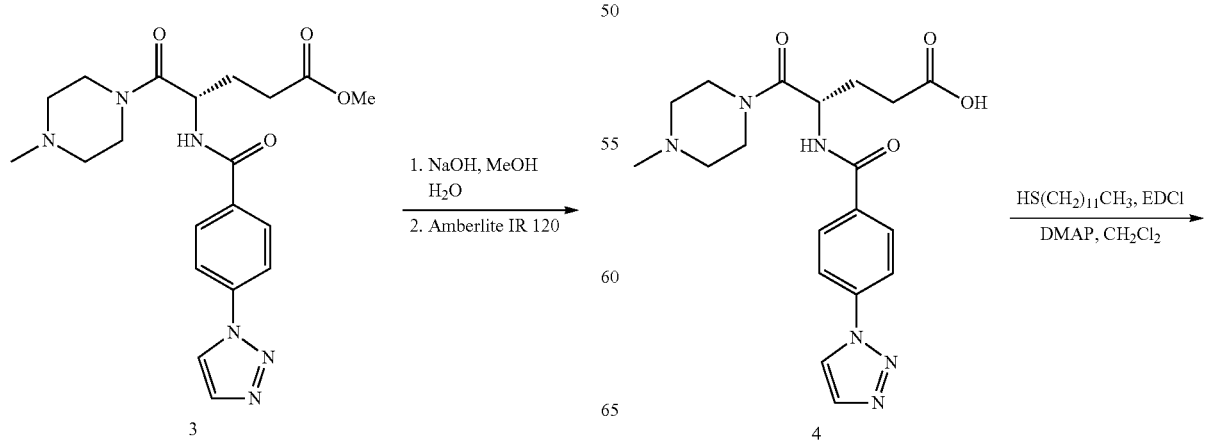

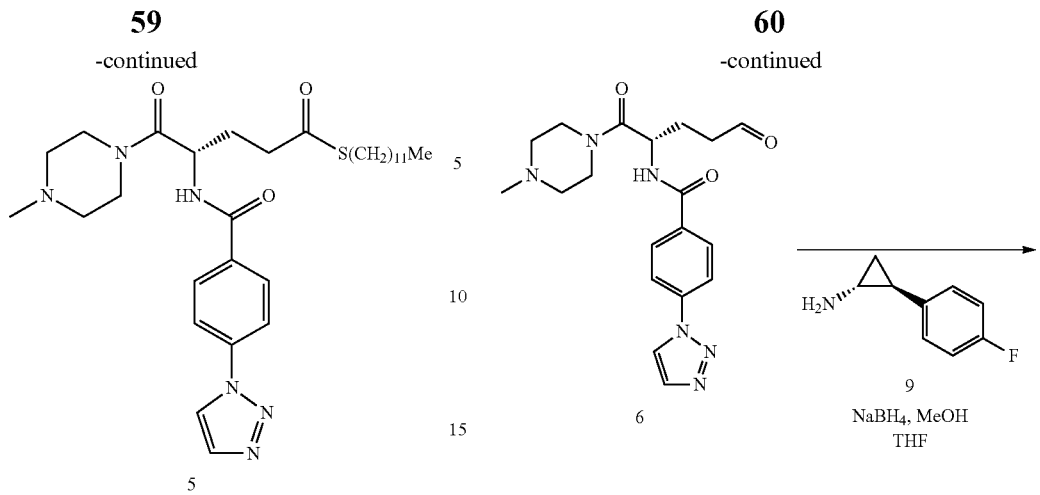

Compound 4 (926 g; 1.0 eq.) was added with stirring and under a $N_2$ atmosphere to 9.3 L (10 vol.) of DCM. The resulting suspension was cooled to 0-5° C. with a water-ice bath and charged with $HS(CH_2)_{11}Me$ (561.66 g, 1.2 eq.) at 0-5° C., followed by DMAP (14.13 g, 0.05 eq.). EDC hydrochloride (531.97 g; 1.2 eq.) was added portionwise while keeping the temperature at 0-5° C. The resulting mixture was stirred at 0-5° C. for 1 hr and at 10-20° C. for 14 hrs. Purified water (1.852 L; 2 vol.) was then added and stirring continued for 1 hr. The layers were separated and the aqueous phase was extracted with DCM (1.85 L×2). The organic layers were combined and washed with brine (2.8 L), dried over $Na_2SO_4$, and then applied to a silica gel chromatography column, using 10×w/w of silica gel. The product was eluted with DCM/MeOH using a gradient elution from 100:0 DCM/MeOH to 20:1, using about 80 volumes total of eluent. The fractions containing pure product were combined and concentrated to afford Compound 5 as a yellow syrup. The crude syrup was dissolved in MTBE (2.8 L; 3 vol.) at 30-40° C., and n-heptane (19.6 L; 21 vol.) was added, and the resulting mixture was cooled to 15-25° C. The mixture was stirred for 16 hrs at this temperature under mechanical agitation, and then filtered, and the filter cake was washed with 2.8 L (3 vol.) of heptane. The cake was dried under vacuum to provide 1164 g (82.5%) of Compound 5 as a white solid.

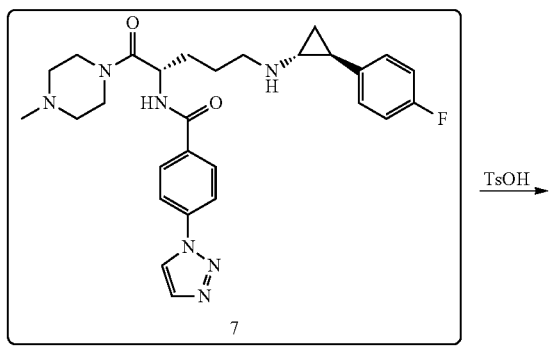

Scheme 2. Synthesis of 7 and 8 from 5.

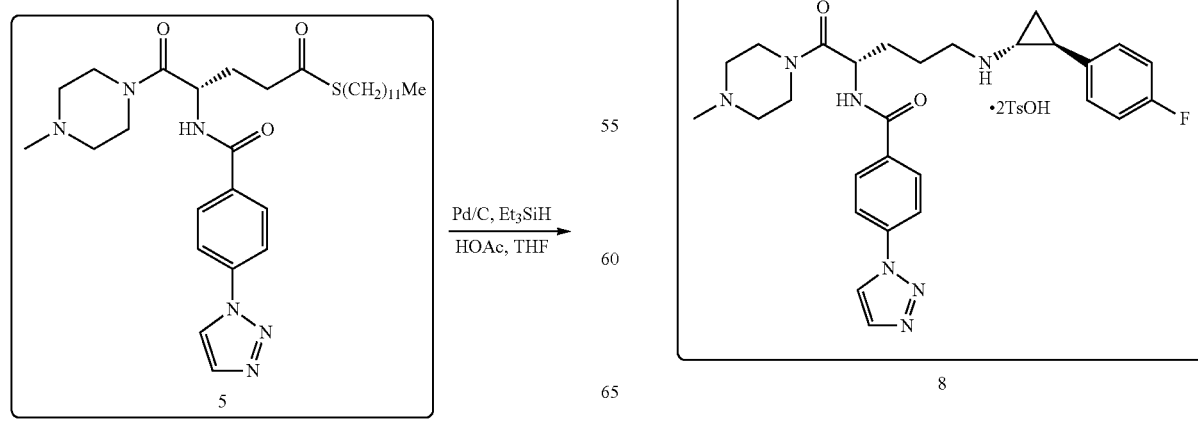

Step 6: Synthesis of (4S)-4-[4-(1H-1,2,3-triazol-1-yl)benzoylamino]-5-(4-methylpiperazin-1-yl)-5-oxopentanal (6)

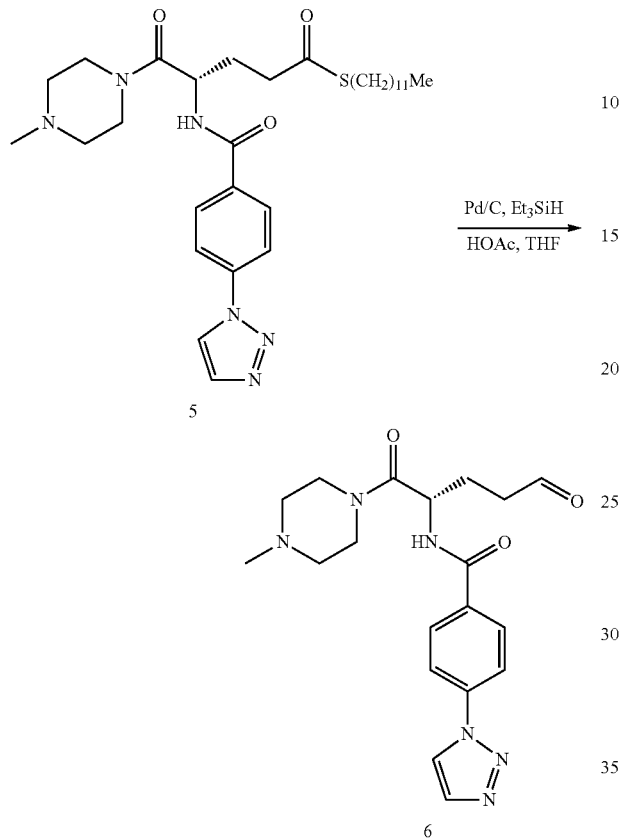

A 50-L, glass, jacketed reactor was equipped with a thermal control unit and a $N_2$ bleed, and charged with THF (9 L) and Compound 5 (900.06 g). The contents were allowed to stir until a solution was observed. Palladium on carbon (50% wet, 140.00 g) was then charged to the reactor and the batch temperature was adjusted to 5±5° C. Glacial acetic acid (140 mL) was added to the batch over 1 minute followed by triethylsilane (1240 mL) over 77 minutes. During the 1 h stir at 5±5° C., an exotherm of 13° C. was observed with a batch temperature increase from 6° C. to 19° C. over approximately 15 minutes. The exotherm subsided and the batch temperature returned to 5±5° C. The batch temperature was then ramped to 20° C. over 86 minutes. The reaction progress was monitored by HPLC (TM.04760) until the area % of Compound 5 was less than 5%.

The reaction was filtered through a CELITE® pad and loose CELITE® (353 g) slurried in DCM (0.5 L) which yielded a filter cake height of ~3 cm. The reactor was washed with DCM (3×2 L) and the washes were used to rinse the filter cake. The filtrate was filtered and concentrated to a residue on a rotary evaporator at <40° C. under vacuum. Total concentration time was 3 h and 48 minutes. n-Heptane (6 L) was charged to the rotovap bulb and the bulb was allowed to rotate without heat or vacuum for 11 h. After this time, the supernatant was decanted. The residue was dissolved in EtOAc (1800 mL) then n-heptane (6 L) was added. The resulting suspension was rotated for 3 h then the supernatant was decanted. The residue was dissolved in THF (6 L) at <30° C. over 32 minutes. The resulting solution was concentrated to 4 volumes (3650 mL) at <40° C. over 20 minutes. After this time, the batch was sampled for quantitative HPLC analysis (TM.04761) to give a concentration of 154.95 mg/mL of Compound 6 and the batch was stored at 2 to 8° C. for use in Step 7.

Step 7: Synthesis of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (7)

A 50-L reactor was charged with a solution of Compound 6 as a solution in THF (3.650 L) using THF (2 L) as a rinse. A solution of Compound 9 (288 g) in MeOH (3 L) was added to the reactor using MeOH (5 L) as a rinse and the batch was stirred for 2 h. After this time, the batch temperature was cooled to −5±5° C. $NaBH_4$ (56.00 g) was added in 10 portions spaced at least 15 minutes apart while maintaining the batch temperature <22° C. After the addition was complete, the batch temperature was adjusted to 20±5° C. and the resulting solution was allowed to stir 18 h. The batch was sampled for UPLC analysis (TM.04762) to give 83.8% Compound 7. The reaction was cooled to 10±5° C. and quenched with solution of $NH_4Cl$ (421.01 g) in purified water (890 mL) at <25° C. The batch was filtered and concentrated at <40° C. to 7 volumes. Total concentration time was 2 h and 7 minutes. The concentrated solution was diluted with IPAc (11 L) then treated with 2N NaOH solution (NaOH, 136.30 g and purified water, 1700 mL) at <25° C. The layers were allowed to separate and the aqueous phase was extracted with IPAc (2 L). The combined organic layers were washed with purified water (1 L) then filtered and the reactor was rinsed with IPAc (2×2 L). The filtrate was concentrated to 2 volumes over 2 h and 30 minutes then solvent swapped with IPA (2×3 L). IPA (2×2 L) was used to transfer the batch to the reactor. THF (4 L) was charged to the reactor and the batch was sampled for UPLC analysis (TM.04762) to give a concentration of 59.18 mg/mL Compound 7 and 13.12% Compound 9. The jacket temperature was adjusted to 5±5° C. and the batch was held for Step 8.

Step 8: Synthesis of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl) benzamide, bis-tosylate Salt (8)

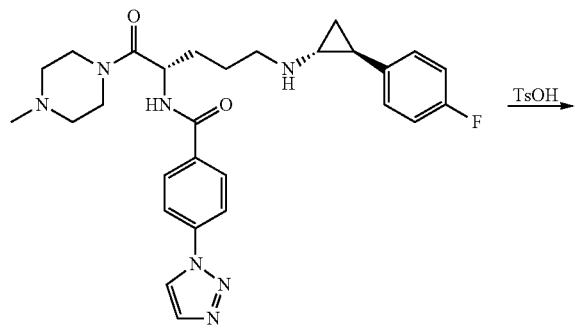

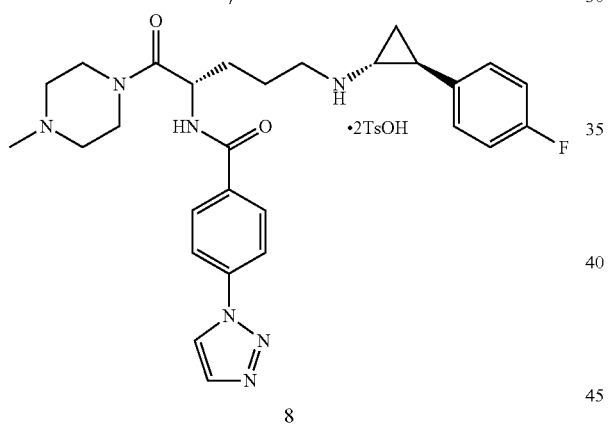

The batch temperature of the batch from Step 7 was adjusted to 20±5° C. and QUADRAPURE® AK resin (843.79 g) was charged to the batch solution. The contents of the reactor were allowed to stir 17 h before sampling for UPLC analysis (TM.04762) to give 3.27% Compound 9 (specification: Compound 9 ≤2 wt % with respect to Compound 7). The batch was allowed to stir a further 24 h before sampling a second time for UPLC analysis (TM.04762) to give 0.91% Compound 9. The resin was filtered off and rinsed with pre-filtered IPA (3 L). The reactor was cleaned to ensure no solids remained and rinsed with pre-filtered THF (10 L). The batch solution was returned to the reactor via an in-line filter and the line was rinsed with pre-filtered THF (1070 mL). The temperature was adjusted to 25±5° C. before charging the pre-filtered TsOH.H$_2$O solution (TsOH.H$_2$O, 488.51 g and THF, 710 mL). The line was rinsed with pre-filtered THF (530 mL) and the batch was stirred for 25 h and 21 minutes. The batch was then filtered and rinsed with pre-filtered IPA (2×1060 mL). The filter cake was conditioned under N$_2$ for 42 h. After this time, the filter cake was sampled for UPLC analysis (TM.04762, TM.04780).

The filter cake was transferred into two drying trays and dried at 35±5° C. under vacuum for approximately 255 h to reach constant weight. The batch was dried a further 72.5 h and then subjected to MeOH recrystallization. The 50-L reactor was rinsed with pre-filtered MeOH (7 L) then the reactor was charged with the batch (770 g) and pre-filtered MeOH (12 L). The batch temperature was set to 65° C. and reflux was reached at 64° C. Solids were still observed after the batch was stirred 30 minutes at reflux. Additional pre-filtered MeOH (1540 mL) was added to achieve dissolution. The batch temperature was then cooled to 20±5° C. over 2 h and 8 minutes and the contents were allowed to stir 17.5 h. After this time, the batch was filtered and the filter cake was washed twice with pre-filtered MeOH (1060 mL and 1070 mL). The filter cake was dried at 35±5° C. under vacuum for approximately 25.5 h to reach constant weight. There was obtained 578 g (43% yield) of Compound 8 as a white solid.

HPLC Methods
Test Methods TM.04760, TM.04761 and TM.04780
Instrument Conditions:
Column: XBridge C18, 3.5 μm, 4.6×150 mm
Mobile Phase A: 0.1% v/v ammonium hydroxide in water
Mobile Phase B: 100% Acetonitrile
Column Temperature: 30° C.
Sample Temperature: Ambient
Flow Rate: 1.0 mL/min
Injection Volume: 5 μL
Needle Wash/Diluent 50/50 Acetonitrile/water
Detection: UV@260 nm
Total run time: 25 min
Gradient: See table 1

TABLE 1

| Time (minutes) | % A | % B |
|---|---|---|
| 0.0 | 95 | 5 |
| 10 | 65 | 35 |
| 15 | 5 | 95 |
| 20 | 5 | 95 |
| 20.1 | 95 | 5 |
| 25 | 95 | 5 |

Test Method TM.04762
Instrument Conditions:
Column: Acquity UPLC BEH C18, 1.7 μm, 2.1×150 mm
Mobile Phase A: 0.2% v/v TFA in water
Mobile Phase B: 0.185% v/v TFA in Acetonitrile
Column Temperature: Ambient
Sample Temperature: 10° C.
Flow Rate: 0.4 mL/min
Injection Volume: 1.5 μL
Sample Concentration 2 mg/mL
Needle Wash/Diluent 50/50 Acetonitrile/water
Detection: 260 nm or 220 nm for IPC ratio of CPD. 9 to IMG-241
Data Collection Time 30 min
Post Run Equilibration Time 5 min
Total run time: 35 min
Gradient: See table 2

TABLE 2

| Time (minutes) | % A | % B |
| --- | --- | --- |
| 0.0 | 95 | 5 |
| 3 | 95 | 5 |
| 13 | 80 | 20 |
| 21 | 80 | 20 |
| 25 | 20 | 80 |
| 30 | 20 | 80 |
| 30.1 | 95 | 5 |
| 35 | 95 | 5 |

Example 3: Alternate Synthesis of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (7) and its bis-tosylate Salt (8)

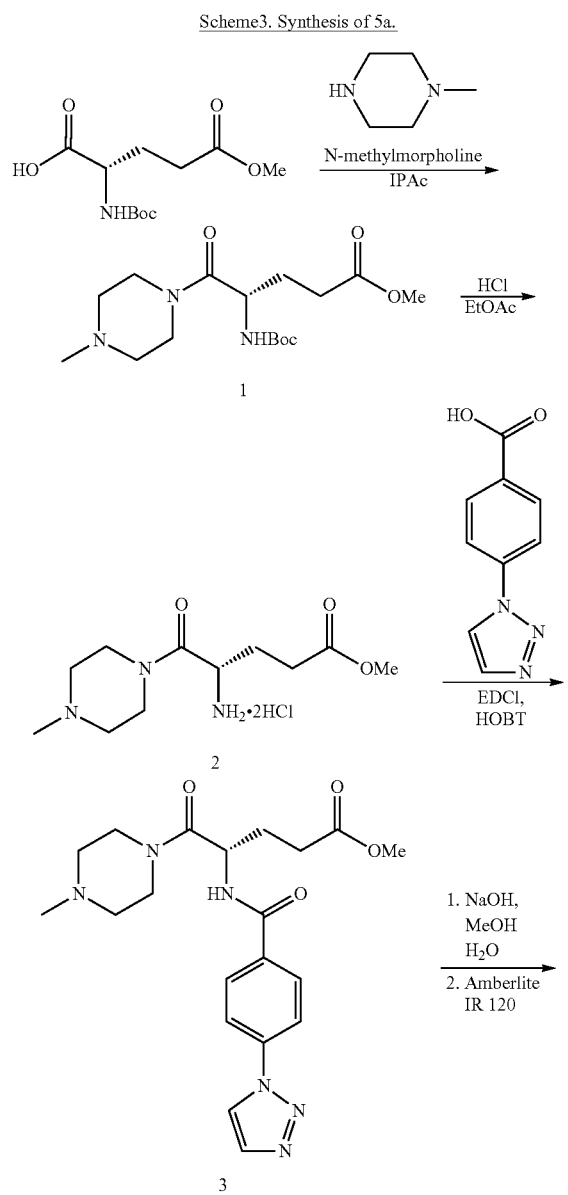

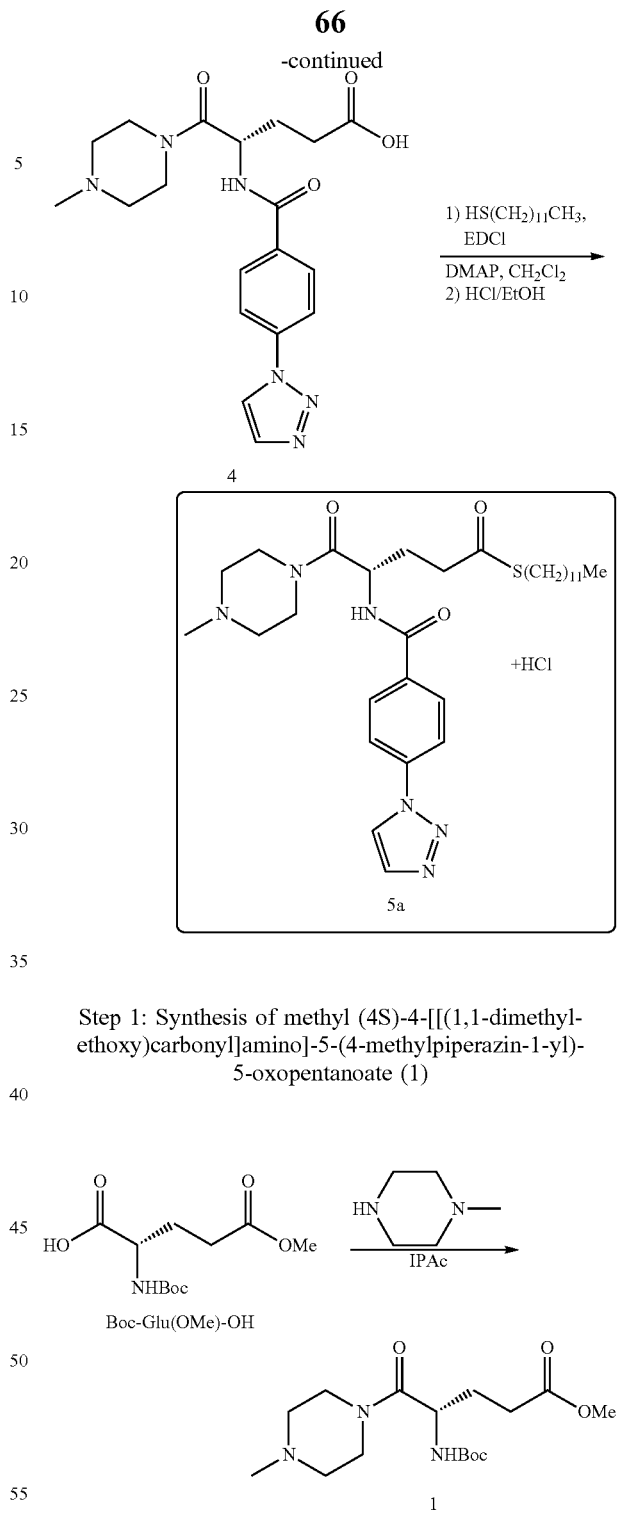

Step 1: Synthesis of methyl (4S)-4-[[(1,1-dimethylethoxy)carbonyl]amino]-5-(4-methylpiperazin-1-yl)-5-oxopentanoate (1)

Boc-Glu(OMe)-OH (35 kg) in IPAc (311.5 kg 10 V) was cooled with stirring, under a $N_2$ atmosphere, to 0-10° C. NMM (15.05 kg; 1.1 eq.) and pivaloyl chloride (16.8 kg; 1.05 eq.) were added while keeping the temperature at 0-10° C., and the resulting mixture was stirred at this temperature for 1 hr, after which time the mixture was allowed to warm to 15-25° C. The mixture was stirred at this temperature for 3 hrs. A sample drawn for analysis showed that starting material had been consumed by this time. The reaction was then quenched by the addition of 5% $NaHCO_3$ (175 L, 5 V)

and the aqueous layer was extracted with IPAc (155.75 kg, 5V×2). The organic phases were combined, washed with 25 wt % aq NaCl (175 L, 5 V), and concentrated under vacuum to ~5 V. IPAc (311.5 kg, 10 V) was added, and the mixture was concentrated under vacuum to ~5 V. A sample drawn for KF analysis showed <0.1% H₂O. The residue was then diluted with dioxane (360.5 kg, 10 V) and concentrated under vacuum to 5 V, affording 42.55 kg of Compound 1 as a crude solution in 173.0 L dioxane.

Step 2: Synthesis of methyl (4S)-4-amino-5-(4-methylpiperazin-1-yl)-5-oxopentanoate, HCl Salt (2)

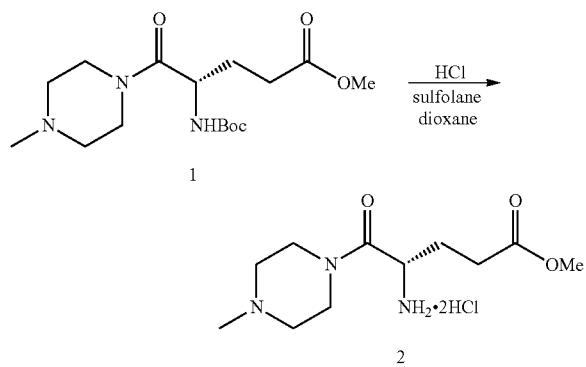

The solution of Compound 1 (42.55 kg) in dioxane from the previous step was combined with sulfolane (375.3 kg, 7 V) and 4 M HCl in dioxane (161.7 kg, 5.0 equiv) at 20-30° C. The mixture was stirred at 25-30° C. for 5 hrs. A sample drawn for analysis showed 2% of Compound 1 remaining at this point. MTBE (377.8 kg, 12.0 V) was then added at 25±5° C., and the mixture was stirred for 1 hr, then centrifuged. The filter cake was washed with MTBE (62.98 kg, 2.0 V) under N₂, affording three batches of Compound 2 (combined total weight: 178.35 kg, corrected mass of product: 31.3 kg).

Step 3: Synthesis of methyl (4S)-4-[4-(1H-1,2,3-triazol-1-yl)benzoylamino]-5-(4-methylpiperazin-1-yl)-5-oxopentanoate (3)

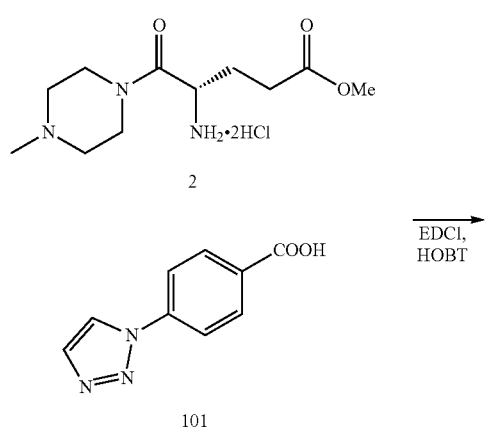

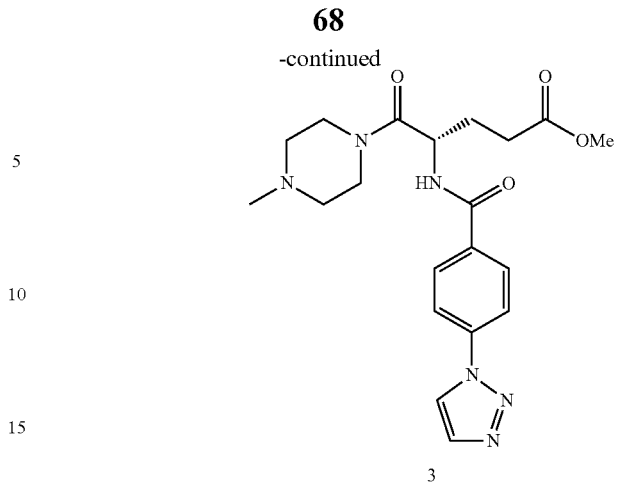

The solution from the previous step (178.25 kg; corrected mass of product 31.3 kg) and THF (171.81 kg, 13 V) was combined with NMM (27.77 kg, 3.5 equiv), then H₂O (34.16 kg, 2.3 V) at 0-10° C. The mixture was stirred at this temperature for 3 hrs, then 4-(1H-1,2,3-triazol-1-yl)benzoic acid (101, 14.85 kg, 1.0 equiv), HOBt (11.73 kg, 1.1 equiv), and EDCI (18.12 kg, 1.2 equiv) were added. The mixture was stirred at ambient temperature (20-30° C.) for 4 hrs. A sample drawn for analysis showed 1.6% of 101 remaining at this point. The mixture was then diluted with 148.5 kg (10 V) H₂O, and the pH was adjusted to 10-11 by the addition of NaOH (6 M, 59.4 L, 4.0 V). IPAc (132.17 kg, 10 V) and NaCl (58.4 kg, 4.0 w/w) were then added, and the mixture was stirred for 3 hrs. The layers were separated, the aqueous layer was extracted with IPAc (10 V×4), and the combined organic layers were washed with brine (74.25 L, 5.0 V) and concentrated under vacuum to 10 V. To the residue was added n-heptane (50.49 kg, 5 V) at 40-50° C., and the mixture was stirred 2 hrs at this temperature, then cooled to 5-15° C. and stirred for an additional 2 hrs. The solid that formed was removed by filtration and dried under vacuum at 35-45° C., affording Compound 3 (25.33 kg; P: 97.4%, 55.4%) as a light yellow solid.

Step 4: Synthesis of (4S)-4-[4-(1H-1,2,3-triazol-1-yl)benzoylamino]-5-(4-methylpiperazin-1-yl)-5-oxopentanoic Acid (4)

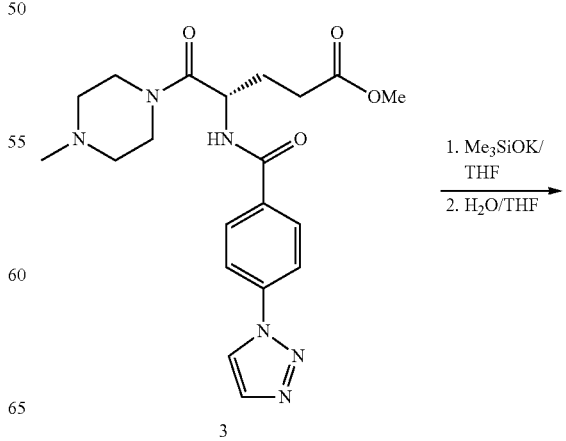

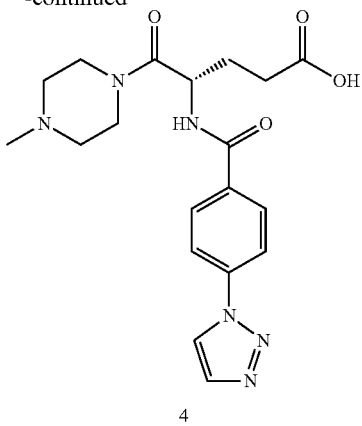

In a reactor were combined Compound 3 (21.0 kg, 1.0 equiv), THF (186.9 kg, 10 V), and Me₃SiOK (7.77 kg, 1.2 equiv) at 20-30° C. The mixture was stirred for 8.0 hrs at 20-30° C. A sample drawn for analysis at this point showed that Compound 3 had been consumed. Heptane (142.8 kg, 10 V) was charged to the reaction vessel, and the mixture was stirred 12 hrs. The supernatant was decanted, leaving a yellow oil. H₂O (21.0 kg, 1 V) and THF (161.5 kg, 10 V) were then added, the mixture was stirred at 20-25° C. for 30 min, then AMBERLITE® IR120 was added to adjust the pH to 6.4. The mixture was stirred for 30 min, and the solid that had formed was removed by filtration and rinsed with MeOH (82.95 kg, 5 V). The combined filtrate was concentrated to 4-5 V. MeOH (82.95 kg, 5 V) and CH₃CN (163.8 kg, 10 V) were added, affording a yellow solution. The solution was concentrated to 4-5 V. The process of addition of MeOH (82.95 kg, 5 V) and CH₃CN (163.8 kg, 10 V), followed by concentration to 4-5 V, was repeated until KF analysis on a sample showed <1.0% of H₂O remaining. GC analysis was then performed to find the MeOH/CH₃CN ratio in the solution. The amount of MeOH was adjusted by addition or evaporation until the total volume of MeOH was 2.0 V. The temperature was adjusted to 30±5° C., and the solution was stirred for at least 0.5 hr at this temperature. CH₃CN (245.7 kg, 15 V) was added slowly to the solution at this temperature, and the mixture was stirred for at least 2 hrs. The mixture was then cooled to 15±5° C. The solid that had formed was collected by filtration, washed with CH₃CN (40.95 kg, 2.5 V), and dried at 45° C. under vacuum for 60 hrs to afford Compound 4 (5.63 kg, P: 96.1%, KF: 1.5%, Chiral HPLC purity: 99.4%) as a white solid.

The filtrate from the preceding step was concentrated to 1-2 V under vacuum at 40±5° C. MeOH (20 L, 4.0 V) was added, and the mixture was stirred for at least 0.5 hr at 15±° C. The pH was adjusted to 6.0-6.4 with the addition of an ethanolic solution of HCl (33 wt %). The mixture was stirred for at least 0.5 hr at 15±° C. The mixture was evaporated to 1-2 V under vacuum at 40±5° C. CH₃CN (16 L, 4.0 V) was added, and the mixture was stirred for at least 0.5 hr at 15±° C. Additional CH₃CN (24 L, 6.0 V) is added, and the mixture was stirred at least 8 hrs at 15±5° C. The solid that formed was removed by filtration on a Büchner funnel, washed with CH₃CN (8 L, 2.0 V), and dried under vacuum for at least 15 hrs at 40±5° C. to afford Compound 4 (5.9 kg, P: 97.4%).

Step 5(a): Synthesis of dodecyl (4S)-4-[4-(1H-1,2,3-triazol-1-yl)benzoylamino]-5-(4-methyl-piperazin-1-yl)-5-oxopentanethioate Hydrochloride Salt (5a)

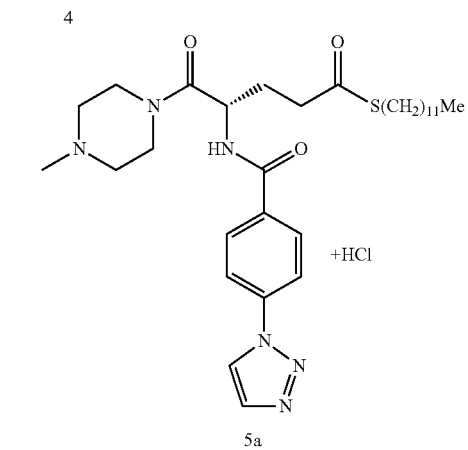

Compound 4 (3.00 kg; 1.0 eq.) was added with stirring and under an N₂ atmosphere to 45 L (15 V) of DCM. The resulting suspension was cooled to 0-5° C. and charged with HS(CH₂)₁₁Me (1.82 kg, 1.2 eq.) at 0-5° C., followed by DMAP (46 g, 0.05 eq.). EDC hydrochloride (1.73 kg; 1.2 eq.) was added portionwise while keeping the temperature at 0-5° C. The resulting mixture was stirred at 0-5° C. for 1 hr, then warmed to 10-20° C. The mixture was stirred at this temperature for at least 4 hrs. Samples were drawn every 3.0±0.2 hrs for HPLC analysis, until the area under the curve for Compound 4 was less than 3.0% of the total area. At this point, purified water (15 L; 5.0 V) was then added with stirring while maintaining a temperature of 15±5° C. Stirring was continued for at least 1 hr at this temperature. The layers were separated, and the aqueous phase was extracted with DCM (15 L, 5.0 V). The combined organic layers were washed with brine (5.0 kg in 15 L purified water, 5.0 V) and evaporated to 1-2 V under vacuum at 40±5° C. EtOH (24 L, 8.0 V) was added, and the mixture was evaporated to 1-2 V under vacuum at 40±5° C. EtOH (15 L, 5.0 V) and the reaction vessel was rotated for at least 0.5 hr at 40±5° C. EtOH (30 L, 10.0 V) was added with stirring. An ethanolic solution of HCl (33 wt %, 994 g, 1.2 equiv) was added dropwise at 25±5° C. The mixture was stirred at least 3 hrs at 25±5° C. The solid that formed was collected by filtration on a Büchner funnel, washed with EtOH (6 L, 2.0 V), and dried under vacuum for at least 15 hrs at 40±5° C., to afford Compound 5a (4.20 kg, purity: 93.4%, LOD: 2.54%).

Scheme 4. Synthesis of 7 and 8 from 5a.

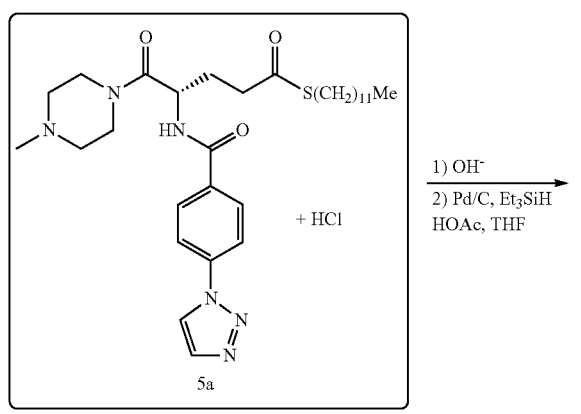

5a

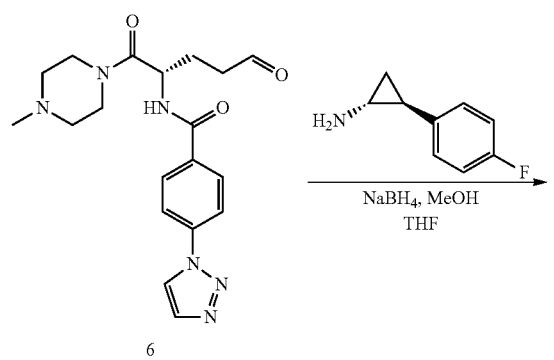

6

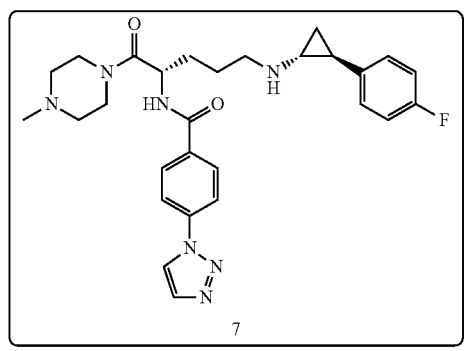

7

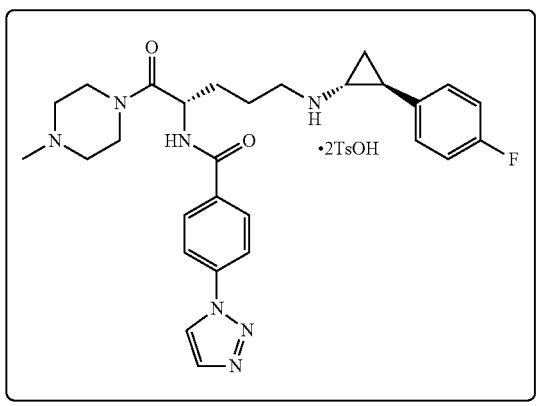

8

Step 5(b): Synthesis of dodecyl (4S)-4-[4-(1H-1,2,3-triazol-1-yl)benzoylamino]-5-(4-methyl-piperazin-1-yl)-5-oxopentanethioate (5)

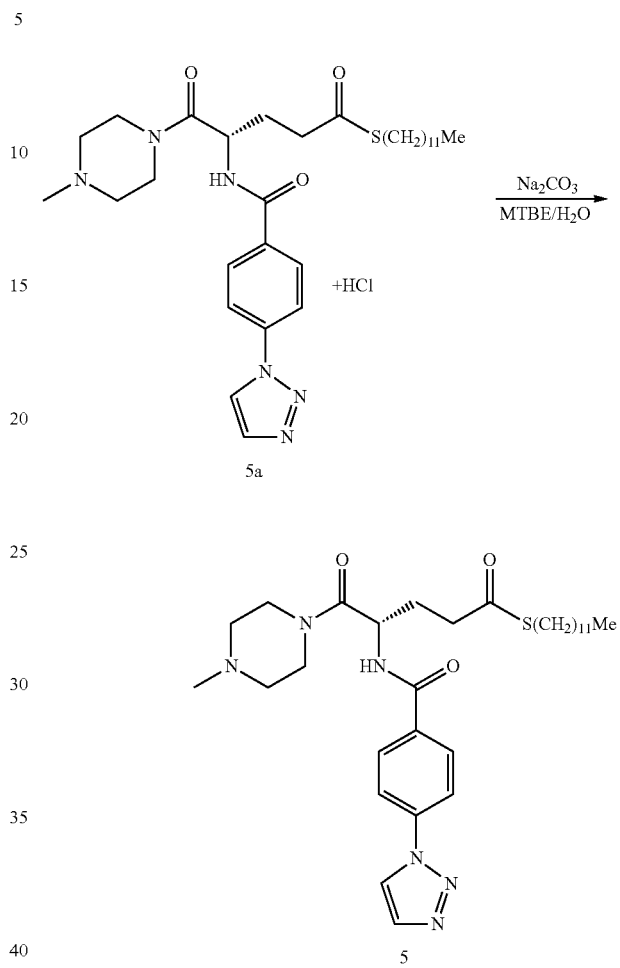

Compound 5a (4.10 kg, calculated as 4.0 kg) was added with stirring to MTBE (40 L, 10.0 V). Na$_2$CO$_3$ (2.05 kg in 20 L purified H$_2$O) was added at 20±5° C., and the mixture was stirred at least 4 hrs at 20±5° C. The layers were separated, and the organic phase was washed 2× with NaCl (6.67 kg in 20 L purified water, 5.0 V, for each wash), then concentrated under vacuum to 1-2 V at 35±5° C. MTBE (4 L, 1.0 V) was added, and the reaction vessel was rotated for at least 0.5 hr at 35±5° C. n-Heptane (8 L, 4.0 V) was added with stirring, the mixture was warmed to 40±5° C. Additional n-heptane (60 L, 15.0 V) was added at this temperature, and the mixture was stirred 1.0 hr at this temperature. The mixture was then cooled to 0±5° C., and stirred at least 3 hrs at this temperature. The mixture was then warmed to 15±5° C., and stirred for at least 2 hrs at this temperature. The resulting solid was removed by filtration on a Büchner funnel, washed with n-heptane (8 L, 2.0 V), and dried under vacuum for at least 15 hrs at 40±5° C. Samples were withdrawn for KF analysis and drying was continued until KF≤5%.

Step 6: Synthesis of (4S)-4-[4-(1H-1,2,3-triazol-1-yl)benzoylamino]-5-(4-methylpiperazin-1-yl)-5-oxopentanal (6)

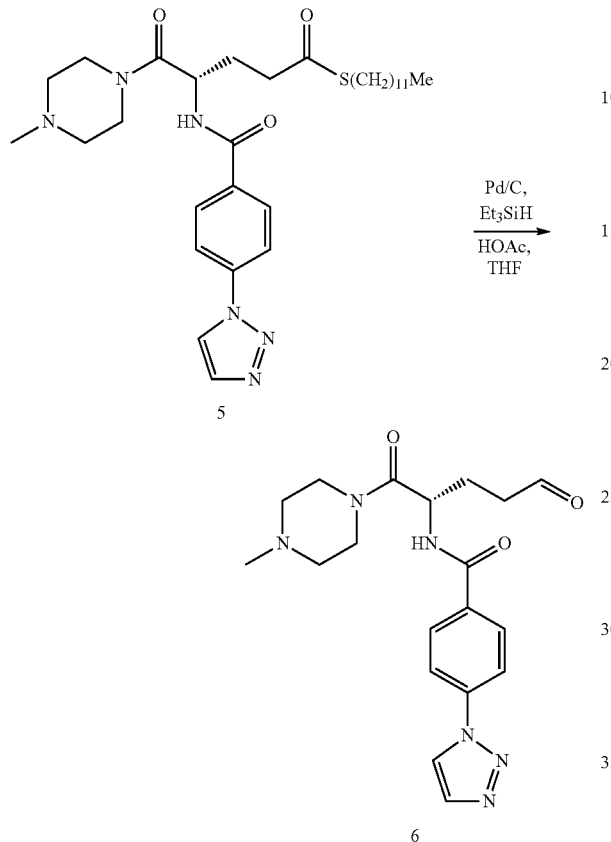

A reaction vessel was purged by evacuating to P≤0.08 MPa, followed by addition of N₂ to atmospheric pressure. The cycle was repeated for a total of 3 times. THF (60.08 kg, 9.0 V) was added, followed by Compound 5 (7.50 kg, 1.0 equiv). A solution of anhydrous Pd/C (188 g, 2.5 wt. %) in THF (6.68 kg, 1.0 V) was then added. The reaction vessel was cooled to 5±5° C. Glacial AcOH (1.13 kg, 1.5 equiv), followed by Et₃SiH (6.00 kg, 4.0 equiv) were then added at this temperature. The mixture was stirred for at least 1 hr at 5-20° C., then stirred for 3±0.2 hrs at 15±5° C. A sample was drawn for HPLC analysis every 3±0.2 hrs, and the reaction was continued until the area under the curve for Compound 5 ≤5.0% of the total area. The reaction mixture was then filtered through a pad of CELITE® (6.00 kg) which had been rinsed with THF (20.03 kg, 3.0 V). After filtration, the pad was rinsed with THF (33.38 kg, 5.0 V). The combined filtrates were passed through a microporous filter, then concentrated under vacuum to 2-3 V at 25±5° C. EtOAc (67.50 kg, 10.0 V) was added, and the mixture was concentrated under vacuum to 2-3 V at 25–5° C. Additional EtOAc (67.50 kg, 10.0 V) was added, and the mixture was again concentrated under vacuum to 2-3 V at 25±5° C. The reaction vessel was rinsed with EtOAc (3.38 kg, 0.5 V), and the EtOAc layers were combined, then added dropwise to a mixture of MTBE (55.50 kg, 10.0 V) and n-heptane (51.00 kg, 10.0 V). The mixture was stirred at least 2 hrs at 15±5° C., then cooled to 0±5° C., then stirred for at least 2 hrs. The solid that formed was collected by centrifugation, washed with n-heptane (10.20 kg, 2.0 V), then dried under vacuum at 20±5° C. for at least 6 hrs, affording Compound 6 (88.3% pure, assay: 84.6%, mass: 4.76 kg, mass corrected by assay: 4.03 kg, yield: 81.7%).

Step 7: Synthesis of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (7)

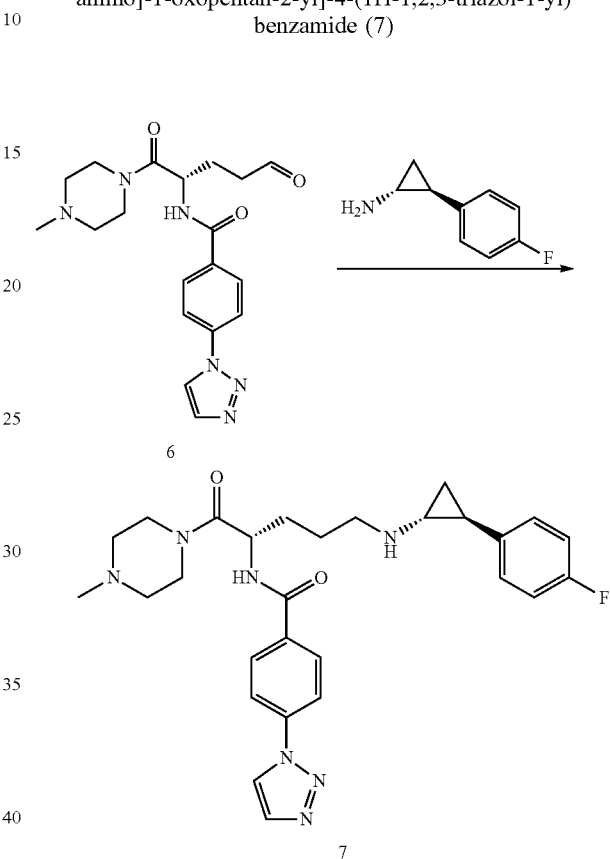

A reaction vessel was purged by evacuating to P≤0.08 MPa, followed by addition of N₂ to atmospheric pressure. The cycle was repeated for a total of 3 times. MeOH (43.13 kg, 14.0 V) and Compound 9 (1.52 kg, 1.0 equiv) was added at 20±5° C. A solution of Compound 6 (4.61 kg, assay: 84.6%, 1.0 equiv) in THF (24.30 kg, 7.0 V) was added through a microporous filter at this temperature, and the mixture was stirred 2±0.2 hrs. The reaction mixture was then cooled to −10±0.5° C. NaBH₄ (390 g, 1.0 equiv) was added in at least 5 batches, spaced at least 15 min apart, while maintaining this temperature. The mixture was stirred an additional 2.0±0.2 hrs at this temperature, then was warmed to 20±5° C. over the course of an hour, and stirred 1.0±0.2 hrs at this temperature. A sample was drawn for HPLC analysis, and if the area under the curve of the product is <75% of the total area, an additional 39 g of NaBH₄ is added. The mixture was stirred for at least 8 hrs at 20±5° C., then cooled to 0±5° C. A solution of NH₄Cl (2.57 kg) in purified H₂O (7.80 kg, 2.0 V) was added to the reaction mixture while maintaining a temperature below 10° C. The mixture was then stirred for 0.5 hr at 10-25° C., then concentrated under vacuum to 3-4 V at 35±5° C. IPAc (67.86 kg, 20.0 V) was then added, the mixture was then chilled to 10±0.5° C., and 2 N NaOH solution was added at this temperature to adjust the pH to 9-10. The mixture was allowed to warm to 20±5° C., then stirred at this temperature for at least 0.5 hr. The layers were separated, and the aqueous phase was extracted with IPAc (33.93 kg, 10.0 V). The organic layers were combined and washed with NaCl solution (7.02 kg in 19.50 kg purified water, 5.0 V, repeated for a total of 2 washes). The organic phase was concentrated to 3-4 V under vacuum at 35±5° C. THF (34.71 kg, 10.0 V) was added to the reaction vessel, and the mixture was concentrated to 3-4 V under vacuum at 35±5° C. IPA (30.81 kg, 10.0 V) was added to the reaction vessel, and the mixture was concentrated 3-4 V under vacuum at 35±5° C. IPA (15.41 kg, 5.0 V) was added to the reaction vessel, and the mixture was stirred for at least 0.5 hour at 35±5° C. to afford a solution of Compound 7 (purity: 80.0%, assay: 12.4%, mass: 34.86 kg, mass corrected by assay: 4.32 kg, yield: 82.0%).

Step 8: Synthesis of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide, bis-tosylate Salt (8)

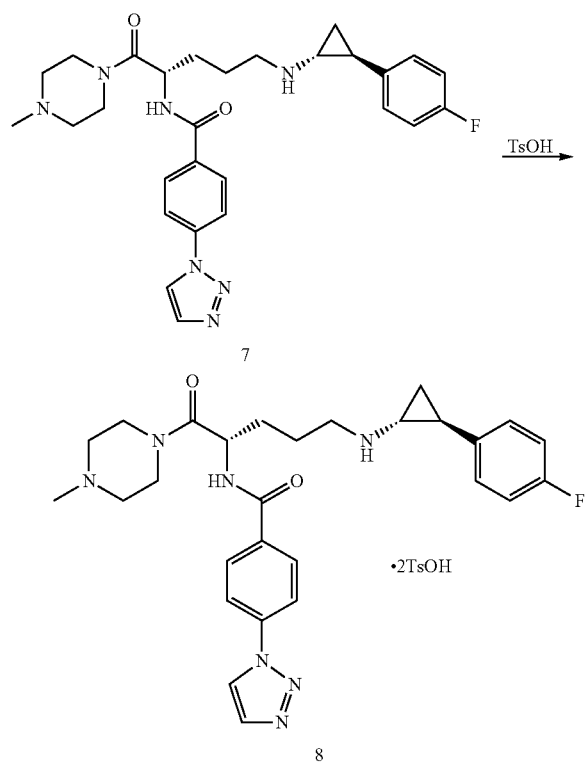

To a mixture of THF (29.19 kg, 8.0 V) and IPA (12.96 kg, 4.0 V) was added a solution of Compound 7 (33.06 kg, assay: 12.4%, 1.0 equiv) in IPA. The mixture was stirred for at least 10 min. A reactor is flushed by first evacuating to P≤0.08 MPa, then introducing N₂ to 1.0 Atm. The flush cycle is repeated for a total of 3 times. The solution of Compound 7 was then added to the reactor through a 0.2 μM microporous filter. A solution of TsOH (3.75 kg, 2.5 equiv) in THF (14.60 kg, 4.0 V) was added with stirring through a 0.2 μM microporous filter at 25±5° C. The mixture was stirred at least 15 hrs at this temperature. The solid that formed was removed by centrifugation, washed with IPA (12.96 kg, 4.0 V), and dried under vacuum for at least 15 hrs at 35±5° C.

A reaction vessel was purged by evacuating to P≤0.08 MPa, followed by addition of N₂ to atmospheric pressure. The cycle was repeated for a total of 3 times. MeOH (24.89 kg, 5.0 V) and EtOAc (28.35 kg, 5.0 V) was introduced to the vessel through the 0.2 μM microporous filter under an N₂ atmosphere. The solid product was then added to the reactor with stirring, and the mixture was warmed to 50±5° C., and stirred for at least 3 hrs at this temperature. The mixture was then cooled to 25±5° C., and stirred for at least 3 hrs at this temperature. The solid was removed via centrifugation, washed with EtOAc (11.34 kg, 2.0 V), and analyzed with HPLC. The EtOAc slurry procedure is repeated if the area % of the product <98.0% or the area % of single impurity >0.5%.

A reaction vessel was purged by evacuating to P≤0.08 MPa, followed by addition of N₂ to atmospheric pressure. The cycle was repeated for a total of 3 times. n-Heptane (42.84 kg, 10.0 V) was introduced to the vessel through the 0.2 μM microporous filter under an N₂ atmosphere. The solid product was then added to the reactor with stirring, and the mixture was stirred for at least 3 hrs at 25±5° C. The solid was removed via centrifugation, washed with n-heptane (12.85 kg, 3.0 V), and dried under vacuum at 35±C for at least 15 hrs to afford the product (5.38 kg, 78.9%).

Example 4: Alternate Synthesis of dodecyl (4S)-4-[4-(1H-1,2,3-triazol-1-yl)benzoylamino]-5-(4-methylpiperazin-1-yl)-5-oxopentanethioate Hydrochloride Salt Step 1: Synthesis of methyl (4S)-4-[[(1,1-dimethylethoxy)carbonyl]amino]-5-(4-methylpiperazin-1-yl)-5-oxopentanoate (1)

A reaction vessel is flushed by evacuation, followed by introduction of N₂. The flush procedure is repeated 3 times. An N₂ atmosphere is maintained throughout the procedure. IPAc (204.85 kg, 10 V, 8.90 w/w) is added, and stirring is begun. A sample drawn for KF analysis reports H₂O=0.04%. Boc-Glu(OMe)-OH (22.98 kg, 1.00 eq.) is charged to the vessel, and the vessel is then chilled to 5±5° C., and the temperature is maintained. N-methylmorpholine (9.88 kg, 1.10 eq.) is then added dropwise, followed by dropwise addition of pivaloyl chloride (11.14 kg, 1.05 eq.). The mixture is stirred ≥1 hr, then N-methylpiperazine (9.20 kg, 1.05 eq.) is added, and the mixture is stirred ≥1 hr. The vessel is then warmed to 20±5° C., and stirring is continued ≥3 hr. Samples are drawn for HPLC analysis (re-sample every 2±0.2 hr), and the reaction is continued until the % area of Boc-Glu(OMe)-OH≤2%.

The reaction is quenched by the addition of aq NaHCO₃ (5 wt. %, 5.0 V). Stirring is continued ≥0.5 hr, then the contents are allowed to stand without stirring ≥0.5 hour. The phases are separated, the aqueous phase is extracted with IPAc (2×102.70 kg, 2×5.0 V, 4.45 w/w), with ≥0.5 hr stirring, followed by ≥0.5 h standing for each extraction. The combined organic layers are washed with aqueous NaCl solution (25 wt. %, 2×5.0 V), concentrated to 4~5 V with temperature held to ≤50° C. IPAc (204.80 kg, 10.0 V, 8.90 w/w) is then added, and the volume is concentrated to 4~5 V at P≤0.08 MPa with temperature held to ≤50° C.

Samples are drawn for KF analysis. The IPAc addition and azeotrope procedure is repeated until KF analysis reports H₂O≤0.1%. Dioxane (236.95 kg, 10 V, 10.30 w/w) is then added, and the volume is concentrated to 4~5 V at P≤0.08 MPa with temperature held to ≤50° C. A sample drawn for HPLC analysis reports purity=95.7%. The solution is stored at 25° C. in the reactor under $N_2$ and is used directly in the next step.

Step 2: Synthesis of methyl (4S)-4-amino-5-(4-methylpiperazin-1-yl)-5-oxopentanoate, HCl Salt A reactor is flushed with $N_2$ by evacuation to ≤0.08 Mpa, followed by introduction of $N_2$. The flush procedure is repeated 3 times. An $N_2$ atmosphere is maintained throughout the procedure. Compound 1 (28.9 kg in dioxane, 1.0 eq.) in dioxane is then added, and the mixture is stirred. Sulfolane (254.9 kg, 7 V, 8.82 w/w) is then added into the reactor. The reactor temperature is adjusted to 25±5° C., and this temperature is maintained throughout the procedure. HCl/dioxane (4 M, 5.0 eq., 109.80 kg) is added, and the mixture is stirred ≥3 hr. Samples are drawn for HPLC analysis every 2±0.2 hrs. Stirring is continued until the area % of Compound 1 ≤2%.

A second reactor is charged with MTBE (385.40 kg, 18 V, 13.32 w/w), and the contents of the first reactor are introduced into the second reactor with stirring at 25±5° C. Stirring is continued ≥1 hr, then the solid that forms is removed by centrifugation and washed with MTBE (162.00 kg, 7.5 V, 5.55 w/w). HPLC analysis of the hygroscopic cake reports purity=95.3%. The filter cake is then added with stirring to MTBE (320.95 kg, 15 V, 11.10 w/w) under N2. The temperature is adjusted to 25±5° C., and the mixture is stirred ≥4 hrs. The cake is then removed by centrifugation and washed with MTBE (80.60 kg, 3.75 V, 2.79 w/w).

HPLC analysis of the filter cake reports purity=95.3%. GC analysis of the filter cake reports MTBE=43.9%, 1,4-dioxane=5.1%, sulfolane=8.2%. The product (crude weight=87.9 kg) is packed in an inner polyethylene (LDPE) bag sealed with cable ties encased within a heat sealed composite LDPE outer bag under $N_2$.

Step 3: Synthesis of methyl (4S)-4-[4-(1H-1,2,3-triazol-1-yl)benzoylamino]-5-(4-methylpiperazin-1-yl)-5-oxopentanoate (3)

A reactor is flushed with $N_2$ by evacuation to ≤0.08 Mpa, followed by introduction of $N_2$. The flush procedure is repeated 3 times. An $N_2$ atmosphere is maintained throughout the procedure. DCM (316.55 kg, 25 V, 33.25 w/w) is charged into the reactor and stirring is begun. Compound 2 (crude weight: 75.03 kg, 1.3 eq.) is then added, and the mixture is cooled to 5±5° C., and this temperature is maintained. N-Methylmorpholine (18.64 kg, 3.50 eq.) is then added, followed by batchwise addition of EDCI (11.60 kg, 1.20 eq.). HOBT (0.68 kg, 0.10 eq.) is then added, followed by Compound 9 (9.60 kg, 1.00 eq.). The mixture is stirred ≥0.5 hr, then the mixture is warmed to 25±5° C., and stirring is continued ≥3 hrs. Samples are drawn for HPLC analysis every 2±0.2 hours, and the reaction is continued until the area % of Compound 9 ≤5%.

The reaction mixture is then cooled to 5±5° C., and $Na_2CO_3$ solution (10 wt. %, 20.0 V) is added dropwise to adjust pH to 9~10. The mixture is then warmed to 25±5° C., and stirring is continued ≥2 hours at 25±5° C. Aqueous NaCl solution (10 wt. %, 10.0 V) is then added into the reactor at 25±5° C., and stirring is continued ≥0.5 hr. The mixture is allowed to stand without stirring ≥0.5 hour.

The organic phase is washed with aq NaCl (15 wt. %, 10.0 V). The mixture is stirred ≥0.5 hr and allowed to stand without stirring ≥0.5 hour, then the layers are separated. The organic layer is concentrated to 9~10 V at ≤40° C. IPAc (126.80 kg, 15.0 V) is then added into the reactor, and the volume is reduced to 9~10 V at ≤45° C. Additional IPAc (126.80 kg, 15.0 V) is then added into the reactor, and the volume is reduced 9~10 V at ≤45° C. GC analysis reports that DCM ≤3.0%.

The mixture is warmed to 45±5° C. n-Heptane (100.35 kg, 15.0 V, 10.20 w/w) is added slowly into the reactor, and the mixture is stirred ≥1 hr, then cooled to 20±5° C. and and stirred ≥2 hrs. The solid that formed is removed by centrifugation and washed with n-heptane (16.45 kg, 2.5 V, 1.70 w/w). HPLC analysis reports purity of compound 3 ≥96.0%. The solid is dried in a vacuum oven ≥12 hrs at 40±5° C. Drying is continued until a sample drawn for LOD analysis reports LOD ≤3%. HPLC analysis of the product reports Compound 3=96.3%, assay: 94.1%, corrected weight: 18.16 kg, yield: 86.4%. The final product is packaged in double LDPE plastic bags sealed with cable ties, and stored in well closed containers at room temperature.

Step 4: Synthesis of (4S)-4-[4-(1H-1,2,3-triazol-1-yl)benzoylamino]-5-(4-methylpiperazin-1-yl)-5-oxopentanoic Acid (4)

A reactor is flushed with $N_2$ by evacuation to ≤0.08 Mpa, followed by introduction of $N_2$. The flush procedure is repeated 3 times. An $N_2$ atmosphere is maintained throughout the procedure. THF (160.75 kg, 10 V, 8.9 w/w) is added, and stirring is begun. Compound 3 (18 kg corrected weight, 1.0 eq.) is then added into the reactor, and the temperature is adjusted to 25±5° C. TMSOK (7.25 kg, 1.3 eq.) is added batchwise, and the mixture is stirred ≥8 hrs. Samples are drawn for HPLC analysis every 20.2 hours, and the reaction is continued until the area % of Compound 3 ≤3%. MeOH (142.10 kg, 10 V, 7.90 w/w) is then added into the reactor at 25±5° C., and the contents are stirred ≥1 hr. The mixture is cooled to 5±5° C. HCl/MeOH is added slowly to adjust pH to 5.4~5.8. The mixture is stirred ≥2 hrs while maintaining pH 5.4~5.8. The solid is removed by centrifugation, and is washed with MeOH (35.30 kg, 5 V, 3.95 w/w). The filtrate is combined with the reaction solution, and concentrated to 4~5 V at ≤40° C. MeOH (141.85 kg, 10 V, 7.90 w/w) is added, and the mixture is concentrated to 4~5 V at ≤40° C. $CH_3CN$ (210.80 kg, 15 V, 11.70 w/w) is added, and the mixture is concentrated to 4~5 V at ≤40° C. Additional $CH_3CN$ (70.95 kg, 5 V, 3.90 w/w) is added into the reactor at 25±5° C. Seed crystals of Compound 4 are introduced into the reactor, and the mixture is stirred ≥0.5 hrs. Additional $CH_3CN$ (210.70 kg, 15 V, 11.70 w/w) is added slowly into the reactor, and the mixture is stirred at 25±5° C.≥2 hrs. The mixture is cooled to 5±5° C. and stirred ≥2 hrs. Samples are drawn every 2±0.2 hrs for HPLC analysis until the concentration of Compound 4 in supernatant ≤7.0 mg/mL. The solid is removed by centrifugation and washed with $CH_3CN$ (42.1 kg, 3 V, 2.34 w/w).

HPLC analysis of the product reports area % of Compound 4 ≥95.0%. Chiral HPLC analysis of the product reports area % of IMG-7289-4 >98.0%. (HPLC purity: 97.7%, chiral HPLC purity: 100%)

The filter cake is dried in a vacuum oven ≥12 hrs at 40±5° C. Drying is continued until samples drawn for KF and LOD report LOD=8.2%, and KF=1.8%. HPLC analysis of the product reports area % of Compound 4 ≥95.0%. (HPLC purity: 97.7%, assay: 86.6%). The product (weight: 15.35 kg) is packaged in double layer LDPE plastic bags under $N_2$, sealed with cable ties within a fiber keg, and stored at 2~8° C.

Step 5(a): Synthesis of dodecyl (4S)-4-[4-(1H-1,2, 3-triazol-1-yl)benzoylamino]-5-(4-methyl-piperazin-1-yl)-5-oxopentanethioate Hydrochloride Salt (5a)

A reactor is flushed with $N_2$ by evacuation to ≤0.08 Mpa, followed by introduction of $N_2$. The flush procedure is repeated 3 times. An $N_2$ atmosphere is maintained throughout the procedure. DCM (276.00 kg, 15 V, 19.95 w/w) is charged into the reactor and and stirring is begun. Compound 4 (13.2 kg corrected weight, 1.0 eq.) is added into the reactor. The mixture is cooled to 5±5° C. 1-Dodecanethiol (8.10 kg, 1.20 eq.) is added, followed by DMAP (198 g, 0.05 eq.), then EDCI (7.71 kg, 1.20 eq.). The mixture is stirred ≥1 hr, then warmed to 20±5° C. A sample is drawn for HPLC analysis every 2±0.2 hours, and the reaction is continued until the area % of Compound 4 ≤3%. Soft water (66.50 kg, 5 V, 5.0 w/w) is then added, and the mixture is stirred ≥0.5 hr, then allowed to stand without stirring ≥0.5 hr. The layers are separated, and the aqueous phase is extracted with DCM (89.15 kg, 5 V, 6.65 w/w). The mixture is stirred ≥0.5 hr and allowed to stand without stirring ≥0.5 hr before the layers are separated. The combined organic layers are washed with aqueous NaCl solution (25 wt. %, 5 V). The mixture is stirred ≥0.5 hr and allowed to stand without stirring ≥ for at least 0.5 hr. The layers are separated and the organic phase is again washed with NaCl (25 wt. %, 5 V) The mixture is stirred ≥0.5 hr and allowed to stand without stirring ≥ for at least 0.5 hr. The organic layer is concentrated to 6~7 V at ≤40° C. under vacuum, then EtOH (161.45 kg, 15 V, 11.58 w/w) is added. The volume is reduced to 6~7 V at ≤50° C. under vacuum, then additional EtOH (65.60 kg, 6.3 V, 4.98 w/w) and $CH_3CN$ (282.65 kg, 26.7 V, 20.83 w/w) is added at 20±5° C. The mixture is stirred ≥1 hr at 5° C., then chilled to 10±5° C.

HCl/EtOH (5.07 kg, 28.9 wt. % by titration, 1.20 eq.) is then added dropwise into the reactor at 10±5° C., and the mixture is stirred ≥12 hr at 10±5° C. The solid that forms is removed by centrifugation and washed with $CH_3CN$ (30.50 kg, 3 V, 2.34 w/w). HPLC analysis reports the area % of Compound 5 ≥95.0%. (HPLC purity: 99.3%). The product is dried in a vacuum oven ≥12 hrs at 45±5° C. Samples are drawn for LOD analysis every 5±0.2 hrs, and drying is continued until LOD ≤5.0%, Final LOD=3%. HPLC analysis reports Compound 5 ≥95.0% purity (HPLC purity: 99.1%, Assay: 94.9%). The product is transferred to double low density polyethylene (LDPE) bags with a tie within a fiber keg, weigh and stored below −20° C.

Example 5: Exploration of Steps in the Synthesis of N-[(2S)-1-(4-(methyl)piperazin-1-yl)-5-[[(1R, 2S)-2-(4-fluorophenyl)-cyclopropyl]amino]-1-oxo-pentan-2-yl]-4-(1H-1,2,3-triazol-1-yl)benzamide and its bis-tosylate Salt Exploration of Step 2: Removal of Boc Protecting Group.
Exploration of Reaction Conditions.

| HCl Source | Reaction conditions | 1 | 2 | Result |
|---|---|---|---|---|
| 4M HCl/$CH_3OH$ (10.0 eq.) 5 V THF 5 V $CH_3OH$ | 1 (150 g corrected mass) 5-25° C., 30 h. | 2.9% | 92.6% | N/A |
| 4M HCl/$H_2O$ (5.0 eq.) 10 V THF | 1 (10 g corrected mass) 5-25° C., 15 h. | 27.0% | 7.5% | Hydrolyzed impurity |
| 4M HCl/EtOAc (10.0 eq.) 10 V EtOAc | 1 (20 g corrected mass) 5-25° C., 20 h. | — | 87.5% | Light yellow solid |
| 4M HCl/dioxane (5.0 eq.) 5 V $CH_3OH$ | 1 (100 g corrected mass) 5-25° C., 20 h. | 1.7% | 92.0% | N/A |

Conclusion: Reaction in dioxane provided excellent yield and avoided hydrolysis to carboxylic acid.

Exploration of Solvent.

| Starting material | Reaction conditions | Temp, Time | 1 | 2 | Result |
|---|---|---|---|---|---|
| 1 (10 g corrected mass) in dioxane (5.0 V) | 4M HCl/dioxane (5.0 eq.) IPAc (2.0 V) | 25-30° C., 40 h. | 10.0% | 81.0% | — |
| 1 (10 g corrected mass) in dioxane (5.0 V) | 4M HCl/dioxane (7.0 eq.) | 25-30° C., 40 h. | 5.1% | 83.3% | White solid: 7.2 g Hygroscopic P: 81.2% Yield: 63.5% |
| 1(50 g corrected mass) in dioxane (5.0 V) | 4M HCl/dioxane (7.0 eq.) | 20-30° C., 10 h. | — | — | Sticky oil formed and adhered to the reactor internal wall. |
| 1 (50 g corrected mass) in dioxane (5.0 V) | 4M HCl/dioxane (7.0 eq.) | 20-30° C., 1 h. | — | — | Sticky oil formed, hard for scale up |
| 1(10 g corrected mass) in dioxane (5.0 V) | 4M HCl/dioxane (7.0 eq.) sulfolane (5 V) | 25-30° C., 18 h. | 5.41% | 90.05% | Crude oil |

Conclusion: Use of sulfolane as solvent gave excellent yield with useful physical properties for the resulting product.

Exploration of Sulfolane Volume.

Reactions were performed at 25-30° C. in the indicated solvent.

| Starting material | Reaction conditions | Time | 1 | 2 | Result |
|---|---|---|---|---|---|
| 1 in 5 V of dioxane (2.5 g crude solution, 1 g corrected mass) IPAc residual (1.13%, 0.03 g) | sulfolane (1 V) 4M HCl/dioxane (5.0 eq.) | 0.5 h. | — | — | Sticky oil formed and adhered to the reactor internal wall. |
| | sulfolane (2 V) 4M HCl/dioxane (5.0 eq.) | 0.5 h. | — | — | the reactor internal wall. |
| | sulfolane (3 V) 4M HCl/dioxane (5.0 eq.) | 0.5 h. | — | — | |
| | sulfolane (5 V) 4M HCl/dioxane (5.0 eq.) | 2 h. | 12.6% | 72.7% | Small amount of sticky oil formed and adhered to the reactor internal wall. |

| Starting material | Reaction conditions | Time | 1 | 2 | Result |
|---|---|---|---|---|---|
| | sulfolane (7 V) 4M HCl/dioxane (5.0 eq.) | 16 h. | n.d | 90.5% | Clear solution |

Conclusion: Use of 7 V of sulfolane avoided the formation of undesirable oils.

Exploration of Reproducibility.

Reactions were performed at 25-30° C.

| Rx part | Temp, Time | 1 | 2 |
|---|---|---|---|
| 1 (456.2 g crude solution, 100 g corrected weight) dioxane (5 V)/sulfolane (7 V) 4M HCl/dioxane (5.0 eq.) | 4.5 h | 1.9% | 92.1% |
| 1 (660 g crude solution, 145 g corrected weight) dioxane (5 V)/sulfolane (7 V) 4M HCl/dioxane (5.0 eq.) | 1 h | 2.6% | 91.9% |

Conclusion: Chosen solvent system gave acceptable reproducibility in product yield.

Exploration of Product Stability in Alkaline Conditions.

| Sample | Temp | Time | Assay |
|---|---|---|---|
| Obtain 1.1 g of Compound 3. Adjust pH to 10-11 with NaOH aqueous solution (6N). | 15~25° C. | 0 h | 0.7 g |
| | | +20 h | 0.5 g |
| | | +7 h | 0.4 g |
| | | +24 h | 0.3 g |
| | | +24 h | 0.2 g |
| Obtain 1.0 g of Compound 3. Adjust pH to 9-10 with 10 wt. % NaOH aqueous solution | 15~25° C. | 0 h | 1.0 g |
| | | +10 h | 1.0 g |
| | | +24 h | 1.0 g |
| | | +24 h | 1.0 g |
| Obtain 1.0 g of Compound 3. | 15~25° C. | 0 h | 1.0 g |
| Adjust pH to 9-10 with 10 wt. % $Na_2CO_3$ aqueous solution | | +10 h | 0.99 g |
| | | +24 h | 0.97 g |
| | | +24 h | 0.99 g |
| Obtain 1.0 g of Compound 3. Adjust pH to 9-10 with 6M LiOH aqueous solution | 15~25° C. | 0 h | 1.0 g |
| | | +10 h | 1.0 g |
| | | +24 h | 1.0 g |
| | | +24 h | 1.0 g |
| Obtain 1.0 g of Compound 3. Adjust pH to 9-10 with 10 wt. % $K_2CO_3$ aqueous solution | 15~25° C. | 0 h | 1.0 g |
| | | +10 h | 0.90 g |
| | | +24 h | 0.87 g |
| | | +24 h | 0.87 g |

Conclusions:

1) Compound 3 is not stable when pH>10 in basic aqueous solution.

2) Compound 3 is relatively stable in weak basic aqueous solution while pH=9-10

3) Compound 3 is relatively instable in the presence of $K_2CO_3$.

Exploration of Step 3: Amide Formation.

Exploration of Product Solubility.

| Condition | Solvent (10 V) | Solubility (mg/mL) |
|---|---|---|
| 300 mg Compound 3 slurry in solvent at 15~20° C. | MeOH | Dissolved completely |
| | EtOH | 22.5 mg/mL |
| | IPA | 14.1 mg/mL |
| | Acetonitrile | 29.5 mg/mL |
| | EtOAc | 9.0 mg/mL |
| | DCM | Dissolved completely |
| | IPAc | 4.8 mg/mL |
| | MTBE | 0.6 mg/mL |
| | THF | 84.2 mg/mL |
| | Heptane | insoluble |

Conclusion: Compound 3 has good solubility in DCM, THF or MeOH.

Exploration of Solvent Choice for Reaction and Workup.

Reactions were run at 20-25° C., using NMM (3.5 eq.)/HOBT (0.1 eq.), EDC.HCl (1.2 eq.).

| Reactants | Solvent | Time | 101 | 3 | Work up | Result & Purity & Yield |
|---|---|---|---|---|---|---|
| 101 (10 g, 1.0 eq.) 2 (1.2 eq.) | THF (13 V) $H_2O$ (2.3 V) | 2 h | 3.7% | 81.7% | Multiple IPAc extractions | light brown solid: 19.2 g; P: 94.1% Q-NMR: 92.4%: assay yield: 80.8% |
| 101 (10 g, 1.0 eq.) 2 (1.2 eq.) | DCM (25 V) | 1.5 h | 1.3% | 82.4% | Single DCM extraction | light brown solid: 19.1 g; P: 94.8% Q-NMR: 94.5% assay yield: 82.3% |
| 101 (40 g, 1.0 eq.) 2 (1.2 eq.) | DCM (25 V) | 1.5 h | 2.0% | 88.1% | Single DCM extraction | off-white solid: 73.4 g; P: 94.2% Q-NMR: 97.8% Yield: 82.0% |

Use of DCM for both reaction conditions and workup provides favorable results due to high yield and avoidance of tedious work up.

Exploration of Step 4: Methyl Ester Hydrolysis.
Exploration of Reaction Conditions.

| Rx part | Temp, Time | 4 | Result | Yield |
|---|---|---|---|---|
| 3 (1 g) Me$_3$SiOK (0.7 g, 2.0 eq.) THF (20 V); then HCl (3.0 eq) | 25-30° C., 3 h. | 94.6% | White solid, 0.95 g | 98.2% |
| 3 (2 g) Me$_3$SiOK (1.4 g, 2.0 eq.) THF (10 V); then HCl (2.0 eq) | 5-25° C., 3 h. | 94.4% | White solid, 1.85 g | 95.8% |
| 3 (40 g) Me$_3$SiOK (1.2 eq.) THF(10 V); then AMBERLITE ® IR120 | 25-30° C., 14 h. | 94.9% | | |

Conclusion: Use of Me$_3$SiOK for ester hydrolysis performed well under nonaqueous conditions.

Exploration of Reaction Conditions.

| Rx part | Time | 3 | 4 | Result |
|---|---|---|---|---|
| 3 (30.0 g) Me$_3$SiOK (1.2 eq.) THF (10 V) 20-30° C. | 4 h | 1.2% | 94.2% | White solid: 24.3 g LOD: 6.86% (wt. % of ACN from Q NMR: 6.5%) KF: 0.20%; ee: 95.3% Purity: 97.4% wt. % from Q NMR: 88.1% Yield: 73.9% |
| 3 (1.0 g) Me$_3$SiOK (1.2 eq.) MeOH (10 V) 10-20° C. | 4 h +14 h +24 h +24 h +24 h | 65.4% 31.2% 13.9% 7.4% 4.9% | 33.3% 66.0% 82.0% 88.4% 90.6% | No further workup |

Conclusion: Faster reaction in THF than in MeOH.

Exploration of the Choice of Solvent for Product Water Removal.

Compound 3 (2.0 g) reacted with Me$_3$SiOK (1.2 eq.) in THF (10.0 V) at 20-30° C. for 14 hrs. n-Heptane (10.0 V) was added, then the supernatant was removed. THF (10.0 V) and H$_2$O (1.0 V) were then added, and the pH was adjusted to 6.0-6.4 with AMBERLITE®. The mixture was filtered, and the filtrate was concentrated to 4-5 V, whereupon the mixture partitioned into an upper colorless phase and a lower orange phase.

| Process description | Result and comments |
|---|---|
| MeOH (5.0 V) and THF (5.0 V) added to residue. Resulting orange solution concentrated to 4-5 V. Process repeated: KF = 20.1%. Process repeated additional 3 times: KF = 7.6% | Inefficient |
| MeOH (5.0 V) and toluene (5.0 V) added to residue. Mixture partitions into two phases | Impractical: poor solvent miscibility |
| MeOH (2.0 V) and CH$_3$CN (10.0 V) added to residue. Resulting orange solution concentrated to 4-5 V. Process repeated: KF = 9.5%. Process repeated additional 2 times: KF = 0.7% | Potential applicability for water removal |
| MeOH (5.0 V) and CH$_3$CN (10.0 V) added to residue. Resulting orange solution concentrated to 4-5 V. Process repeated: KF = 14.5%. Process repeated additional 2 times: KF = 1.9% | |

Conclusion: Use of mixed MeOH/CH$_3$CN system useful for water removal.

Exploration of the Solubility of 4 in Various Solvents.

| Sample | Solvent (10 V) | Solubility (mg/mL) |
|---|---|---|
| 300 mg 4 slurry in solvent at 15~20° C. | MeOH | 37.0 mg/mL |
| | EtOH | 4.0 mg/mL |
| | IPA | 0.9 mg/mL |
| | Acetonitrile | 0.4 mg/mL |
| | EtOAc | 0.4 mg/mL |
| | DCM | 1.0 mg/mL |
| | IPAc | 1.0 mg/mL |
| | THF | 1.2 mg/mL |

Conclusion: Product 4 shows high stability in MeOH; lower solubility in other tested solvents.

Exploration of Product Recrystallization.

| Process description | Water removal process | Result and comments |
|---|---|---|
| 86.9 g (theoretical weight) Compound 4 in MeOH/CH$_3$CN (1.5 V/3.5 V) | Charge CH$_3$CN (15.0 V) into the solution at 40 ± 5° C. within 30 min. Stir ≥1 h. at 40 ± 5° C. Cool to 15 ± 5° C. and stir ≥6 h. at 15 ± 5° C. | White solid isolated. Part of solid remained adhered on the inner wall of the reactor. |
| 19.3 g (theoretical weight) Compound 4 in MeOH/CH$_3$CN (2.0 V/4.0 V) | Charge the solution into CH$_3$CN (15.0 V) dropwise at 25 ± 5° C. within 1 h. Stir ≥2 h. at 25 ± 5° C. | Separation of an oil. |
| 9.7 g (theoretical weight) Compound 4 in MeOH/CH$_3$CN (2.0 V/4.0 V) | Stir the solution at 20 ± 5° C. and add some crystal seeds. Large amount of white solid appeared within 5 min. Charge CH$_3$CN (15.0 V) and stir ≥10 h. at 20 ± 5° C. | White solid isolated. Part of solid remained adhered on the inner wall of the reactor. |
| 9.7 g (theoretical weight) Compound 4 in MeOH/CH$_3$CN (2.0 V/4.0 V) | Stir the solution at 30 ± 5° C. and add some seed crystals. Charge CH$_3$CN (15.0 V) after 10 min. Stir ≥10 h. at 20 ± 5° C. | White solid isolated. A small fraction of solid remained adhered on the inner wall of the reactor. |

Conclusion: seeding and temperature control were key parameters to the crystallization process.

Exploration of Step 5(a): Coupling with Thiol Plus Hydrochloride Salt Formation.

Exploration of Reaction Conditions.

Reaction was run with DMAP (0.05 eq.); workup: 1 eq. of HCl/EtOH at 20-30° C.

| Reaction conditions | Temp, Time | 4 | 5 | Result and comments |
|---|---|---|---|---|
| 4 (2 g) /DCM (10 V) HS(CH$_2$)$_{11}$CH$_3$ (1.2 eq.) EDCI (1.5 eq.) | 0-10° C. for 1 h.; 25° C. for 14 h. | 0.0% | 81.0% | White solid: 1.40 g P: 98.0% Yield: 45.1% |
| 4 (20 g)/DCM (15 V) HS(CH$_2$)$_{11}$CH$_3$ (1.2 eq.) EDCI (1.2 eq.) | 0-10° C. for 1 h.; 10-20° C. for 14 h. | 0.0% | 88.2% | White solid: 24.7 g P: 96.8% Yield: 79.6% |

Conclusion: Formation of HCl salt gave high yield of product with high purity and having useful physical properties.

Exploration of Solvent for Filtration.

Experiments were performed 15~25° C. for 20 h.

| Sample | Condition | Result |
|---|---|---|
| 5a (500 mg slurry) in solvent (20 V); charge HCl (EtOH) solvent | MeOH | Adhesive larger particles |
| | EtOH | Adhesive smaller particles |
| | IPA | Adhesive smaller particles |
| | EA | Gelatinous; not adhesive |
| | DCM | |
| | THF | |
| | ACN | Larger particles; not adhesive |
| | MTBE | Gelatinous; adhesive |
| | IPAc | |
| | NMP | Soluble |
| | DMSO | Soluble |
| 5a (15 g slurry) in solvent; then charge HCl (EtOH) solvent | EtOH (40 V) | Difficult filtration |
| | EtOH/ACN (1:2) (40 V) | Facile filtration |

Conclusion: ACN and EtOH/ACN solvent systems gave beneficial filtration properties.

Exploration of Step 6: Pd-Catalyzed Reduction.

Exploration of Timing and Temperature of Reduction of Compound 5

| Starting Materials | Reaction Conditions | IPC(LCMS) (Acid method) | |
|---|---|---|---|
| Reaction part | Temp./Time | 5 | 6 |
| Wet Pd/C (15 wt. %, Pd: 10%, water content: 56.5%) Et$_3$SiH (5.0 eq.) HOAc (1.5 eq.) THF (10 V) | 2.0 g scale | 0-5° C., 2 h | 43.4% | 54.9% |
| | | −5-5° C., 4 h | 0.8% | 94.7% |
| | | −5-5° C., 6 h | 0.3% | 97.4% |
| | 10.0 g scale | −5-0° C., 2 h | 32.2% | 67.7% |
| | | −5-5° C., 4 h | — | 99% |
| | | Workup | — | 99% |

Workup step resulted in 5 g light yellow solid for a yield of 77%.

Exploration of Choice for Pd Catalyst.

Solvent: THF (10 V)/HOAC (1.5 eq.). Reductant: Et$_3$SiH (5.0 eq.).

| Starting materials | Reaction conditions | 5 | impurity 6 |
|---|---|---|---|
| 5 (2.0 g) | 5 ± 5° C. for 36 h. | 72.4% | n.d. | 26.1% |
| Wet Pd/C (15 wt. %) | 5 ± 5° C. for 48 h. | 69.7% | n.d. | 28.9% |
| 5 (5.0 g) | 5 ± 5° C. for 24 h. | 32.4% | n.d. | 65.4% |
| Wet Pd/C (15 wt. %) | 5 ± 5° C. for 36 h. | 32.1% | n.d. | 65.4% |
| 5 (2.0 g) | 5 ± 5° C. for 12 h. | n.d. | 11.9% | 84.3% |
| Anhyd. Pd/C (7.5 wt. %) | 5 ± 5° C. for 24 h. | n.d. | 12.0% | 84.4% |
| 5 (2.0 g) | 5 ± 5° C. for 1 h. | n.d. | 3.7% | 92.4% |
| Anhyd. Pd/C (7.5 wt. %) | 5 ± 5° C. for 12 h. | n.d. | 17.4% | 78.2% |

Conclusion: Use of wet Pd/C susceptible to reaction stall before completeness. The reaction did not go to completion using a new batch of wet Pd/C from the same local vendor. The reaction performed more satisfactorily with anhydrous Pd/C, as compared to wet Pd/C.

Further Exploration of Choice of Pd Catalyst.

Solvent: THF (10 V)/HOAC (1.5 eq.). Reductant: Et$_3$SiH (4.0 eq.). Reactions were run at 10-20° C.

| Starting Materials | Time | IPC (HPLC) | | |
|---|---|---|---|---|
| | | 5 | Impurity | 6 |
| 5 (2.0 g, current campaign) Anhyd. Pd/C (2.5 wt. %, Shanxi Kaida, 16112311) | 2 h | 1.7% | n. d. | 95.4% |
| | 4 h | n. d. | 0.4% | 94.5% |
| | 5 h | n. d. | 0.2% | 94.7% |
| | 18 h | n. d. | 0.4% | 91.6% |
| 5 (2.0 g, current campaign) Anhyd. Pd/C (2.5 wt. %, Shanxi Kaida, 20161001) | 2 h | 26.1% | n. d. | 72.5% |
| | 4 h | 12.3% | 0.3% | 84.9% |
| | 5 h | 5.6% | 0.4% | 91.3% |
| | 18 h | n. d. | 0.9% | 94.1% |
| 5 (2.0 g, current campaign) Anhyd. Pd/C (2.5 wt. %, Shanxi Kaida, 20160919) | 2 h | 3.3% | n. d. | 94.4% |
| | 4 h | n. d. | 0.2% | 96.5% |
| | 5 h | n. d. | 1.1% | 94.6% |
| | 18 h | n. d. | 2.3% | 91.7% |
| 5 (2.0 g, current campaign) Anhyd. Pd/C (2.5 wt. %, Alfa, 170111219991) | 2 h | 9.4% | n. d. | 88.7% |
| | 4 h | n. d. | 0.1% | 95.9% |
| | 5 h | n. d. | 0.1% | 94.9% |
| | 18 h | n. d. | 0.3% | 91.3% |
| 5 (2.0 g, previous campaign) Anhyd. Pd/C (2.5 wt. %, Shanxi Kaida, 16112311) | 2 h | 36.9% | n. d. | 60.0% |
| | 4 h | 7.4% | 0.2% | 86.6% |
| | 6 h | 0.5% | 0.3% | 92.1% |
| | 22 h | n. d. | 0.3% | 90.7% |
| 5 (2.0 g, previous campaign) Anhyd. Pd/C (2.5 wt. %, Shanxi Kaida, 20161001) | 2 h | 30.6% | n. d. | 65.8% |
| | 4 h | 2.2% | 0.2% | 92.1% |
| | 6 h | n. d. | 0.3% | 93.1% |
| | 22 h | n. d. | 0.4% | 91.3% |
| 5 (2.0 g, previous campaign) Anhyd. Pd/C (2.5 wt. %, Alfa, 170111219991) | 2 h | 42.8% | n. d. | 53.9% |
| | 4 h | 16.1% | 0.2% | 78.7% |
| | 6 h | 2.6% | 0.3% | 90.5% |
| | 22 h | 0.8% | 0.3% | 90.0% |
| 5 (2.0 g, previous campaign) Anhyd. Pd/C (2.5 wt. %, Shanxi Kaida, 20160919) | 2 h | 25.5% | n. d. | 71.2% |
| | 4 h | 0.4% | 0.3% | 93.5% |
| | 6 h | n. d. | 0.4% | 92.8% |
| | 22 h | n. d. | 0.6% | 91.0% |

Conclusion: Reproducibility with various Pd catalysts not optimal.

Further Exploration of Choice of Pd Catalyst.

Reductant: Et$_3$SiH (4.0 eq.)

| Starting Materials | Reaction Conditions | 5 | Impurity | 6 |
|---|---|---|---|---|
| 5 (2.0 g, previous campaign) THF (10 V) HOAc (1.5 eq.) Pd(OH)$_2$/ C (15 wt. %) | 10~20° C., 0.5 h | 0.5% | — | 95.6% |
| | 10~20° C., +2 h | 0.4% | 1.0% | 95.5% |
| | 10~20° C., +5 h | 0.8% | 0.9% | 94.1% |
| | 10~20° C., +16 h | 0.5% | 1.0% | 94.3% |
| 5(2.0 g, previous campaign) THF (10 V) | 10~20° C., 0.5 h | 97.2% | — | 0.4% |
| | 10~20° C., +2 h | 7.9% | 7.4% | 79.9% |

-continued

| Starting Materials | Reaction Conditions | IPC (HPLC) 5 | Impurity | 6 |
|---|---|---|---|---|
| Pd(OH)₂/ C (15 wt. %) | 10~20° C., +5 h | 0.9% | 31.4% | 58.3% |
| | 10~20° C., +5 h | — | 42.3% | 44.6% |
| 5 (2.0 g, previous campaign) THF (10 V) / HOAc (1.5 eq.) Pd(OAc)₂ (1 wt.%) | 10~20° C., 0.5 h | 97.3% | — | 1.0% |
| | 10~20° C., 1.5 h | 97.7% | — | 1.0% |
| | 10~20° C., 3.5 h | 96.7% | — | 1.1% |
| | 10~20° C., +16 h | 94.6% | — | .1.1% |
| | 10~20° C., +8 h | 95.1% | — | 1.2% |
| 5 (2.0 g, previous campaign) THF (10 V) Pd(OAc)₂ (1 wt. %) | 10~20° C., 0.5 h | 98.0% | —* | 0.7% |
| | 10~20° C., 1.5 h | 60.0% | — | 35.6% |
| | 10~20° C., 3.5 h | 0.2% | 8.5% | 84.0% |
| | 10~20° C., +16 h | 0.1% | 22.7% | 53.5% |
| | 10~20° C., +8 h | — | 28.1% | 47.0% |
| 5 (2.0 g, previous campaign) THF (10 V) Pd(OAc)₂ (0.5 wt. %) | 10~20° C., 0.5 h | 95.5% | — | 0.5% |
| | 10~20° C., 2 h | 95.8% | — | 1.3% |
| | 10~20° C., 3 h | 92.5% | — | 4.5% |
| | 10~20° C., 5 h | 78.1% | — | 16.3% |
| | 10~20° C., +16 h | — | 4.7% | 84.3% |
| 5 (2.0 g, previous campaign) THF (10 V) Pd(OAc)₂ (0.1 wt.%) | 10~20° C., 0.5 h | 95.1% | — | — |
| | 10~20° C., 2 h | 96.7% | — | — |
| | 10~20° C., 3 h | 97.7% | — | — |
| | 10~20° C., 5 h | 93.9% | — | — |
| | 10~20° C., +16 h | 94.8% | — | — |
| 5 (2.0 g, previous campaign) THF (10 V) Pd(PPh₃)₄ (0.1 wt. %) | 10~20° C., 16 h | 98.2% | — | — |
| | Add 1.5 wt. % cat. 10~20° C., +3 h | 96.7% | — | — |
| | Add 7.5 wt. % cat. 10~20° C., +3 h | 95.5% | — | 0.4% |

Exploration of Use of Pd(OAc)₂ as Catalyst

Reductant: Et₃SiH (4.0 eq.).

| Starting Materials | Time | IPC (HPLC) 5 | Impurity | 6 |
|---|---|---|---|---|
| 5 (2.0 g, 1.0 eq.) THF (10 V) Pd(OAc)₂ (1 wt. %) −10~−5° C. | , 2 h | 95.56% | — | 1.26% |
| | 4 h | 95.68% | — | 1.39% |
| | 6 h | 94.09% | — | 2.21% |
| | 10 h | 93.02% | — | 3.80% |
| | 28 h | 93.28% | — | 4.10% |
| 5 (2.0 g, 1.0 eq.) THF (10 V) Pd(OAc)₂ (1 wt.%) 10~20° C. | 2 h | 90.33% | — | 7.57% |
| | 4 h | 66.34% | — | 30.92% |
| | 6 h | 52.15% | 1.63% | 43.42% |
| | 8 h | 15.92% | 6.05% | 74.77% |
| | 10 h | 0.21% | 10.70% | 84.84% |
| | 28 h | 0.33% | 33.44% | 61.60% |
| 5 (2.0 g, 1.0 eq.) HF (10 V) Pd(OAc)₂ (1 wt. %) 0~5° C. | 2 h | 84.46% | — | 12.72% |
| | 4 h | 51.79% | — | 44.57% |
| | 5 h | 16.96% | 3.84% | 76.085 |
| | 6 h | 0.36% | 9.99% | 84.61% |
| | 10 h | 0.39% | 35.91% | 54.91% |
| | 28 h | 0.41% | 92.27% | 2.78% |
| 5 (2.0 g, 1.0 eq.) THF (10 V) Pd(OAc)₂ (0.5 wt. %) 0~5° C. | 2 h | 97.91% | — | 0.39% |
| | 3 h | 97.81% | — | 0.43% |
| | 6 h | 93.40% | — | 4.69% |
| | 20 h | 89.79% | 0.11% | 8.50% |
| 5 (2.0 g, 1.0 eq.) THF (10 V) Pd(OAc)₂ (0.25 wt. %) 0~5° C. | 2 h | 98.09% | — | 0.15% |
| | 4 h | 98.19% | — | 0.12% |
| | 6 h | 98.16% | — | 0.11% |
| | 20 h | 98.71% | — | 0.12% |

Conclusion: Conversion to product was observed; impurity levels higher than using Pd/C catalyst.

Exploration of Variation in Acetic Acid Amounts.

Reductant: Et₃SiH (4.0 eq.). Catalyst: anhydrous Pd/C (7.5 wt. %). Reactions were run at 10-20° C.

| Starting Materials | Time | IPC (HPLC) 5 | Impurity | 6 |
|---|---|---|---|---|
| 5 (2.0 g, 1.0 eq.) THF (10 V) HOAc (0.1 eq.) | 1 h | 26.1% | 5.3% | 65.3% |
| | +3 h | — | 73.4% | 22.3% |
| | +5 h | — | 92.6% | 1.5% |
| 5 (2.0 g, 1.0 eq.) THF (10 V) HOAc (0.5 eq.) | 1 h | 0.9% | 3.7% | 90.9% |
| | +3 h | — | 78.6% | 16.9% |
| | +5 h | — | 90.0% | 3.1% |
| 5 (2.0 g, 1.0 eq.) THF (10 V) HOAc (1.0 eq.) | 1 h | 7.4% | 0.5% | 89.3% |
| | +3 h | — | 19.9% | 75.9% |
| | +5 h | — | 41.5% | 53.5% |

Conclusion: Presence of at least 1.0 eq of HOAc is required to reduce the amount of impurity.

Further Exploration of Choice of Starting Material.

The starting material 5 that was used for these trials was obtained without an intervening step of purification as hydrochloride salt 5a. Solvent: THF (10 V)/HOAc (1.5 eq.). Reactions were run at 10-20° C.

| Entry | Time | IPC (HPLC) 5 | Impurity | 6 |
|---|---|---|---|---|
| 5 (2.0 g, current campaign) Et₃SiH (4.0 eq.) Anhyd. Pd/C(2.5 wt. %, Shanxi Kaida, 16112311) | 2 h | 48.4% | n. d. | 47.2% |
| | 4 h | 34.9% | n. d. | 59.9% |
| | 6 h | 30.0% | 0.1% | 64.2% |
| | 22 h | 24.5% | 0.1% | 67.8% |
| 5 (2.0 g, current campaign) Et₃SiH (4.0 eq.) Anhyd. Pd/C (2.5 wt. %, Alfa, 170111219991) | 2 h | 57.4% | n. d. | 38.3% |
| | 4 h | 48.7% | n. d. | 46.3% |
| | 6 h | 42.4% | n. d. | 52.0% |
| | 22 h | 39.2% | 0.04% | 53.4% |

The above results, showing poor conversion to aldehyde 6, demonstrate the importance of purifying Compound 5 as its HCl salt 5a.

Further Exploration of Choice of Starting Material.

Alternate sources of 5, obtained without the intervening step of purification as the HCl salt, were subjected to alternate purification methods. Conversion to aldehyde 6 was explored. Solvent: THF (10 V)/HOAc (1.5 eq.). Reductant: Et₃SiH (4.0 eq.). Reactions were run at 10-20° C.

| Starting Materials | Time | IPC (HPLC) 5 | Impurity | 6 |
|---|---|---|---|---|
| 5 (3.0 g, after slurry with silica gel) Anhyd. Pd/C (2.5 wt. %, Shanxi Kaida, 16112311) | 2 h | 37.4% | 0.01% | 58.5% |
| | 4 h | 23.1% | 0.04% | 72.0% |
| | 6 h | 19.1% | 0.06% | 75.2% |
| | 22 h | 17.7% | 0.09% | 74.9% |
| 5 (3.0 g, after slurry with activated charcoal) Anhyd. Pd/C (2.5 wt. %, Shanxi Kaida, 16112311) | 2 h | 6.3% | 0.05% | 90.4% |
| | 4 h | 2.0% | 0.11% | 93.7% |
| | 6 h | 1.2% | 0.22% | 93.6% |
| | 22 h | 0.7% | 0.32% | 92.4% |
| 5 (10.0 g, after charcoal adsorption) Anhyd. Pd/C (2.5 wt. %) | 3 h | 0.87% | 3.7% | 88.06% |
| | 6 h | N/A | 19.9% | 72.7% |
| 5 (50.0 g, after charcoal adsorption) Anhyd. Pd/C (2.5 wt. %) | 3 h | 75.0% | N/A | 20.4% |
| | 6 h | 50.6% | N/A | 43.3% |
| | 15 h | 37.2% | 8.9% | 47.1% |

Conclusion: Reaction on a smaller scale (10 g) with material purified by charcoal adsorption proceeded well; however, reaction on a larger scale (50 g) stalled. These results confirmed that inclusion of the step of purification of 5 as its HCl salt is preferred.

Exploration of Water Content.

Solvent: THF (10 V)/HOAc (1.5 eq.)/water (as indicated). Reductant: Et$_3$SiH (4.0 eq.). Reactions were run at 10-20° C. and aliquots were drawn periodically for analysis.

| Starting Materials | Time | IPC (HPLC) 5 | Impurity | 6 |
|---|---|---|---|---|
| 5 (5.0 g, 1.0 eq. previous campaign) | 2 h | 75.3% | — | 22.1% |
| Anhyd. Pd/C (2.5 wt %) | 6 h | 75.6% | — | 22.9% |
| H$_2$O (2.0 eq.) | 12 h | 75.7% | — | 20.7% |
| 5 (5.0 g, 1.0 eq. previous campaign) | 2 h | 81.5% | — | 16.4% |
| Anhyd. Pd/C (2.5 wt %) | 6 h | 83.4% | — | 14.7% |
| H$_2$O (10.0 eq.) | 12 h | 82.1% | — | 15.5% |

Conclusion: The experimental result demonstrated that high water content results in a slow rate of reaction.

Exploration of Progress of Reaction.

Solvent: THF (10 V)/HOAc (1.5 eq.). Reductant: Et$_3$SiH (4.0 eq.). The reaction was run at 0-5° C. and aliquots were drawn periodically for analysis.

| Starting Materials | Time | IPC (HPLC) 5 | Impurity | 6 |
|---|---|---|---|---|
| 5 (10.0 g) | 2 h | 65.24% | — | 31.85% |
| Anhyd. Pd/C (2.5 wt %) | 6 h | 29.11% | — | 64.94% |
| | 8 h | 14.54% | — | 80.02% |
| | +20 h | 6.61% | 0.16% | 86.47% |
| | +24 h | 5.76% | 0.26% | 89.02% |
| | +28 h | 5.82% | 0.37% | 87.88% |
| 5 (10.0 g) | 2 h | 2.68% | — | 90.24% |
| Anhyd. Pd/C (5.0 wt %) | 6 h | 0.39% | 0.21% | 94.00% |
| | 8 h | 0.38% | 2.79% | 91.72% |
| | +20 h | 0.37% | 32.43% | 57.98% |
| | +24 h | 0.25% | 34.44% | 58.25% |
| 5 (10.0 g) | 2 h | 1.40% | — | 92.88% |
| Anhyd. Pd/C (7.5 wt %) | 5 h | — | 2.38% | 91.0% |
| | 8 h | — | 18.41% | 76.32% |
| | +20 h | 0.1% | 35.63% | 58.77% |
| | +24 h | 0.1% | 36.34% | 57.80% |

Conclusion: minimal impurity was formed with the use of 2.5 weight % catalyst with times less than 8 hr.

Exploration of Pd Catalyst Selection

Solvent: THF (10 V)/HOAc (1.5 eq.). Reductant: Et$_3$SiH (4.0 eq.). Reactions were run at 0-5° C.

| Starting Materials | Time | IPC (HPLC) 5 | Impurity | 6 |
|---|---|---|---|---|
| 5 (10.0 g, 1.0 eq.) | 2 h | 96.28% | — | 6.96% |
| 10 wt. % Wet Pd/C | 4 h | 16.95% | — | 81.43% |
| (egg shell for Pd distribution, | 6 h | 0.40% | — | 97.61% |
| completely reduced Pd[0]) | 8 h | 0.37% | — | 97.25% |
| Batch No.: (S316F01099) | 24 h | 0.36% | — | 97.04% |
| | 36 h | 0.29% | — | 96.92% |
| 5 (10.0 g, 1.0 eq.) | 2 h | 99.13% | — | 0.16% |
| Anhyd. Pd/C (5 wt. %) | 4 h | 98.71% | — | 0.75% |
| (egg shell for Pd distribution, | 6 h | 96.75% | — | 1.65% |
| containing un-reduced Pd[II]) | 8 h | 96.89% | 0.15% | 2.47% |
| Batch No.: (S314F00417) | 24 h | 0.42% | 69.54% | 28.20% |
| | 36 h | 0.17% | 69.69% | 27.95% |
| 5 (10.0 g, 1.0 eq.) | 2 h | 49.25% | — | 49.63% |
| Anhyd. Pd/C (5 wt. %) | 4 h | 1.96% | — | 96.17% |
| (egg shell for Pd distribution, | 6 h | 0.37% | 0.31% | 97.73% |
| reduced Pd[0]) | 8 h | — | 3.87% | 93.64% |
| Batch No.: (S316F00967) | 24 h | — | 41.05% | 56.94% |
| | 36 h | 0.10% | 40.57% | 56.67% |

Conclusion: Faster rate of reaction with completely reduced Pd(0) catalyst.

Exploration of Silane Quantity

Solvent: THF (10 V)/HOAc (1.5 eq.). Catalyst: anhyd. Pd/C (7.5 wt. %)

| Starting materials | Reaction conditions | 5 | impurity | 6 |
|---|---|---|---|---|
| 5 (1.0 g) Et$_3$SiH (3.0 eq.) | 5 ± 5° C. for 4 h. | 18.5% | n.d. | 79.3% |
| 5 (1.0 g) Et$_3$SiH (4.0 eq.) | 5 ± 5° C. for 4 h. | n.d. | 1.7% | 95.9% |
| 5 (1.0 g) Et$_3$SiH (5.0 eq.) | 5 ± 5° C. for 4 h. | 0.04% | 3.3% | 92.6% |

Conclusion: The reaction performed best by using more than 3 eq. of Et$_3$SiH.

Exploration of Pd Catalyst Loading.

Solvent: THF (10 V)/HOAc (1.5 eq.). Reductant: Et$_3$SiH (4.0 eq.).

| Starting materials | Reaction conditions | 5 | impurity | 6 |
|---|---|---|---|---|
| 5 (1.0 g,) | 5 ± 5° C. for 3 h. | 26.6% | n.d. | 72.2% |
| Anhyd. Pd/C (1.0 wt. %) | 5 ± 5° C. for 6 h. | 3.6% | 0.02% | 92.1% |
| | 5 ± 5° C. for 18 h. | 0.8% | 0.01% | 92.1% |
| 5 (1.0 g,) | 5 ± 5° C. for 3 h. | 26.1% | n.d. | 72.8% |
| Anhyd. Pd/C (2.5 wt. %) | 5 ± 5° C. for 6 h. | n.d. | 0.07% | 96.9% |
| | 5 ± 5° C. for 18 h. | n.d. | 0.24% | 96.1% |
| 5 (1.0 g,) | 5 ± 5° C. for 3 h. | 0.07% | 0.02% | 97.3% |
| Anhyd. Pd/C (5.0 wt. %) | 5 ± 5° C. for 6 h. | 0.04% | 0.02% | 94.8% |
| | 5 ± 5° C. for 18 h. | 0.08% | 0.03% | 96.4% |

Further Exploration of Pd Catalyst Loading.

Solvent: THF (10 V)/HOAc (1.5 eq.). Reductant: Et$_3$SiH (4.0 eq.).

| Catalyst; Temp | Time | 5 | Impurity | 6 |
|---|---|---|---|---|
| 5 (10 g); | 2.5 h | 17.57% | — | 80.17% |
| Pd/C (2.5 wt. %); | 3.5 h | 0.85% | — | 94.00% |
| 20~25° C. | 4.5 h | 0.36% | 7.64% | 88.52% |
| | 5.5 h | 0.31% | 15.50% | 80.19% |
| | 6.5 h | 0.43% | 21.61% | 73.51% |
| | 7.5 h | 0.48% | 25.07% | 68.30% |
| | 8.5 h | 0.33% | 35.74% | 56.83% |
| | 20.5 h | 0.35% | 53.92% | 36.72% |
| 5 (10 g); | 2.5 h | 45.45% | — | 53.61% |
| Pd/C (3.0 wt. %); | 3.5 h | 36.11% | — | 62.72% |
| 0~5° C. | 4.5 h | 42.15% | — | 56.52% |
| | 5.5 h | 31.86% | — | 66.17% |
| | 6.5 h | 16.98% | — | 80.27% |
| | 7.5 h | 25.05% | 0.02% | 72.78% |
| | 8.5 h | 16.16% | 0.08% | 79.89% |
| | 20.5 h | 0.29% | 24.48% | 71.91% |
| 5 (10 g); | 2.5 h | 13.27% | — | 84.38% |
| Pd/C (4.0 wt. %); | 3.5 h | 1.53% | — | 96.70% |
| 0~5° C. | 4.5 h | 1.68% | — | 96.60% |
| | 5.5 h | 0.23% | — | 97.35% |
| | 6.5 h | 0% | — | 96.41% |
| | 7.5 h | 0.38% | 0.19% | 96.65% |

| Catalyst; Temp | Time | 5 | Impurity | 6 |
|---|---|---|---|---|
|  | 8.5 h | 0.35% | 1.32% | 93.52% |
|  | 20.5 h | 0.29% | 31.34% | 63.40% |
| 5 (10 g); | 2.5 h | 34.51% | — | 64.07% |
| Pd/C (5.0 wt. %); | 3.5 h | 19.72% | — | 78.06% |
| 0~10° C. | 4.5 h | 15.19% | — | 82.48% |
|  | 5.5 h | 5.45% | 0.05% | 91.44% |
|  | 6.5 h | 2.24% | 0.07% | 94.52% |
|  | 7.5 h | 1.30% | 0.09% | 95.22% |
|  | 8.5 h | 0.44% | 0.56% | 94.02% |
|  | 20.5 h | 0.37% | 31.82% | 64.28% |

Conclusion: Use of either 4.0 wt % or 5.0 wt % catalyst provides nearly complete conversion to product. Decrease in product and increase in impurity observed with prolonged reaction time and should be avoided.
Exploration of Reaction Scale-Up.
Solvent: THF (10 V)/HOAc (1.5 eq.). Reductant: Et$_3$SiH (4.0 eq.).

| Starting materials | Reaction conditions | 5 | impurity | 6 |
|---|---|---|---|---|
| 5 (100.0 g) Anhydr. Pd/C (2.5 wt. %) | 5-20° C. for 1 h; 15 ± 5° C. for 17 h | n.d. | 4.1% | 91.2% |
| 5 (100.0 g) Anhydr. Pd/C (2.5 wt. %) | 5-20° C. for 1 h; 15 ± 5° C. for 8 h | n.d. | 0.8% | 94.6% |
| 5 (50.0 g) Anhydr. Pd/C (2.5 wt. %) | 5-20° C. for 1 h; 15 ± 5° C. for 8 h | n.d. | 4.1% | 91.1% |
| 5 (50.0 g) Anhydr. Pd/C (2.5 wt. %) | 5-20° C. for 1 h; 15 ± 5° C. for 8 h | n.d. | 4.3% | 91.6% |

Reaction performed satisfactorily at 100 g scale.
Verification of Larger Scale Reaction.
Solvent: THF (10 V)/HOAc (1.5 eq.). Catalyst: Pd/C (4.0 wt %). Reductant: Et$_3$SiH (4.0 eq.). Temp −5~10° C.

| Reactant | Time | 5 | Impurity | 6 | Comments |
|---|---|---|---|---|---|
| 5 (50.0 g) | 3.0 h | 0.46% | 0.61% | 96.43% | 26.2 g. HPLC Purity: 93.40% Assay: 81.79% |
| 5 (50.0 g) | 3.0 h | 0.43% | 1.31% | 94.79% | 29.7 g. HPLC Purity: 97.83% Assay: 97.00% |
| 5 (50.0g) | 3.0 h | 1.39% | 0.13% | 95.74% | 29.3 g. HPLC Purity: 97.17% Assay: 97.47% |
| 5 (50.0 g) | 3.0 h | 10.07% | — | 68.27% | Without further purification |
|  | 5.0 h | 12.88% | 0.13% | 85.38% |  |
|  | 7.0 h | 5.99% | 1.39% | 90.56% |  |
|  | 9.0 h | 6.69% | 2.28% | 88.71% |  |
|  | 11.0 h | 0.56% | 5.78% | 90.30% |  |
| 5 (50.0 g) | 3.0 h | 40.47% | — | 58.73% | Without further purification |
|  | 5.0 h | 2.39% | — | 95.64% |  |
|  | 11.0 h | 0.44% | 10.38% | 86.09% |  |
|  | 13.0 h | 0.45% | 12.56% | 84.89% |  |
|  | 15.0 h | 0.44% | 14.44% | 82.56% |  |
|  | 17.0 h | 0.05% | 19.87% | 77.09% |  |
|  | 21.0 h | 0.45% | 25.12% | 72.63% |  |
| 5 (100.0 g) | 3.0 h | 0.43% | — | 97.57% | Crude weight: 72.6 g |
|  | 5.0 h | 0.48% | 1.43% | 95.67% | HPLC Purity: 83.44 |
|  | 7.0 h | 0.50% | 7.59% | 89.42% | Impurity@ 14.7 min: |
|  | 9.0 h | 0.43% | 10.64% | 86.80% | 12.75% |

Conclusion: Reaction is highly repeatable. High level of conversion with low level of impurity can be accomplished by careful control of reaction time.
Exploration of Repeatability.
Solvent: THF (10 V)/HOAc (1.5 eq.). Reductant: Et$_3$SiH (4.0 eq.). Catalyst: Anhydr. Pd/C (2.5 wt. %)

| Starting materials | Reaction conditions | 5 | impurity | 6 | Comments |
|---|---|---|---|---|---|
| 5 (20.0g) | 5-20° C. for 1 h; 15 ± 5° C. for 6 h | n.d. | 1.6% | 91.0% | HPLC purity: 94.6% Off-white solid: 13.7 g Assay: 85.9% Assay mass: 11.8 g Yield: 89.8% |
| 5 (20.0 g) | 5-20° C. for 1 h; 15 ± 5° C. for 6 h | 0.4% | 0.5% | 92.3% | HPLC purity: 93.1% Off-white solid: 2.2 g Assay: 89.7% Assay mass: 10.9 g Yield: 82.9% |

Conclusion: Repeatability of selected conditions is excellent.
Exploration of Step 7: Reductive Amination.
Exploration of Various Reductants.

| Reaction part | Starting Materials | | Reaction Conditions | IPC(HPLC) | |
|---|---|---|---|---|---|
|  |  | Reductant | Temp./Time | 6 | 7 |
| 1 | 6 (500 mg) 9 (1.0 eq.) THF (10 V) | NaBH$_3$CN (1.4 eq.) | −5-5° C., 2 h 10-20° C., 12 h | 4.2% 8.7% | 39.1% 39.3% |
| 2 |  | Py.BH$_3$ (1.4 eq.) | 0 ± 5° C., 1 h 15 ± 5° C., 2 h | 44.4% 15.7% | 55.1% 53.1% |
| 3 |  | STAB (1.0 eq.) | −5-5° C., 2 h 10-20° C., 12 h | 13.4% 6.1% | 68.1% 60.4% |
| 4 |  | H$_2$ (1-2 atm), wet Pd/C (1.0 eq.) 15 wt % | 10-20° C., 12 h | 86.1% | — |
| 5 | 6 (500 mg) 9 (1.0 eq.) THF (7 V)/ MeOH (14 V) | NaBH$_4$ (1.0 eq.) | −5-5° C., 2 h 10-20° C., 12 h | 2.2% 3.1% | 80.9% 78% |

Conclusion: Best performance is achieved with NaBH$_4$.
Exploration of Reaction Stoichiometry.
Solvent: THF (7 V)/MeOH (14 V). Reductant: NaBH$_4$ (1.0 eq.)

| Starting materials | Reaction conditions | 6 | 7 | comments |
|---|---|---|---|---|
| 6 (7.29 g in THF solution by assay) 9 in THF solution (1.1 eq.) | −10° C. for 2 h.; 15-25° C. for 1 h. 15-25° C. for 16 h. | 0.5% 0.5% | 81.2% 82.9% | Purity: 84.96% Assay: 14.71% Assay Yield: 73.1% |
| 6 (10.0 g) in THF solution (1.0 eq.) 9 (1.0 eq.) | −15-5° C. for 2 h. 10-20° C. for 18 h. 10-20° C. for additional 24 h. | n.d. n.d. n.d. | 82.3% 81.6% 83.1% | IPA solution Assay mass: 10.2 g P: 82.2% Assay yield: 75.5% |

Conclusion: Reduction of Compound 9 to 1.0 equivalents can be achieved without loss in product yield or purity.
Exploration of Reproducibility.
Solvent: MeOH (14.0 V)/THF (7.0 V).

| Starting materials | Reaction conditions | 6 | 7 | Comments |
|---|---|---|---|---|
| 6 (9.4 g, 1.0 eq.) 9 (1.0 eq.) NaBH$_4$ (1.0 eq.) | −10 ± 5° C., 2 h.; 20 ± 5° C., 2 h. | 4.3% | 78.4% | HPLC purity: 83.4% IPA solution: 70.3 g Assay: 14.2% Assay mass: 10.0 g Yield: 78.7% |
| 6 (9.4 g, 1.0 eq.) 9 (1.0 eq.) NaBH$_4$ (1.0 eq.) | −10 ± 5° C., 2 h; 20 ± 5° C., 2 h. | 2.2% | 81.3% | HPLC purity: 88.5% IPA solution: 71.3 g Assay: 14.0% Assay mass: 10.0 g Yield: 78.7% |

Conclusion: Repeatability of selected conditions is excellent.

Further Exploration of Reproducibility.

Solvent: MeOH (14.0 V)/THF (7.0 V).

| Starting materials | Reaction conditions | 6 | 7 | Comments |
|---|---|---|---|---|
| 6 (15.0 g, 1.0 eq.) 9 (5.9 g, 1.0 eq.) NaBH$_4$ (1.48 g, 1.0 eq.) | −10 ± 5° C., 2 h 20 ± 5° C., 1 h | — | 89.88% | 16.80 g. HPLC Purity: 90.08% Assay: 13.79% |
| 6 (15.0 g, 1.0 eq.) 9 (5.9 g, 1.0 eq.) NaBH$_4$ (1.48 g, 1.0 eq.) | −10 ± 5° C., 2 h 20 ± 5° C., 1 h | — | 86.97% | 16.88 g. HPLC Purity: 90.32% Assay: 15.31% |

Conclusion: Repeatability of selected conditions on a larger scale is excellent.

Exploration of Step 8: Tosylate Salt Formation

Exploration of Solvents and Volume Ratios for Recrystallization of Tosylate Salt.

| | | Filter cake | | |
|---|---|---|---|---|
| Crude product | Solvent (10 V) | Filtrate loss (wt %) | Purity (%) | Major impurity (%) |
| HPLC purity: 97.9%, Major impurity: 0.94% 100 mg for each slurry at 25 ± 5° C. | MeOH | 8.6 | 99.5 | 0.23 |
| | EtOH | 1.2 | 98.4 | 0.84 |
| | IPA | 0.2 | 97.6 | 1.1 |
| | IPOAc | 0 | 97.7 | 1.1 |
| | THF | 0.1 | 97.7 | 1.1 |
| | DCM | 0.3 | 97.6 | 1.1 |
| | EtOAc | 0 | 97.7 | 1.1 |
| | MTBE | 0.03 | 97.7 | 1.1 |

| | | | Filter cake | | |
|---|---|---|---|---|---|
| Sample | Solvent | Condition | Purity | Max single impurity | Yield |
| 1.0 g crude 8 HPLC purity: 97.9%, Max single impurity: 0.94%) | MeOH (10 V) | Slurry at 55-65° C. for 3 h and cool down to 25° C., stir for another 3 h | 99.68% | 0.32% | 79% |
| | MeOH (15 V) | | 99.52% | 0.16% | 76% |
| | MeOH/EtOAc (2.5 V/2.5 V) | | 99.31% | 0.44% | 80% |
| | MeOH/EtOAc (5 V/5 V) | | 99.26% | 0.37% | 80% |

Examination of Reproducibility.

Solvent:

| Starting materials | Reaction conditions | 8 | Comments |
|---|---|---|---|
| 7 (10.0 g, 1.0 eq.) in IPA solution TsOH (2.5 eq.) THF (12.0 V) IPA (4.0 V) | 25 ± 5° C., 21 h. Slurry with MeOH/ EtOAc (5.0 V/5.0 V) 50 ± 5° C., 3 h.; 25 ± 5° C., 3 h. Slurry with n-heptane (10.0 V) 25 ± 5° C. for 3 h. Dry in vacuo at 35 ± 5° C. for 25 h. | 98.2% 99.6% 99.4% 100% | White solid: 12.7 g Yield: 76.4% KF: 0.8% Residual Solvent: MeOH: 383 ppm; EtOAc: 1866 ppm; n-Heptane: 1745 ppm; other solvents: not detected Pd content: <LOQ |
| 7 (10.0 g, 1.0 eq.) in IPA solution TsOH (2.5 eq.) THF (12.0 V) IPA (4.0 V) | 25 ± 5° C., 15 h. Slurry with MeOH/ EtOAc (5.0 V/5.0 V) 50 ± 5° C., 3 h.; 25 ± 5° C., 3 h. Slurry with n-heptane (10.0 V) 25 ± 5° C. for 3 h. Dry in vacuo at 35 ± 5° C. for 20 h. | 98.5% 99.4% 99.6% 100% | White solid: 13.4 g Yield: 80.6% KF: 1.0% Residual solvent: MeOH: 903 ppm; EtOAc: 1881 ppm; n-Heptane: 1034 ppm; IPA: 120 ppm; other solvents: not detected Pd content: <LOQ |

Conclusion: Repeatability of selected conditions is excellent.

Further Examination of Reproducibility.

Solvent: IPA (12 V)/THF (4 V)

| Starting materials | Stepwise Reaction conditions | 8 | Comments |
|---|---|---|---|
| 7 (10.0 g, 1.0 eq.) TsOH•H$_2$O (2.5 eq.) | Allow to react: 25 ± 5° C., 15 h Dry in vacuo: 35 ± 5° C., 15 h Dissolve in MeOH (34 V): 50 ± 5° C., 3 h Concentrate to 5~6 V Slurry with 6.0 V EtOAc: 50 ± 5° C., 3 h; 25 ± 5° C., 3 h Slurry with 10.0 V n-Heptane: 25 ± 5° C., 3 h Dry in vacuo: 35 ± 5° C., 15 h | 98.84% 98.65% 99.65% 99.72% | Weight: 13.1 g Assay: 98.7% Solvent residual: n-heptane: 167 ppm; no other solvents Chiral HPLC: 99.86% Pd residual: <LOQ (2.8 ppm) ROI: 0.03% |
| 7 (10.0 g, 1.0 eq.) TsOH•H$_2$O (2.5 eq.) | Dry in vacuo: at 25 ± 5° C., 15 h Dry in vacuo at 35 ± 5° C. for 15 h Dissolve in 34 V MeOH: 50 ± 5° C., 3 h Concentrate to 5~6 V Slurry with 6.0 V EtOAc: 50 ± 5° C., 3 h; 25 ± 5° C., 3 h Slurry with 10.0 V n-Heptane: 25 ± 5° C., 3 h Dry in vacuo: 35 ± 5° C. for 15 h | 98.80% 98.33% 99.74% 99.85% | Weight: 12.6 g Assay: 98.3% Solvent residual: n-heptane:198 ppm; no other solvents Chiral HPLC: 99.88% Pd residual: <LOQ (2.8 ppm) |

Conclusion: Repeatability of selected conditions is excellent.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A process for preparing N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 7), comprising:

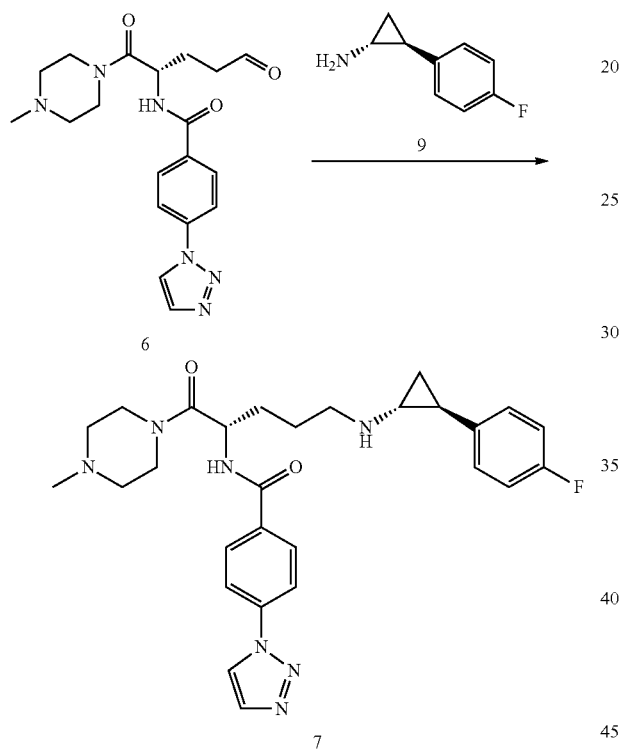

reacting (1R,2S)-2-(4-fluorophenyl)cyclopropan-1-amine (Compound 9) with Compound 6 under reductive amination conditions.

2. The process of claim 1, wherein said reductive amination conditions comprise reacting Compound 9 with Compound 6 in the presence of a borohydride reducing agent.

3. The process of claim 2, wherein the borohydride reducing agent is NaBH$_4$.

4. The process of claim 3, wherein the reaction is performed in a co-solvent mixture comprising methanol and tetrahydrofuran.

5. The process of claim 4, wherein NaBH$_4$ is added to a mixture of Compound 6 and Compound 9 in a mixture of methanol and tetrahydrofuran which has been cooled to −10±0.5° C.

6. The process of claim 5, wherein the NaBH$_4$ is added in portions while maintaining the reaction mixture temperature at −10±0.5° C.

7. The process of claim 6, wherein the NaBH$_4$ is added in at least 5 portions spaced at least 15 minutes apart.

8. The process of claim 7, further comprising stirring the reaction mixture at 20±5° C. following completion of the addition of NaBH$_4$ in portions.

9. A process for preparing Compound 6, comprising:

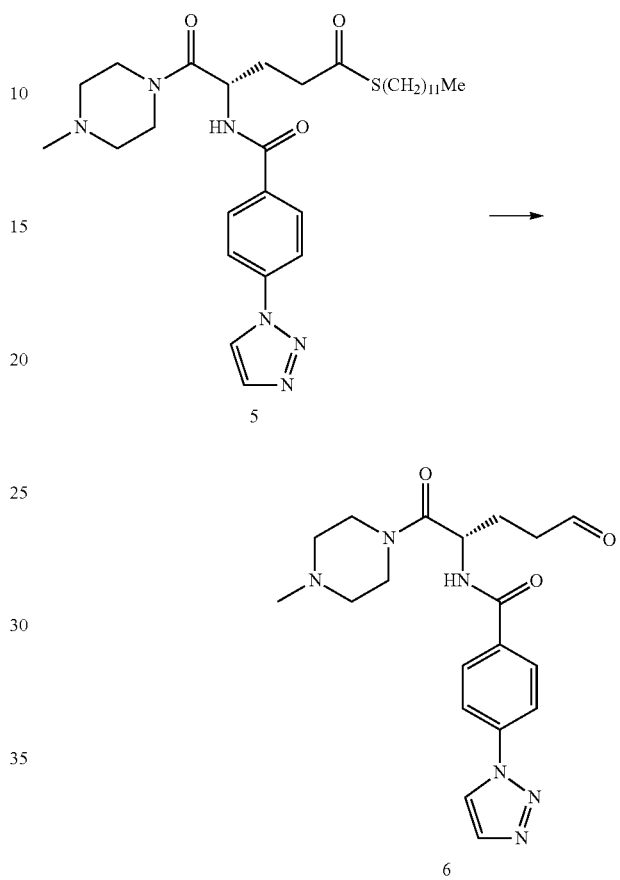

reacting thioester Compound 5 with a silane reducing agent to produce aldehyde Compound 6.

10. The process of claim 9, wherein said silane reducing agent is triethylsilane.

11. The process of claim 9, further comprising palladium on carbon.

12. The process of claim 9, wherein the reaction is performed in a solvent comprising glacial acetic acid.

13. The process of claim 12, wherein the reaction is performed in a solvent mixture comprising glacial acetic acid and tetrahydrofuran.

14. The process of claim 13, comprising adding triethylsilane to a mixture of Compound 5 and palladium on carbon in tetrahydrofuran and glacial acetic acid.

15. The process of claim 14, comprising adding triethylsilane over at least 30 minutes to a mixture of Compound 5 and palladium on carbon in tetrahydrofuran and glacial acetic acid, wherein said mixture has been cooled to 5±5° C.

16. A process for preparing the bis-tosylate salt (Compound 8) of N-[2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (Compound 7), comprising:

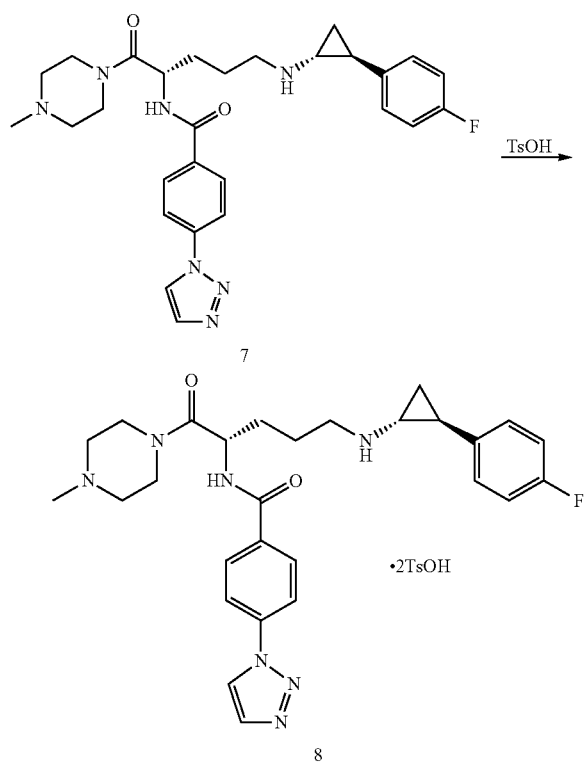

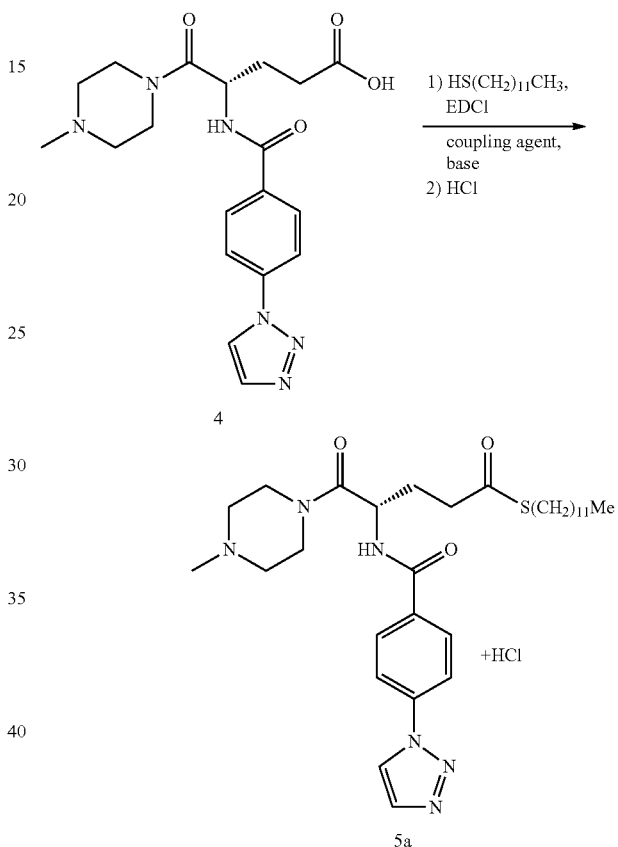

adding a solution of p-toluenesulfonic acid hydrate in tetrahydrofuran to a stirred solution of Compound 7 in tetrahydrofuran and isopropyl alcohol.

17. The process of claim 16, wherein the reaction mixture temperature is 25±5° C.

18. The process of claim 16, wherein 2.5 equivalents of p-toluenesulfonic acid hydrate relative to Compound 7 are added to the solution of Compound 7 in tetrahydrofuran and isopropyl alcohol.

19. The process of claim 18, further comprising the steps of:
   a) filtering the reaction mixture; and
   b) washing the filter cake with isopropyl alcohol; and
   c) drying the filter cake at 35±5° C. under vacuum for at least 15 hours.

20. The process of claim 19, further comprising the steps of:
   d) combining the filter cake with a mixture of methanol and ethyl acetate;
   e) stirring the resulting mixture;
   f) removing the reaction product by filtration; and
   g) washing the filter cake with ethyl acetate.

21. The process of claim 20, wherein 5 volumes of methanol relative to the filter cake and 5 volumes of ethyl acetate relative to the filter cake are used for stirring.

22. The process of claim 21, wherein the filter cake is stirred for at least 3 hrs with methanol at 50±5° C., and for at least 3 hrs with methanol at 25±5° C.

23. The process of claim 22, further comprising the steps of:
   h) combining the filter cake with heptane;
   i) stirring the resulting mixture;
   j) removing the reaction product by filtration; and
   k) washing the filter cake with heptane; and
   l) drying the filter cake under vacuum.

24. A process for preparing the hydrochloride salt of dodecyl (4S)-4-[4-(1H-1,2,3-triazol-1-yl)benzoylamino]-5-(4-methylpiperazin-1-yl)-5-oxopentanethioate (5a) comprising:

a) reacting dodecanethiol with (4S)-4-[4-(1H-1,2,3-triazol-1-yl)benzoylamino]-5-(4-methylpiperazin-1-yl)-5-oxopentanoic acid in the presence of a coupling agent and base, and;
   b) addition of hydrochloric acid.

25. The process of claim 24, wherein the carboxylic acid coupling agent is a carbodiimide.

26. The process of claim 25, wherein the carbodiimide is 1-ethyl-3-(3 dimethylaminopropyl)carbodiimide, 1.2 equivalents of dodecanethiol relative to Compound 4 are used, and the base is 4-dimethylaminopyridine.

27. A compound prepared by the process of claim 9.

28. A compound prepared by the process of claim 24.

* * * * *